United States Patent [19]

Garst

[11] Patent Number: 5,268,387

[45] Date of Patent: Dec. 7, 1993

[54] PHARMACEUTICAL COMPOSITIONS AND METHOD FOR ADMINISTERING 3 AND 4-SUBSTITUTED 2(5H)-FURANONES TO A MAMMAL FOR INHIBITING BONE LOSS

[75] Inventor: Michael E. Garst, Newport Beach, Calif.

[73] Assignee: Allergan, Inc., Irvine, Calif.

[21] Appl. No.: 872,308

[22] Filed: Apr. 24, 1992

[51] Int. Cl.$^5$ ............................................. A61K 31/34
[52] U.S. Cl. .................................................. 514/461
[58] Field of Search ........................ 514/461, 465, 466

[56] References Cited

U.S. PATENT DOCUMENTS

| | | | |
|---|---|---|---|
| 2,359,096 | 9/1944 | Elderfield | 260/239.5 |
| 2,359,208 | 9/1944 | Elderfield | 260/344 |
| 4,447,445 | 5/1984 | Jacobs | 424/279 |
| 4,786,651 | 11/1988 | Wheeler | 514/460 |
| 4,789,749 | 12/1988 | Jacobs et al. | 549/313 |
| 4,855,320 | 8/1989 | Chatterjee et al. | 514/473 |
| 4,874,782 | 10/1989 | Bonjouklian et al. | 514/473 |
| 4,916,241 | 4/1990 | Hayward et al. | 549/313 |
| 4,935,530 | 6/1990 | Lee | 549/214 |
| 5,013,850 | 5/1991 | Lee | 549/222 |
| 5,037,811 | 8/1991 | Lee | 514/99 |
| 5,043,457 | 8/1991 | Lee | 549/222 |
| 5,045,564 | 9/1991 | Lee | 514/471 |
| 5,059,611 | 10/1991 | Lee | 514/336 |
| 5,081,147 | 1/1992 | Lee | 514/471 |
| 5,081,261 | 1/1992 | Lee | 549/222 |
| 5,082,954 | 1/1992 | Lee | 549/214 |
| 5,089,485 | 2/1992 | Lee | 514/99 |
| 5,112,853 | 5/1992 | Garst | 514/443 |

FOREIGN PATENT DOCUMENTS

| | | |
|---|---|---|
| 133376 | 2/1985 | European Pat. Off. . |
| 209274 | 1/1987 | European Pat. Off. . |
| 295056 | 6/1987 | European Pat. Off. . |
| 350878 | 1/1990 | European Pat. Off. . |

OTHER PUBLICATIONS

Bonjuklian, et al., Chemical Abstracts, vol. 106, 156260c, p. 670 (1987).
Reynolds, et al, J. Am. Chem. Soc., 110, pp. 5172-5177 (1988).
Tocanne et al., Chemical Abstracts 69 76581k, p. 7146 (1968).
Deems, et al, Biochimica et Bioiphysica Acta, 917 pp. 258-268 (1987).
Scheuer et al., Journal of the American Chemical Society 100:1 p. 307 (Jan. 4, 1978).
Graziano, et al., Chemical Abstracts 107, (1987), 236559t.
Roll et al., Org. Chem. 1988, 53 3276-8.
Negishi et al., J. Org. Chem 45, pp. 5223-5225, (1980).
E. D. de Silva et al., "Tetrahedron Letters", 21:1611-1614 (1980).
Nakagawa et al., "Aldose reductase inhibitor from Palaun sponges" Chem. Abstract 106: 96126b (1987).
Tanaka, et al., The Chemical Society of Japan, Chemistry Letters, pp. 633-636 (1983).
Tanis, et al., Tetrahedron Letters, vol. 25, No. 40, pp. 4451-4454 (1984)—Furans in Synthesis 4. Silyl Furans as Butenolide Equivalents.
Graziano, et al, "Photosensitized Oxidation Of Furans", Part 12, Solvent Effects In Thermal Rearrangement Of The 2,5-Peroxides Of 2,5-Unsubstituted Furans, J. Chem. Soc., Perkin Trans, 1, (8), 1833-9, Apr. 19, 1989.
David Nettleton, et al, Inflammation Research Association, Fifth International Conference Poster Session, Phospholipase $A_2$ Inhibition By Dihydrofuranones, Sep. 23-27, 1990.

Primary Examiner—Frederick E. Waddell
Assistant Examiner—T. J. Criares
Attorney, Agent, or Firm—Gabor L. Szekeres; Martin A. Voet; Robert J. Baran

[57] ABSTRACT

3 and 4-substituted 2(5H)-furanone compounds influence the balance between bone production and bone resorption in mammals, including humans. The active compounds are administered to mammals, including humans, in an effective dose which ranges between 0.05 to 100 mg per kilogram, body weight, per day, for the purpose of influencing the balance between bone production and bone resorption, and particularly for treating osteoporosis.

2 Claims, No Drawings

PHARMACEUTICAL COMPOSITIONS AND METHOD FOR ADMINISTERING 3 AND 4-SUBSTITUTED 2(5H)-FURANONES TO A MAMMAL FOR INHIBITING BONE LOSS

BACKGROUND OF THE INVENTION

1. Field of the Invention

The present invention is directed to pharmaceutical compositions comprising as active ingredients one or more 3- and 4-substituted 2(5H)-furanone compounds, and methods for administering such compositions to mammals, including humans, for the purpose of inhibiting bone loss.

2. Brief Description of the Prior Art

Osteoporosis is a disease which manifests itself in a decrease of bone density throughout the body. The descreased bone density is due to loss of calcium containing bone mineral and also due to loss of bone matrix (collagen). The disease of osteoporosis usually afflicts elderly patients, more frequently post menopausal women, although beyond the age of 80 the frequency of the disease is about the same in men as in women. The cause of osteoporosis is not well understood, nevertheless it is believed that bone is continuously formed and resorbed during the life of a mammal, including human, and that in persons suffering from osteoporosis the rate of bone resorption is faster than the rate of bone formation, resulting in a net loss of bone density. Thus, osteoporosis is a disease where the balance between bone production and resorption, especially the balance of deposit and resorption of calcium in the bone, is disturbed.

The present methods for treating osteoporosis include physical therapy, administration of anabolic agents, drugs containing phosphorous, vitamin D, calcium salts, fluoride salts calcitonin, and of the antibiotic mithramycin. In post-menopausal women estrogen replacement therapy is also employed to prevent or lessen bone loss.

Among the foregoing, mithramycin is believed to decrease the rate of bone desorption, and thus modify the balance between bone production and resoption. The prior art which is believed to be closest to the present invention is U.S. Pat. No. 4,916,241 describing certain 5-hydroxy-2(5H)-furanone derivatives which are substituted in the 4 position with a substituted phenyl-methyl, substituted phenylhydroxy-methyl, substituted phenyl alkyl, or with substituted phenyl-hydroxyalkyl groups, and which modify the balance between bone production and bone resorption in a host animal, including man.

As further background to the present invention, it is noted that several types of 4-substituted 2(5H)-furanone derivatives, especially 4-substituted 5-hydroxy-2(5H)-furanone derivatives, and certain 3 substituted 2(5H)-furanones as well, have been discovered and disclosed in the prior art to be anti-inflammatory, calcium channel blocking and/or antiproliferative agents. However, to the best knowledge of the present inventor the only disclosure of 4-substituted-5-hydroxy-2(5H)-furanone compounds as agents for modifying the balance between bone production and bone resoprtion is in the above-noted U.S. Pat. No. 4,916,241 reference.

Unfortunately, none of the known methods for treatment of osteoporosis, or more broadly speaking, methods for favorably modifying the balance between bone production and resorption, are entirely satisfactory. Therefore, the search continues in the art for better and/or additional agents for inhibiting bone loss. The present invention represents an important discovery and advance in the art in this regard.

SUMMARY OF THE INVENTION

The present invention covers a method of favorably modifying the balance between bone production and bone resorption in a host animal, including humans, and thereby inhibiting bone loss by administering certain 3- and 4-substituted 2(5H)-furanone and certain 4-substituted 5-hydroxy-2(5H)-furanone compounds to the host animal. The present invention also covers pharmaceutical compositions adapted for administration to host animals, including humans, for the purpose of inhibiting bone loss, such compositions containing an effective amount of one or more of the 4-substituted 2(5H)-furanone and 4-substituted 5-hydroxy-2(5H)-furanone compounds referred to above.

Specifically, the compounds which are administered in accordance with the present invention in a pharmaceutical composition for the purpose of modifying the balance between bone production and bone resorption, that is for inhibiting bonne loss, are shown by the following formulae:

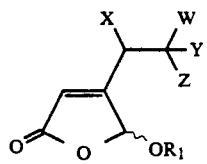

Formula 1

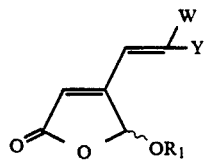

Formula 2

In Formula 1 and in Formula 2

$R_1$ is H or alkyl of 1 to 20 carbons, $CO-R_1^*$ $CO-O-R_1^*$ $CO-NH-R_1^*$ or $PO(OR_1^*)_2$ or $PO(OR_1^*)R_1^*$ where $R_1^*$ independently is alkyl of 1 to 20 carbons or phenyl;

X is long chain alkyl having 5 to 25 carbon atoms, long chain alkyl of 5 to 25 carbons substituted with an aryl group, or long chain alkyl of 5 to 25 carbons substituted with a fluoro substituted aryl group;

Y is $COOH$, $COOR_2$, $CONH_2$, $CONHR_2$, $CON(R_2)_2$, $CHO$, $COR_2$; $COCF_3$, $COCHF_2$, $CH=NR_2$, $CR_2=N-R_2$, $CH=N-NHR_2$, $CH=N-N(R_2)_2$, $CH=NOH$, $CR_2=N-OH$, $CH=NOR_2$, $CR_2=NOR_2$, $CH_2OH$, $CHR_2OH$, $C(R_2)_2OH$, $CH_2OR_2^*$ $CHR_2OR_2^*$ $C(R_2)_2OR_2^*$ $SO_2R_2$, $PO(OR_3)_2$, and $PS(OR_3)_2$, where $R_2$ independently is lower alkyl or phenyl, $R_2^*$ is lower alkyl, phenyl, alkanoyl having 1 to 6 carbons, or aroyl, and $R_3$ is H, lower alkyl, or phenyl;

W is H, lower alkyl, phenyl, $COOH$, $COOR_4$, $CONHR_4$, $CON(R_4)_2$ where $R_4$ is lower alkyl, and Z is H or alkyl.

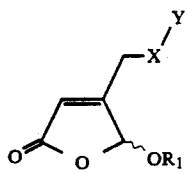

Formula 3

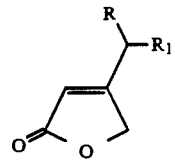

Formula 5

In Formula 3

$R_1$ is H or alkyl of 1 to 20 carbons, CO—$R_1^*$ CO—O—$R_1^*$ CO—NH—$R_1^*$ or PO(O$R_1^*$)$_2$ or PO-(O$R_1^*$)$R_1^*$ where $R_1^*$ independently is alkyl of 1 to 20 carbons, or phenyl with the proviso that when $R_1$ is CO—NH—$R_1^*$ then $R_1^*$ is not H;

X is O, S, SO—, SO$_2$, NH—, or N$R_2$ where $R_2$ is phenyl, or alkyl of 1 to 20 carbons, and Y is alkyl of 6 carbon atoms, aryl $C_1$-$C_6$ alkyl, aryl, alkenyl containing one or more olephinic bonds and 6 to 25 carbon atoms, CO—$R_3$, CO—O$R_3$, CONH$R_3$, SO$_2R_3$, SO$_2$NH$R_3$ where $R_3$ is aryl, alkyl of 4 to 25 carbons, alkenyl of 4 to 25 carbons containing one or more olephinic bonds, further Y is (CH$_2$)$_n$—O—$R_4$, or (CH$_2$)$_n$—O—(CH$_2$)$_m$—O—$R_4$, where n, and m, are integers and are independently 1 to 25 and $R_4$ is phenyl or alkyl of one to 20 carbons, still further Y is PO(OH)$_2$, PO(OH)O$R_5$, PO(OH)$R_5$ PO(O$R_5$)$_2$, where $R_5$ is independently phenyl, alkyl of 1 to 20 carbons or $R_5$ is (CH$_2$)$_n$—N($R_5^*$)$_3$ where $R_5^*$ is alkyl of 1 to 20 carbons, or Y is NH—$R_6$ where $R_6$ is phenyl, or alkyl of 6 to 25 carbon atoms with the proviso that when X is O, S, then Y is not NH—$R_6$, and with the further proviso that when X is SO or SO$_2$ then Y is not SO$_2R_3$ or SO$_2$NH$R_3$.

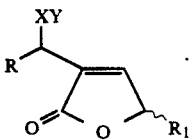

Formula 4

In Formula 4

R' is H or lower alkyl of 1 to 6 carbons;

R is alkyl having 4 to 25 carbons, carbocyclic arylalkyl or alkenyl containing 4 to 25 carbons and one or more olephinic bonds;

X is O, NH or N$R_1$, where $R_1$ is alkyl of 1 to 20 carbons or arylalkyl;

Y is H, alkyl of 1 to 20 carbons, carbocyclic arylalkyl, carbocyclic aryl, alkenyl containing one or more olephinic bonds and 2 to 20 carbons, PO(OH)$_2$, PO(OH)O$R_2$, PO(OH)$R_2$ PO(O$R_2$)$_2$, where $R_2$ is independently alkyl of 1 to 20 carbons or phenyl, further Y is CO—$R_3$, CO—O$R_3$, CONH$R_3$, SO$_2R_3$, SO$_2$NH$R_3$, (CH$_2$)$_n$—O—$R_3$, or (CH$_2$)$_n$—O—(CH$_2$)$_m$—O—$R_3$, where n, and m, are integers and are independently 1 to 20 and $R_3$ is H, alkyl having 1 to 6 carbons, alkenyl containing one or more olephinic bonds and 2 to 6 carbons, carbocyclic aryl, carbocyclic arylalkyl, with the proviso that when Y is CO—$R_3$, and CONH$R_3$ then $R_3$ is not hydrogen.

In Formula 5

R is $C_7$-$C_{20}$alkyl;

$R_1$ is OCO$R_2$, 2-(methoxy)ethoxymethoxy, halogen and NH$R_3$;

$R_3$ is H, $C_1$-$C_6$ alkanoyl, COCF$_3$ and $C_1$-$C_6$ sulfonyl;

$R_2$ is $C_1$-$C_{14}$alkyl or amino N-substituted by one α-($C_1$-$C_4$ alkyl)benzyl group, by one or two $C_1$-$C_4$ alkyl groups or by one phenyl group; or OP($R_4R_5$); or R is 2-(methoxy)ethoxymethoxymethyl and $R_1$ is OCO-($C_7$-$C_{14}$alkyl); or R is CH(OCOC$_1$-$C_4$alkyl)$C_7$-$C_{20}$alkyl and $R_1$ is OCO($C_1$-$C_4$lkyl); and $R_4$=$R_5$ is H or $C_1$-$C_4$ alkyl.

Formula 6

In Formula 6

A is CH$_2$—CO$_2$M, CH$_2$CH$_2$OCOR, (CH$_2$)$_n$CH=CHCOR, (CH$_2$)$_q$COR,

CH$_2$C(OH)$R_3$, CH$_2$CCH$_2$CO$_2$R, CH$_2$COCH=CH$R_1$,
  |                |
  R                R$_3$OCO

CH$_2$CH$_2$CHCO$_2R_1$, CH$_2$CH=CCO$_2R_1$, CHCO$_2R_1$ (CH$_2$)$_m$OX,
  |                       |                    |
  R                       R                    R (CH$_2$)$_m$CO$_2R_1$, CH$_2$C≡CCO$R_2$, CH$_2$CCH=CCO$_2R_1$
                                              |
                                              CO$_2$R

CH$_2$CON—CH$_2$CH$_2R_6$, CH$_2$C=N—$R_4$, or
       |                      |
       $R_1$                  $R_5$

CH$_2$CH$_2$CHCH$_2$CO$_2$M
        |
        OCO$R_3$ n is 1 or 2;
q is 1–4;
m is 8–12;
R is $C_7$-$C_{14}$ alkyl, $C_7$-$C_{14}$ alkoxide, N$R_3$(CH$_2$)$_p$Z or C=CM;
p is 2–8;
Z is H, N($R_3$)$_2$ or CO$_2$H;
$R_1$ is hydrogen or $C_1$-$C_4$ alkyl;
$R_2$ is $C_7$-$C_{14}$ alkyl or phenyl;
M is $C_7$-$C_{14}$ alkyl; phenyl($C_1$-$C_4$ alkyl) optionally substituted on the phenyl ring by 1-3 halo substituents; pyridyl($C_1$-$C_4$ alkyl) or naphthyl($C_1$-$C_6$ alkyl);
$R_4$ is O—($C_8$-$C_{14}$ alkyl) or NH($C_8$-$C_{14}$ alkyl); and $R_5$ is hydrogen or $R_4$ is OH and $R_5$ is o-hydroxyphenyl;
X is hydrogen, acetyl, PO(OH)$_2$ or CO(CH$_2$)$_3$N($R_3$)$_2$.HCl;
$R_3$ is $C_1$-$C_4$ alkyl and $R_6$ is phenyl or $C_4$-$C_{12}$ alkyl, and
$Y$ is $C_1$-$C_6$ alkanoyl.

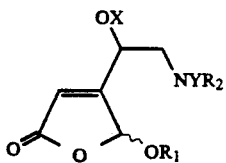

Formula 7

In Formula 7

$R_1$ is H or alkyl of 1 to 20 carbons, CO—$R_1$* CO—O—$R_1$* CO—NH—$R_1$* or PO(O$R_1$*)$R_2$* or PO(O$R_1$*)$R_1$* where $R_1$* independently is H, alkyl of 1 to 20 carbons, or phenyl;

$R_2$ is H or alkyl of 1 to 20 carbons;

X is H, $R_3$, CO—$R_3$, CO—O—$R_3$, CO—NH—$R_3$, CO—N—($R_3$)$_2$, PO(O$R_3$)$_2$ or PO(O$R_3$)$R_3$, and $R_3$ independently is H, phenyl, alkyl of 1 to 20 carbons or is alkyl of 1 to 20 carbons substituted with a hydroxyl, alkoxy, amino, thioalkoxy or with a CO$R_3$* group where $R_3$* is H, lower alkyl, OH, O$R_3$, NH$_2$, NH$R_3$ or N($R_3$)$_2$ group where $R_3$ independently is H or lower alkyl, with the proviso that when X is CO—O—$R_3$ or is CO—NH—$R_3$ then $R_3$ is not hydrogen;

Y is H, $R_4$, CO—$R_4$, CO—O—$R_4$, CO—N-piperazinyl, CO—N-substituted N-piperazinyl, CO—N-morpholinyl, CO—N-substitutetd N-morpholinyl, CO—NH—$R_4$, or CO—N($R_4$)$_2$, PO(O$R_4$)$_2$, PO-(O$R_4$)$R_4$, SO$_2$O$R_4$, or SO$_2$$R_4$, where $R_4$ independently is H, phenyl, phenyl substituted with two carboxyl groups, alkyl of 1 to 20 carbons, or is alkyl of 1 to 20 carbons substituted with a hydroxyl, alkoxy, dialkyl substituted amino, thioalkoxy, with a CO$R_4$* or with a O—CO$R_4$* group where $R_4$* is H, lower alkyl, OH, O$R_4$, NH$_2$, NH$R_4$ or N($R_4$)$_2$ group where $R_4$ is lower alkyl with the proviso that when Y is CO—O—$R_4$ then $R_4$ is not hydrogen.

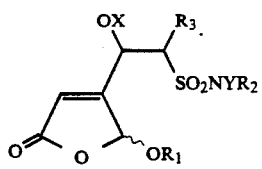

Formula 8

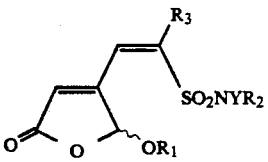

Formula 9

In Formula 8 and in Formula 9 $R_1$ is H or alkyl of 1 to 20 carbons, CO—$R_1$* CO—O—$R_1$* CO—NH—$R_1$* or PO(O$R_1$*)$_2$ or PO(O$R_1$*)$R_1$* where $R_1$* independently is H, alkyl of 1 to 20 carbons, or phenyl;

$R_2$ is H, alkyl of 1 to 20 carbons, or $R_2$ and Y jointly represent a heterocycle which incorporates the sulfonamide nitrogen in the ring as a heteroatom;

$R_3$ is H or alkyl of 1 to 20 carbons;

X is H, $R_4$, CO—$R_4$, CO—O—$R_4$, CO—NH—$R_4$, CO—N—($R_4$)$_2$, PO(O$R_4$)$_2$ or PO(O$R_4$)$R_4$, and $R_4$ independently is H, phenyl, alkyl of 1 to 20 carbons or is alkyl of 1 to 20 carbons substituted with a hydroxyl, alkoxy, amino, thioalkoxy, with a O—CO$R_4$* group or with a CO$R_4$* group where $R_4$* is H, lower alkyl, OH, O$R_4$, NH$_2$, NH$R_4$ or N($R_4$)$_2$ group where $R_4$ independently is H or lower alkyl, with the proviso that when X is CO—O—$R_4$ or is CO—NH—$R_4$ then $R_4$ is not hydrogen;

Y is H, phenyl or carboxy substituted phenyl, or alkyl of 1 to 20 carbons, or is alkyl of 1 to 20 carbons substituted with a hydroxyl, alkoxy, dimethyl substituted amino, thioalkoxy, O—PO(O$R_5$)$_2$, O—PO(O$R_5$)$R_5$, O—SO$_3$H, O—SO$_2$$R_5$, O—CO$R_5$, or CO$R_5$ group where $R_5$ is H, lower alkyl, OH, O$R_5$*, NH$_2$, NH$R_5$* or N($R_5$*)$_2$ group where $R_5$* is lower alkyl, or $R_2$ and Y jointly represent a heterocycle which incorporates the sulfonamide nitrogen in the ring as a heteroatom, with the proviso that when Y is an alkyl substituted with O—PO(O$R_5$)$_2$ or with O—PO(O$R_5$)$R_5$ then $R_5$ is not OH.

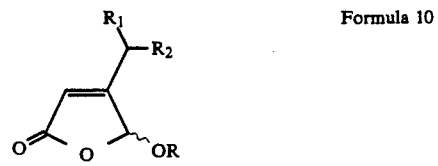

Formula 10

In Formula 10 R is hydrogen, $C_1$-$C_6$alkanoyl, $C_1$-$C_6$ carbamoyl, phenyl carbamoyl, $C_1$-$C_6$ dialkylphosphonate or PO(OH)$_2$;

$R_1$ is
halo,
NHCO$R_3$,
NHSO$_2$$R_8$,
NHPO(OCH$_3$)CH$_3$;
OCO$R_4$,
O$R_5$ or
S(O)$_m$$R_8$;
SCOCH$_3$;
OCONH-phenyl;
OCO—N(CH$_3$)CONH(CH$_3$)

$R_2$ is $C_8$-$C_{20}$ alkyl;

$R_3$ is $C_1$-$C_4$ alkyl, $C_1$-$C_4$ alkoxy, trifluoromethyl, —(CH$_2$)$_3$—COOH, NHR$_8$ or N—$R_9$$R_{10}$; $R_4$ is $C_1$-$C_4$ alkoxy, phenoxy, $R_6$-($C_1$-$C_4$ alkyl), or NHSO$_2$N(C$_2$H$_5$)$_2$;

$R_5$ is $C_8$-$C_{20}$ alkyl, phenyl, 2-methoxyethyl, 2-(methoxy) ethoxymethyl, t-butyl dimethylsilyl, PO-(OR$_7$)R$_8$ or PS(OR$_7$)R$_8$;

$R_6$ is carboxy, $C_1$-$C_4$ alkoxycarbonyl, halo or CONR$_{11}$R$_{11}$;

$R_7$ is hydrogen or $C_1$-$C_4$ alkyl or phenyl;

$R_8$ is $C_1$-$C_4$ alkyl, ethoxy, hydroxy, hydrogen or $C_1$-$C_6$ alkanoyl;

$R_9$ is H or $C_1$-$C_4$ alkyl;

$R_{10}$ is H, $C_1$-$C_4$ alkyl or SO$_2$NR$_2$R$_2$;

$R_{11}$ is H or $C_1$-$C_4$ alkyl; and m is 0-2.

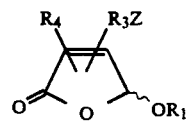

Formula 11

In Formula 11 the dotted line represents absence of a bond or a single bond;

$R_1$ is hydrogen, $C_1$-$C_4$ alkyl, benzyl, $C_1$-$C_{20}$ alkanoyl, cyclohexanoyl, benzoyl, phenyl ($C_{1-4}$ alkanoyl) or naphthoyl;

Z is —C(OR$_2$)H—;

R$_2$ is H, C$_1$-C$_4$ alkyl, C$_1$-C$_{20}$ alkanoyl, trihaloacetyl, cyclohexanoyl, benzoyl, phenyl(C$_{1-4}$ alkanoyl), phenyl(C$_2$-C$_{14}$ alkenoyl), naphthoyl, or carbamoyl optionally N-substituted by one or two C$_{1-4}$ alkyl groups or by one alpha-(C$_1$-C$_4$ alkyl)benzyl group;

R$_3$ is hydrogen, C$_1$-C$_{20}$ straight chain alkyl, phenyl(-C$_1$-C$_{20}$ straight chain alkyl or alkenyl of 1-6 unconjugated double bonds), cyclohexyl(C$_1$-C$_{20}$ straight chain alkyl or alkenyl having 1-6 unconjugated double bonds), phenyl, cyclohexyl or benzothienyl(-C$_1$-C$_{20}$ alkyl or alkenyl having 1-6 unconjugated double bonds), 4-methyl-3-pentenyl, 4-methyl-6-(2,6,6-trimethyl-cyclohex-1-enyl)hex-3-enyl, 1-(2-ethenyl)-1,5,9-trimethyl-deca-4,8-dienyl, Y-(CH$_2$)$_n$ or B-(straight chain C$_3$-C$_{14}$ alkynyl);

R$_4$ is hydrogen, bromo or chloro but is not bromo or chloro when R$_3$ contains a double bond;

n is 6-12;

Y is OR$_5$, CO$_2$R$_6$, t-butyl, t-butyldimethylsilyl, diphenylmethyl, triphenylmethyl, pyridyl, thienyl, quinolyl, N—C$_1$-C$_4$ alkylpyrrolyl, N—C$_1$-C$_4$ alkylpiperidyl, N—C$_1$-C$_4$ alkylpyridinium halide or naphthyl;

R$_5$ is hydrogen, C$_1$-C$_4$ alkyl or C$_1$-C$_4$ alkanoyl;

R$_6$ is hydrogen or C$_1$-C$_4$ alkyl;

B is hydrogen, phenyl, pyridyl or naphthyl;

and a lactone formed when R$_2$ is hydrogen and R$_3$ is (CH$_2$)$_{11-15}$COOH; said phenyl in the definition of R$_3$ being optionally substituted by C$_1$-C$_{14}$ alkyl, alkenyl, alkynyl or aryl, CO$_2$R$_6$, C$_1$-C$_4$ alkoxy or halo.

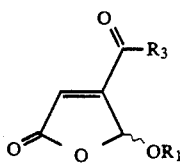

Formula 12

In Formula 12 R$_1$ is hydrogen or C$_1$-C$_{20}$ alkanoyl, and

R$_3$ is C$_5$-C$_{20}$ straight chain alkyl, benzothienyl(C$_1$-C$_{20}$ alkyl), 4-methyl-3-pentenyl, 4-methyl-6-(2,6,6-trimethylcyclohex-1-enyl)hex-3-enyl or 1-(2-ethenyl)-1,5,9-trimethyldeca-4,8-dienyl.

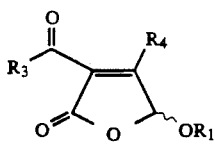

Formula 13

In Formula 13

R$_1$ is hydrogen, C$_1$-C$_4$ alkyl, benzyl, C$_1$-C$_{20}$ alkanoyl, cyclohexanoyl, benzoyl, pheny(C$_{1-4}$ alkanoyl) or naphthoyl;

R$_3$ is H, C$_1$-C$_{20}$ straight chain alkyl, phenyl(C$_1$-C$_{20}$ straight chain alkyl), cyclohexyl(C$_1$-C$_{20}$ straight chain alkyl), phenyl, cyclohexyl or benzothienyl(-C$_1$-C$_{20}$ alkyl), 4-methyl-3-pentenyl, 4-methyl-6-(2,6,6-trimethylcyclohex-1-enyl)hex-3-enyl, 1-(2-ethenyl)-1,5,9-trimethyldeca-4,8-dienyl, Y-(CH$_2$)$_n$ or B-(straight chain C$_3$-C$_{14}$ alkynyl);

R$_4$ is hydrogen, bromo, or chloro but is not bromo or chloro when R$_3$ contains a double bond;

n is 6-12;

Y is OR$_5$, CO$_2$R$_6$, t-butyl, t-butyldimethylsilyl, diphenylmethyl, triphenylmethyl, pyridyl, thienyl, quinolyl, N—C$_1$-C$_4$ alkylpyrrolyl, N—C$_1$-C$_4$ alkylpiperidyl, N—C$_1$-C$_4$ alkylpyridinium halide or naphthyl;

R$_5$ is hydrogen, C$_1$-C$_4$ alkyl or C$_1$-C$_4$ alkanoyl;

R$_6$ is hydrogen or C$_1$-C$_4$ alkyl;

B is hydrogen, phenyl, pyridyl or naphthyl.

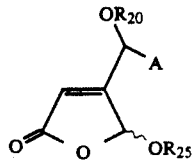

Formula 14

In Formula 14

R$_{20}$ is hydrogen, C$_1$-C$_{14}$ alkanoyl, COHNR$_{23}$ or CO$_2$R$_{24}$;

R$_{23}$ is phenyl or C$_1$-C$_4$ alkyl;

R$_{24}$ is C$_1$-C$_6$ alkyl;

A is CH$_2$O—R$_{21}$ or CH(C$_7$-C$_{14}$ alkyl); or OCOR$_{22}$ when R$_{20}$ is C$_1$-C$_{14}$ alkanoyl, A may be CH$_2$OCOR$_{22}$ or CH$_2$OP(O)(OR$_{22}$)R$_{22}$;

R$_{21}$ is C$_7$-C$_{14}$ alkanoyl, N—(C$_6$-C$_{14}$ alkyl) carbamoyl, naphthyl-(C$_1$-C$_6$ alkyl), pyridyl-(C$_1$-C$_6$ alkyl) or methoxyethoxymethyl;

R$_{22}$ is C$_1$-C$_4$ alkyl; and

R$_{25}$ is H, C$_{1-6}$ alkanoyl or C$_{1-6}$ alkyl.

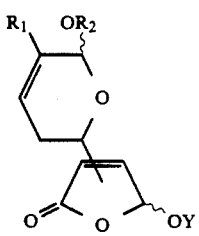

Formula 15

In Formula 15

R$_1$ is phenyl (C$_{1-17}$alkyl or alkenyl having 1-5 unconjugated double bonds), benzothienyl (C$_{1-17}$alkyl or alkenyl having 1-5 unconjugated double bonds);

R$_2$ is hydrogen or a C$_{1-4}$ alkyl group, and

Y is H, or C$_1$-C$_6$ alkanoyl.

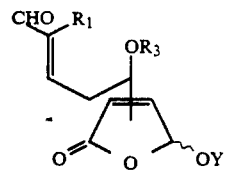

Formula 16

In Formula 16

R$_1$ is alkyl or alkenyl having 1-5 unconjugated double bonds, phenyl (C$_1$-C$_{17}$ alkyl or alkenyl having 1-5 unconjugated double bonds), benzothienyl (C$_{11-17}$ alkyl or alkenyl having 1-5 unconjugated double bonds), naphthyl (C$_1$-C$_{17}$ alkyl or alkenyl having 1-5 unconjugated double bonds), cyclohexyl or methyl;

R$_3$ is hydrogen or C$_1$-C$_4$ alkanoyl; and

Y is H or C$_1$-C$_6$ alkanoyl.

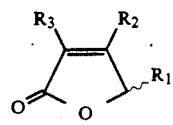

Formula 17

In Formula 17

R₁ is H, alkyl of 1 to 20 carbons, alkylene having one or more double bonds, alkyne having one or more triple bonds, arylalkyl, arylalkylene having one or more double bonds, or arylalkyne having one or more triple bonds;

R₂ is H, alkyl of 1 to 20 carbons, alkylene having one or more double bonds, alkyne having one or more triple bonds, arylalkyl, arylalkylene having one or more double bonds or arylalkyne having one or more triple bonds, and R₃ is H, alkyl of 1 to 20 carbons, arylalkyl, or halogene.

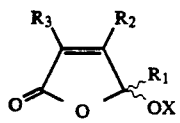

Formula 18

In Formula 18

R₁ is H, alkyl of 1 to 20 carbons, alkylene having one or more double bonds, alkyne having one or more triple bonds, arylalkyl, arylalkylene having one or more double bonds, or arylalkyne having one or more triple bonds;

R₂ is H, alkyl of 1 to 20 carbons, alkylene having one or more double bonds, alkyne having one or more triple bonds, arylalkylene having one or more double bonds or arylalkyne having one or more triple bonds;

R₃ is H, alkyl of 1 to 20 carbons, arylalkyl, or halogene, and

X is H or alkyl of 1 to 20 carbons, CO—X*, CO—O—X*,, CO—NH—X*,, or PO(OX*,)₂ or PO-(OX*,)X*,, where X*, independently is H, alkyl of 1 to 20 carbons, phenyl, or substituted phenyl, with the proviso that R₁ and R₃ both are not hydrogen.

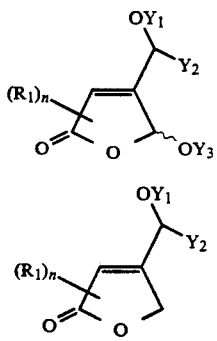

Formula 19a

Formula 19b

In Formula 19a and 19b

R₁ independently is H, phenyl, C₁-C₆ alkyl substituted phenyl, halogen substituted phenyl, or alkyl of 1 to 6 carbons and n is an integer having the values of 1 or 2, and where when n is 1 the R₁ group is attached to one of the 3 and the 5 positions of the 2-furanone, when n is 2 then the R₁ groups are attached to both the 3 and 5 positions with the proviso that when n is 1 then R₁ is not H;

Y₁ is H, alkyl of 1 to 20 carbons, phenyl C₁-C₂₀ alkyl, C₁-C₂₀ alkenyl containing one or more olephinic bonds, PO(OH)₂, PO(OH)OR₂, PO(OH)R₂, PO-(OR₂)₂, where R₂ is independently alkyl of 1 to 20 carbons, phenyl, or halogen substituted phenyl, or C₁-C₆ alkyl substituted phenyl, further Y₁ is CO—R₃, CO—OR₃, CONHR₃, SO₂R₃, SO₂NHR₃, (CH₂)ₚ—O—R₃, or (CH₂)ₚ—O—(CH₂)ₘ—O—R₃, where p, and m, are integers and are independently 1 to 20 and R₃ is H, C₁-C₂₀ alkyl, C₁-C₂₀ alkenyl containing one or more olephinic bonds, phenyl, halogen substituted phenyl, or C₁-C₆ alkyl substituted phenyl, with the proviso that when Y₁ is CO—R₃, CO—OR₃, and CONHR₃ then R₃ is not hydrogen;

Y₂ is an alkyl group of 6 to 25 carbons, phenyl, naphthyl, phenyl (C₁-C₂₀)alkyl-, naphthyl (C₁-C₂₀)alkyl-, C₁-C₆ alkyl substituted phenyl, halogen substituted naphthyl, C₁-C₆ substituted naphthyl, and Y₃ is H, alkyl of 1 to 20 carbons, CO—R₄, CO—O—R₄, CO—NH—R₄, PO(OR₄)₂ or PO(OR₄)R₄, where R₄ independently is H, alkyl of 1 to 20 carbons, phenyl, or halogen substituted phenyl, or C₁-C₆ alkyl substituted phenyl, with the proviso that when Y₃ is COOR₄ then R₄ is not H.

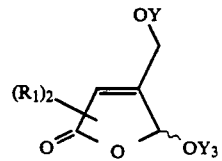

Formula 20a

Formula 20b

In Formula 20a and 20b

R₁ independently is phenyl or alkyl of 1 to 6 carbons, the R₁ groups being attached to the 3 and 5 positions of the 2-furanone;

Y₁ is CO—R₃, or CO—NHR₃ and R₃ is C₆-C₂₀ alkyl, and

Y₃ is H or CO—R₄ where R₄ is alkyl of 1 to 6 carbons.

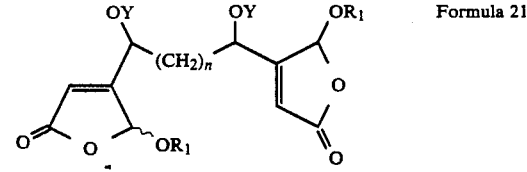

Formula 21

In Formula 21 R₁ is H, alkyl of 1 to 20 carbons, CO—R₂, CO—O—R₂, CO—NH—R₂, PO(OR₂)₂, or PO(OR₂)R₂, where R₂ independently is H, alkyl of 1 to 20 carbons, phenyl, lower alkyl substituted phenyl or halogen substituted phenyl;

n is an integer between 8 to 14;

Y is H, alkyl having 1-20 carbon atoms, carbocyclic aryl[lower alkyl], carbocyclic aryl, lower alkyl[carbocyclic aryl], alkenyl containing one or more olephinic bonds and 1-20 carbon atoms, CO—R₃, CO—OR₃, CONHR₃, SO₂R₃, or SO₂NHR₃ where R₃ is carbocyclic aryl[lower alkyl], carbocyclic aryl, lower alkyl[carbocyclic aryl], alkenyl containing one or more olephinic bonds and 1-20 carbon atoms, further Y is PO(OH)₂, PO(OH)OR₄, PO(OH)R₄, or PO(OR₄)₂, where R₄ is independently alkyl of 1-20 carbons or phenyl.

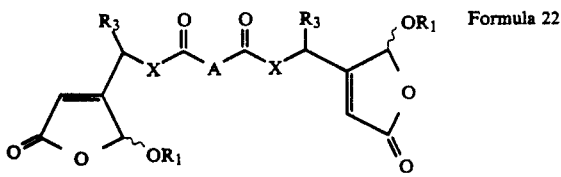

Formula 22

In Formula 22 $R_1$ independently is H or alkyl of 1 to 20 carbons, $CO-R_2$, $CO-O-R_2$, $CO-NH-R_2$, or $PO(OR_2)_2$ or $PO(OR_2)R_2$, where $R_2$ independently is H, alkyl of 1 to 20 carbons, phenyl, or lower alkyl substituted phenyl or halogen substituted phenyl;

A is $(CH_2)_n$ where n ranges between 0 to 30, or A is a divalent branch chained alkyl radical, or cycloalkyl radical, having a total of 3 to 30 carbons;

$R_3$ independently is an alkyl group having 4 to 20 carbons, and

X is O or NH.

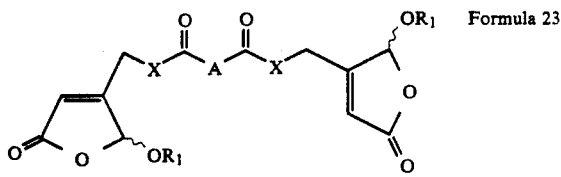

Formula 23

In Formula 23

$R_1$ independently is H or alkyl of 1 to 20 carbons, $CO-R_2$, $CO-O-R_2$, $CO-NH-R_2$, or $PO(OR_2)_2$ or $PO(OR_2)R_2$, where $R_2$ independently is H, alkyl of 1 to 20 carbons, phenyl, or lower alkyl substituted phenyl or halogen substituted phenyl;

A is $(CH_2)_n$ where n ranges between 5 to 30, or A is a divalent branch chained alkyl radical, or cycloalkyl radical, having a total of 5 to 30 carbons, and X is O or NH.

Pharmaceutically acceptable salts of the compounds shown by Formulae 1 through 23 can also be administered in accordance with the method of treatment of the present invention.

GENERAL EMBODIMENTS

Definitions

The terms "ester", "amine", "amide", "ether" and all other terms and terminology used here, (unless specifically defined in the present description) refer to and cover any compounds falling within the respective term as that term is classically used in organic chemistry.

Unless specifically noted otherwise, preferred esters are derived from the saturated aliphatic alcohols or acids of ten or fewer carbon atoms or from the cyclic or saturated aliphatic cyclic alcohols and acids of 5 to 10 carbon atoms. Particularly preferred aliphatic esters are those derived from lower alkyl acids or alcohols. Also preferred are the phenyl or lower alkylphenyl esters.

The term "alkyl" as used in the present description and claims includes straight chain alkyl groups, branched chain alkyl groups, cycloalkyl groups, alkyl substituted cycloalkyl groups, and cycloalkyl substituted alkyl groups. Unless the number of carbons is otherwise specified, "lower alkyl" means the former broad definition of "alkyl" groups but with the restriction that the group has 1 to 6 carbon atoms.

Unless specifically noted otherwise, the term "long chain alkyl" also means the former broad definition of "alkyl" groups but with the restriction that the group has no less than 4 carbon atoms, and no more than approximately 25 carbon atoms.

Unless specifically noted otherwise, preferred amides are the mono- and di-substituted amides derived from the saturated aliphatic radicals of ten or fewer carbon atoms, or the cyclic or saturated aliphatic-cyclic radicals of 5 to 10 carbon atoms.

Some of the compounds utilized in the method and pharmaceutical composition of the invention may contain one or more chiral centers. Accordingly, these compounds may be prepared as mixtures of enantiomeric compounds (where the enatiomers may or may not be present in equal amounts) or as optically pure enantiomers. When there is more than one chiral center, the compounds may also be prepared as mixtures of diastereomers, or as pure diastereomers, and each diastereomer itself may be a mixture of enantiomers in 1:1, or other, ratios. Alternatively, each diastereomeric compound may be sterically and optically pure. However, all of the above-noted forms, including optically pure enantiomers and mixtures thereof, as well as all diastereomers, are within scope of the present invention.

Some of the compounds utilized in the method and pharmaceutical composition of the invention may have cis and trans stereoisomers. The scope of the invention includes the use of both pure stereoisomers as well as mixtures thereof.

A pharmaceutically acceptable salt of any compound shown by Formulae 1-23 may be prepared and used in the method of the present invention provided the compound has a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The compounds shown by Formulae 1-23 (or their pharmaceutically acceptable salts) are utilized, in accordance with the present invention, for treating animals of the mammalian species (including humans) for the purpose of modifying the balance between bone production and resorption, namely for the purpose of inhibiting or decreasing the rate of undesirable bone loss. Osteoporosis is a disease which is characterized by undesirable bone loss. Thus, the compounds shown by Formulae 1-23 (or their pharmaceutically acceptable salts) can be used, in accordance with the present invention, for treating osteoporosis.

The capacity of the compounds utilized in the method of the present invention to modify the balance of bone production and bone resorption, can be evaluated essentially as is described by G. Eilon and 1. G. Raisz: "Comparison of the effects of stimulators and inhibitors of resorption on the release of lysosomal enzymes and radioactive calcium from fetal bone in organ culture" Endocrinology 103: 1969–1975 (1978). For further description of assay procedures suitable for evaluating inhibition of bone loss by the compounds utilized in accordance with the present invention, reference is made to U.S. Pat. No. 4,916,241 (and particularly to Column 8 line 34 through Column 9 line 56 thereof), and the specification of U.S. Pat. No. 4,916,241 is expressly incorporated herein by reference.

The biologically active compounds shown by Formulae 1–23 are administered in accordance with the present invention to mammals, including humans, in an effective amount to produce the desired activity, preferably in an amount of about 0.05 to 100 mg per day per kilogram of body weight. The nature of the host animal, (or person) age, weight and condition and extent of symptoms, as well as the identity of the compound used, is likely to affect the actual daily dose, which may be a single dose, or the compound (or a pharmaceutically acceptable salt thereof) may be administered in multiple doses. Generally speaking, treatment in accordance with the invention may be initiated with a small dosage, and the dosage may be thereafter increased gradually until the desired effect, or the optimum effect attainable under the circumstances, is obtained.

The compounds are admistered in the method of treatment of the invention in a pharmaceutical composition adapted for standard routes of administration. Such pharmaceutical compositions comprise the active compounds as well as pharmaceutical carriers suitable for the route of administration. Standard methods for formulating pharmaceutical compositions of this type may be found in *Remington's Pharmaceutical Sciences*, Mack Publishing Company, Easton, Pa.

Although several routes of administration of the compounds of the invention can be used, the preferred routes of administration are oral and parental.

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
| --- | --- |
| Lactose, spray-dried | 40–99 |
| Magnesium stearate | 1–2 |
| Cornstarch | 10–20 |
| Active ingredient | 0.001–20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The active compounds used in the method of treatment of this invention, may be combined with other known agents and drugs in the pharmaceutical compositions and methods described herein.

SPECIFIC EXAMPLES

The preferred compounds for use in the process of the present invention are disclosed in connection with the herein described examples. The synthetic processes for preparing the compounds utilized in the method of treatment of the present invention are also disclosed in connection with the specific examples. Generally speaking, and with respect to the 4-substituted 5-hydroxy 2(5H)-furanone derivatives utilized in the method of the present invention, the process of their preparation includes a step where a 2-trialkylsilylfuran intermediate, which has the side chain in the 4 position of the furan nucleus that is desired for biological activity, is subjected to oxidation by singlet oxygen to provide the biologically active 4-substituted 5-hydroxy-2-(5H)-furanone. The conditions of the reactions with singlet oxygen are described in detail in connection with several specific examples. In general terms, these oxidation reactions are preferably conducted in a mixture of water and acetone or in a mixture of water and tetrahydrofuran, and in some instances in substantially neat tetrahydrofuran, in the presence of an initiator, preferably Rose Bengal dye (preferably polymer bounded), which is added to the reaction mixture. The reaction mixture and vessel is flushed with oxygen and the reaction is conducted at low temperature, at approximately $-78°$ C., or for the herein described reactions preferably at approximately $0°$ C., under a constant positive pressure of oxygen for a number of hours, typically 1 to 7 hours. The mixture is typically irradiated with a 150 Watt flood lamp. Work-up of the reaction mixture after irradiation usually includes concentration by evaporation of the solvent, followed by chromatography on silica gel, in columns or on preparative silica plates.

EXAMPLE 1

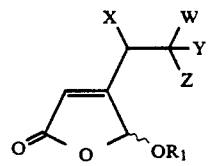

Formula 1

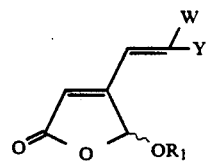

Formula 2

The compounds which are preferred in the method of treatment of the present invention and which are designated by Formula 1 and Formula 2 above, have the following preferred structural features.

With respect to the 5-position of the furanone moiety, those compounds of Formula 1 and Formula 2 are preferred where the substituent is hydroxy or acetoxy ($R_1$ is H or $CH_3CO$).

With respect to the Z substituent on the beta carbon in the side chain (in the 4-position) of the furanone moiety (Formula 1), the preferred compounds are those where Z is hydrogen.

With respect to the W substituent on the beta carbon of the side chain in the 4-position of the furanone molecule, the preferred compounds are those where W is hydrogen, or is COOR$_4$ (R$_4$ defined as in Formula 1), preferably R$_4$ is methyl.

With respect to the X substituent on the alpha carbon of the side chain in the 4-position of the furanone molecule, the preferred compounds are those where X is long chain alkyl of more than 8 carbons, or X is 5-(phenyl)pentyl, or a derivative substituted in the phenyl ring. Particularly preferred in this regard are compounds where X is CH$_3$(CH$_2$)$_{11}$, and compounds where X is 5-(2,4,5-trifluorophenyl)pentyl.

With respect to the Y substituent on the beta carbon of the side chain in the 4-position of the furanone molecule, the preferred compounds are those where Y is COOH, COOR$_2$, CONH$_2$ with R$_2$ in these ester preferably being lower alkyl, most preferably methyl or ethyl. Compounds are also preferred where Y is COR$_2$, COCF$_3$, COCF$_2$H, with R$_2$ preferably being methyl in these ketone compounds. Still further, compounds are preferred where Y is CH=NOH, or CH=NOR$_2$ (aldoximes), CR$_2$=NOH, CR$_2$=NOR$_2$ (ketoximes) and CH=N—NHR$_2$ (hydrazones) with R$_2$ preferably being methyl in these oxime or hydrazone compounds. Other preferred compounds are where Y is C(R$_2$)$_2$OH (tertiary alcohols, with R$_2$ preferably being methyl) and where Y is PO(OR$_3$)$_2$, PS(OR$_3$)$_2$, SO$_2$R$_2$ (phosphonyl, thiophosphonyl and sulphonyl compounds). The sulphonyl compounds are particularly preferred where R$_2$ is methyl, and phosphonyl compounds are particularly preferred where R$_3$ is ethyl.

The most preferred compounds of this example, used in accordance with the method of treatment of the invention are those listed just below with reference to Formula 24 or Formula 25:

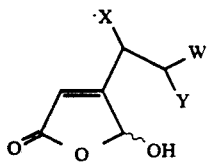
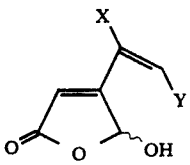

Formula 24       Formula 25

Formula 24, Compound 1: W=H, X=CH$_3$—(CH$_2$)$_{11}$ and Y=CO$_2$CH$_2$CH$_3$;
Formula 24, Compound 2: W=H, X=CH$_3$—(CH$_2$)$_{11}$ and Y=COCH$_3$;
Formula 24, Compound 3: W=H, X=CH$_3$—(CH$_2$)$_{11}$ and Y=COCF$_3$;
Formula 24, Compound 4: W=H, X=CH$_3$—(CH$_2$)$_{11}$ and Y=C(CH$_3$)$_2$OH;
Formula 24, Compound 5: W==CO$_2$CH$_3$, X=CH$_3$—(CH$_2$)$_{11}$ and Y=CO$_2$CH$_3$;
Formula 24, Compound 6: W=H, X=CH$_3$—(CH$_2$)$_{11}$ and Y=COOH;
Formula 24, Compound 7: W=H, X=CH$_3$—(CH$_2$)$_{11}$ and Y=PO(OCH$_2$CH$_3$)$_2$;
Formula 24, Compound 8: W=H, X=5—(2,4,5-trifluorophenyl)pentyl and Y=COCF$_3$;
Formula 24, Compound 9: W=H, X=CH$_3$—(CH$_2$)$_{11}$ and Y=CH=NOCH$_3$;
Formula 24, Compound 10: W=H, X=CH$_3$—(CH$_2$)$_{11}$ and Y=CONH$_2$;
Formula 24, Compound 11: W=H, X=CH$_3$—(CH$_2$)$_{11}$ and Y=CH=NOH;
Formula 24, Compound 12: W=H, X=CH$_3$—(CH$_2$)$_{11}$ and Y=CH=NNHCH$_3$;
Formula 24, Compound 13: W=H, X=CH$_3$—(CH$_2$)$_{11}$ and Y=COCF$_2$H;
Formula 24, Compound 14: W=H, X=CH$_3$—(CH$_2$)$_{11}$ and Y=PS(OCH$_2$CH$_3$)$_2$;
Formula 24, Compound 15: W=H, X=CH$_3$—(CH$_2$)$_{11}$ and Y=SO$_2$CH$_3$;
Formula 24, Compound 16: W=H, X=CH$_3$—(CH$_2$)$_{11}$ and Y=CCH$_3$=NOH;
Formula 25, Compound 17: X=CH$_3$—(CH$_2$)$_{11}$ and Y=COCF$_3$, and
Formula 25, Compound 18: X=CH$_3$—(CH$_2$)$_{11}$ and Y=PO(OCH$_2$CH$_3$)$_2$;

The compounds corresponding to Formula 1, 2, including the preferred compounds identified above in connection with Formula 24 and Formula 25 can be prepared in accordance with the disclosure of U.S. Pat. No. 5,013,850, the specification of which is expressly incorporated herein by reference.

EXAMPLE 2

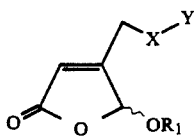

Formula 3

The compounds which are preferred in the method of treatment of the present invention and which are designated by Formula 3 above, have the following preferred structural features.

The preferred compounds with reference to Formula 3 and with respect to the 5-position of the furanone moiety are those where the substituent is hydroxy, acetoxy or alkanoyloxy derived from an alkanoic acid including a long chain alkyl group (R$_1$ is H, CH$_3$CO, or is CO—R$_1$* where R$_1$* is long chain alkyl). Particularly preferred in this regard are the compounds where CO—R$_1$* is n-dodecanoyl.

With respect to the X substituent in the side chain in the 4-position of the 5-hydroxy-2(5H)-furanone molecule, the preferred compounds are those where X is O, S, NH, SO, and SO$_2$.

With respect to the Y substituent in the side chain in the 4-position of the 5-hydroxy-2(5H)-furanone molecule, the preferred compounds used in the method of the invention are those where Y is long chain alkyl, particularly where the alkyl group is straight chained and has more than 10 carbons; the n-dodecyl group is especially preferred in this regard. Compounds are also preferred where Y is (CH$_2$)$_n$—O—(CH$_2$)$_m$—O—R$_4$, particularly where n is 1, m is 2, and R$_4$ is methyl. Further with respect to the substituent group Y, compounds are preferred where Y is CO—R$_3$, CO—OR$_3$, CONHR$_3$, SO$_2$R$_3$, SO$_2$NHR$_3$ and where R$_3$ is long chain alkyl, particularly straight chained long chain alkyl, most preferably where R$_3$ is n-dodecyl. Alternatively, compounds are preferred in the latter category where R$_3$ is phenyl substituted straight chain alkyl of at least 4 carbons (or substituted phenyl substituted straight chain alkyl of at least 4 carbons); in certain particularly preferred embodiments of the invention Y is CO—R$_3$ with R$_3$ being 5-(4-methoxyphenyl)-n-pentyl. Still further, compounds are preferred within the scope of the present invention where Y is PO(OH)$_2$, PO(OH)R$_5$, where R$_5$ is long chain alkyl, preferably long chain n-alkyl, most preferably n-dodecyl, or Y is PO(OR$_5$)$_2$, where R$_5$ is lower alkyl, most preferably ethyl, and still further where Y is PO(OH)O(CH$_2$)$_n$—N$^+$(R$_5$*)$_3$ particularly where n is 2 and where R$_5$* is methyl.

Examples of preferred compounds in accordance with Formula 3 are as follows:

| Compound 20: | X = O | R$_1$ = H | Y = CH$_2$O(CH$_2$)$_2$OCH$_3$; |
|---|---|---|---|
| Compound 21: | X = O | R$_1$ = H | Y = PO(OH)(CH$_2$)$_{11}$CH$_3$; |
| Compound 22: | X = O | R$_1$ = H | Y = CONH(CH$_2$)$_{11}$CH$_3$; |
| Compound 23: | X = O | R$_1$ = H | Y = (CH$_2$)$_{11}$CH$_3$; |
| Compound 24: | X = NH | R$_1$ = H | Y = CO(CH$_2$)$_{11}$CH$_3$; |
| Compound 25: | X = NH | R$_1$ = H | Y = CONH(CH$_2$)$_{11}$CH$_3$; |
| Compound 26: | X = NH | R$_1$ = H | Y = SO$_2$(CH$_2$)$_{11}$CH$_3$; |
| Compound 27: | X = S | R$_1$ = H | Y = (CH$_2$)$_{11}$CH$_3$; |
| Compound 28: | X = SO | R$_1$ = H | Y = (CH$_2$)$_{11}$CH$_3$; |
| Compound 29: | X = O | R$_1$ = H | Y = PO(OCH$_2$CH$_3$)$_2$; |
| Compound 30: | X = O | R$_1$ = CO(CH$_2$)$_{10}$CH$_3$ | Y = PO(OCH$_2$CH$_3$)$_2$; |
| Compound 31: | X = O | R$_1$ = H | Y = POO$^-$O(CH$_2$)$_2$N$^+$(CH$_3$)$_3$; |
| Compound 32: | X = NH | R$_1$ = H | Y = COO(CH$_2$)$_{11}$CH$_3$; |
| Compound 33: | X = NH | R$_1$ = H | Y = PO(OH)(CH$_2$)$_{11}$CH$_3$; |
| Compound 34: | X = SO$_2$ | R$_1$ = H | Y = (CH$_2$)$_{11}$CH$_3$; |
| Compound 35: | X = O | R$_1$ = H | Y = CO(CH$_2$)$_5$-(4-methoxy)phenyl; |
| Compound 36: | X = NH | R = H | Y = SO$_2$NH(CH$_2$)$_{11}$CH$_3$; |
| Compound 37: | X = O | R = CO(CH$_2$)$_{10}$CH$_3$ | Y = PO(OH)$_2$. |

The compounds corresponding to Formula 3, including the preferred compounds identified in connection therewith can be prepared in accordance with the disclosure of U.S. Pat. No. 5,037,811, the specification of which is expressly incorporated herein by reference.

EXAMPLE 3

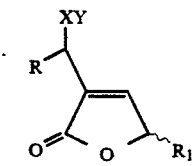

Formula 4

The compounds which are preferred in the method of treatment of the present invention and which are designated by Formula 4 above, have the following preferred structural features.

The preferred compounds utilized in accordance with the present invention, with reference to Formula 4 and with respect to R substituent are those where R is alkyl, preferably long chain alkyl, and even more preferably long chain n alkyl.

With respect to the substituent group X on the alpha carbon of the side chain in the 3-position of the 2(5H)-furanone moiety, the preferred compounds are those where X is O or NH.

With respect to the Y substituent on the hydroxyl or amino function in the side chain in the 3-position of the 2(5H)-furanone moiety, compounds are preferred where Y is H, acyl particularly acetyl. Also preferred are carbamates (where Y is CONHR$_3$) particularly where Y is CONHC$_6$H$_5$, and carbonates (where Y is COOR$_3$) particularly where R$_3$ is lower alkyl, still more preferably ethyl. Compounds are also preferred where Y is PO(OR$_2$)$_2$ particularly where R$_2$ is lower alkyl, still more preferably ethyl. Other preferred compounds, with respect to the substituent Y, are those where Y is SO$_2$R$_3$ or (CH$_2$)$_n$—O—(CH$_2$)$_m$—O—R$_3$, more preferably where R$_3$ is lower alkyl, still more preferably methyl.

The most preferred compounds corresponding to this example are those listed below with reference to Formula 26:

| Compound 40: | X = O | n = 7 | Y = CH$_3$CO; |
|---|---|---|---|
| Compound 41: | X = O | n = 11 | Y = H; |

| Compound 42: | X = O | n = 11 | Y = CH$_3$CO; |
|---|---|---|---|
| Compound 43: | X = O | n = 11 | Y = CONHC$_6$H$_5$; |
| Compound 44: | X = O | n = 11 | Y = COOC$_2$H$_5$; |
| Compound 45: | X = NH | n = 11 | Y = COCH$_3$; |
| Compound 46: | X = NH | n = 11 | Y = SO$_2$CH$_3$. |

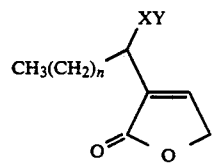

Formula 26

The compounds corresponding to Formula 4, including the preferred compounds identified in connection therewith and shown by Formula 26 can be prepared in accordance with the disclosure of U.S. Pat. No. 5,043,457, the specification of which is expressly incorporated herein by reference.

EXAMPLE 4

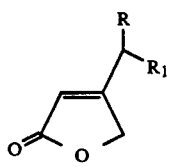

Formula 5

The compounds which are preferred in the method of treatment of the present invention and which are designated by Formula 5 above, have the following preferred structural features. R is preferably alkyl of 7 to 20 carbons and R$_1$ is preferably OCOR$_2$ where R$_2$ is alkyl of 1 to 14 carbons. Alternatively R is 2-(methoxy)ethoxymethoxymethyl and R$_1$ is OCO—(C$_7$-C$_{14}$ alkyl).

The most preferred compounds of this example are: 4-[1-dodecanoyloxy-2-(2-methoxyethoxy)methoxymethyl]-2(5H)-furanone (Compound 50), 4-(1-acetoxytridecyl)-2(5H)-furanone (Compound 51), 4-[((R)-(+)-

α-methylbenzylcarbamyloxy)tridecyl]-2(5H)-furanone (Compound 52), and 4-(1-hydroxytridecyl)-2(5H)-furanone (Compound 53).

The compounds corresponding to Formula 5, including the preferred compounds identified in connection therewith can be prepared in accordance with the disclosure of U.S. Pat. No. 5,045,564, the specification of which is expressly incorporated herein by reference.

EXAMPLE 5

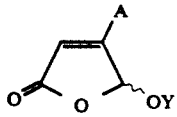

Formula 6

Examples of compounds which are preferred in the method of treatment of the present invention and which are designated by Formula 6 above, are as follows: 4-(5-oxo-3-hexadecenyl)-5-hydroxy-2(5H)-furanone (Compound 60), 4-(3-dodecanoyloxypropyl)-5-hydroxy-2(5H)-furanone (Compound 61), 4-(2-carbomethoxytridecyl)-5-hydroxy-2(5H)-furanone (Compound 62), and 4-(2-carbooctanoxyethyl)-5-hydroxy-2(5H)-furanone (Compound 63).

The compounds corresponding to Formula 6, including the preferred compounds identified in connection therewith can be prepared in accordance with the disclosure of U.S. Pat. No. 5,059,611, the specification of which is expressly incorporated herein by reference.

EXAMPLE 6

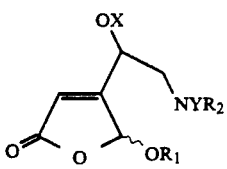

Formula 7

The compounds which are preferred in the method of treatment of the present invention and which are designated by Formula 7 above, have the following preferred structural features. With respect to the 5-position of the furanone moiety, those compounds are preferred where the substituent is hydroxy or acetoxy ($R_1$ is H or $CH_3CO$).

With respect to the nitrogen on the beta carbon in the side chain (in the 4-position) of the furanone moiety, the preferred compounds used in the method of treatment of the invention are those where $R_2$ is hydrogen.

With respect to the alpha hydroxyl function in the side chain (in the 4-position) of the furan moiety, preferred compounds are where: the hydroxyl is unsubstituted (X=H), is esterified with an acid having the structure $R_3$—COOH, ($R_3$ is defined as for Formula 7), the hydroxyl is converted into a carbonate (X=CO—O—$R_3$) or carbamate (X=CO—NH—$R_3$). Particularly preferred in regard to this alpha hydroxyl function are acetate and propionate esters (X=COCH$_3$ or X=COCH$_2$CH$_3$), esters of long chain fatty acids such as dodecanoic acid (X=CO(CH$_2$)$_{10}$CH$_3$), esters of alpha-omega dicarboxylic acids, such as glutaric acid, or esters of long chain dicarboxylic acids (e.g. X=CO(CH$_2$)$_3$COOH or (X=CO(CH$_2$)$_{10}$COOH), carbonates where X=CO—O—$R_3$ and $R_3$ is alkyl, especially ethyl, carbamates where X=CO—NH—$R_3$ and $R_3$ is phenyl or alkyl.

With respect to the amino function in the side chain (in the 4-position) of the furan moiety, (Formula 7) preferred compounds are: alkyl sulfonamides (Y=—SO$_2$R$_4$) particularly where the alkyl group ($R_4$) is methyl or alkyl of 6 to 20 carbons; carboxamides (Y=CO— $R_4$) formed from alkanoic acids, dialkylamino-substituted carboxamides derived from omega dialkylamino-substituted alkanoic acids (Y=CO—$R_4$ and $R_4$ is, for example, (CH$_3$)$_2$N(CH$_2$)$_3$), carboxamides derived from benzoic acid or substituted benzoic acid, including carboxamides derived from carboxy substituted benzoic acids (e.g. Y=CO—$R_4$ and $R_4$ is C$_6$H$_3$(COOH)$_2$), carboxamides derived from alpha-omega dicarboxylic acids (Y=CO—(CH$_2$)$_n$COOH, for example n is 3 or 10); alkyl phosphonates particularly where Y is PO(OR$_4$)R$_4$ ($R_4$ is alkyl, particularly lower alkyl); alkyl carbamates (Y=CO—O—$R_4$) particularly where the alkyl group $R_4$ has 6 to 20 carbons); and urea derivatives (Y=CO—NH—$R_4$ or Y=CO—N—($R_4$)$_2$) particularly in the former case where $R_4$ is alkyl of 6 to 20 carbons, or in the latter case $R_4$ is ethyl. Also preferred are urea derivatives where Y is CO-N-methylpiperazinyl, methylsulfon-substituted N-piperazinyl, or N-morpholinyl group.

Examples of preferred compounds in accordance with Formula 7 are as follows: 4-(2-undecanylamido-1-hydroxy)ethyl-5-hydroxy-2(5H)-furanone (Compound 70), 4-(1-acetoxy-2-undecanylamido)ethyl-5-hydroxy-2(5H)-furanone (Compound 71), 4-(2-undecanylamido-1-dodecanoyloxy)ethyl-5-hydroxy-2(5H)-furanone (Compound 72), 4-[1-acetoxy-2-(dodecanesulfonylamido)ethyl]-5-hydroxy-2(5H)-furanone (Compound 73), 4-[1-dodecanoyloxy-2-(3-carboxypropaneamido)]ethyl-5-hydroxy-2(5H)-furanone (Compound 74), 4-[(1-hydroxy-2-(10-carboxydecaneamido)-]ethyl-5-hydroxy-2(5H)-furanone (Compound 75), 4-[(1-acetoxy-2-(10-carboxydecaneamido)]ethyl-5-hydroxy-2(5H)-furanone (Compound 76), 4-[1-dodecanoyloxy-2-(N'-methanesulfonyl-piperazine)amido]ethyl-5-hydroxy-2(5H)-furanone (Compound 77), 4-[1-dodecanoyloxy-2-(N',N'-diethyl)-carboxyamido]ethyl-5-hydroxy-2(5H)-furanone (Compound 78).

The compounds corresponding to Formula 7, including the preferred compounds identified in connection therewith can be prepared in accordance with the disclosure of U.S. Pat. No. 5,081,147, the specification of which is expressly incorporated herein by reference

EXAMPLE 7

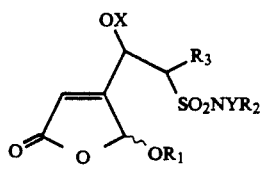 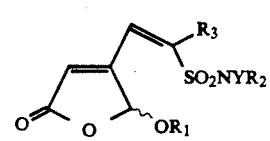

Formula 8        Formula 9

The compounds which are preferred in the method of treatment of the present invention and which are designated by Formula 8 and Formula 9 above, have the following preferred structural features. With respect to the 5-position of the furanone moiety, those compounds are preferred where the substituent is hydroxy or acetoxy ($R_1$ is H or $CH_3CO$).

With respect to the $R_3$ substituent on the beta carbon in the side chain (in the 4-position) of the furanone moiety, the preferred compounds are those where $R_3$ is hydrogen.

With respect to the $R_2$ substituent on the sulfonamide nitrogen, the preferred compounds are those where $R_2$ is hydrogen, or where $R_2$ and Y jointly comprise a heterocycle which incorporates the sulfonamide nitrogen as a heteroatom. In addition to mono-substituted sulfonamides ($R_2=H$) further preferred compounds in this regard are those where $R_2$, Y and the sulfonamide nitrogen jointly comprise a piperazine ring.

With respect to the Y substituent on the sulfonamide nitrogen, the preferred compounds are those where Y is alkyl, more preferably straight chain alkyl, and still more preferably "long chain" alkyl, for example of 7 to 20 carbon atoms. Also preferred are compounds where Y is straight chain alkyl substituted with a terminal OH, , dialkylamino, carboxy, or with a phosphate-oxy group (in Formula 8 and in Formula 9 Y is alkyl substituted with OH, $N(R_5^*)_2$ groups, or Y is alkyl substituted with $COR_5$ group where $R_5$ is OH, or Y is alkyl substituted with $O-PO(OR_5)_2$ group where $R_5$ is alkyl or hydroxyl Also preferred are compounds where Y is substituted phenyl, more preferably carboxy substituted phenyl.

Still with reference to Formula 8 and Formula 9, as applicable, and with respect to the X substituent on the alpha hydroxyl function in the side chain of the furanone molecule, the preferred compounds used in the method of the invention are those where X is hydrogen, or an acyl group, preferably an acyl group derived from an alkanoic acid having a straight alkyl chain, or an acyl group derived from a straight chain alpha, omega dicarboxylic acid. Still more specifically in this regard, compounds are more preferred where X is $COCH_3$, $CO(CH_2)_{10}CH_3$, or $CO(CH_2)_3COOH$. Compounds are also preferred where the alpha hydroxyl function is converted into a carbamate, more preferably into a phenylcarbamate, derivative (X is $CONHC_6H_5$. Examples of preferred compounds used in the method of treatment of the invention are those listed just below with reference to Formula 27 and Formula 28, or by full chemical name:

Compound 80: 4-[2-(N-dodecylsulfonamido)]-2-ethenyl-5-hydroxy-2(5H)-furanone;
Formula 27, Compound 81: $R_6=H$, $R_7=CH_3(CH_2)_{11}$;
Formula 27, Compound 82: $R_6=COCH_3$, $R_7=CH_3(CH_2)_{11}$;
Formula 27, Compound 83; $R_6=CO(CH_2)_3COOH$, $R_7=CH_3(CH_2)_{11}$;
Formula 27, Compound 84: $R_6=CO(CH_2)_{10}CH_3$, $R_7=(CH_2)_3OH$;
Formula 27, Compound 85: $R_6=CO(CH_2)_{10}CH_3$, $R_7=(CH_2)_2COOH$;
Formula 27, Compound 86: $R_6=CO(CH_2)_{10}CH_3$, $R_7=(CH_2)_3OPO(OEt)_2$;
Formula 27, Compound 87: $R_6=CO(CH_2)_{10}CH_3$, $R_7=(CH_2)_3OPO(OH)_2$;
Formula 27, Compound 88: $R_6=CO(CH_2)_{10}CH_3$, $R_7=(CH_2)_2N(CH_3)_2$;
Formula 27, Compound 89: $R_6=CO(CH_2)_{10}CH_3$, $R_7=$ paracarboxyphenyl ($C_6H_4COOH$);
Formula 28, Compound 90: $R_6=H$, $R_8=CH_3$;
Formula 28, Compound 91: $R_6=CO(CH_2)_{10}CH_3$, $R_8=CH_3$;
Formula 28, Compound 92: $R_6=CO(CH_2)_{10}CH_3$, $R_8=CH_3$, salt with $CH_3I$ (quaternary amine);
Formula 28, Compound 93: $R_6=CONHC_6H_5$, $R_8=CH_3$.

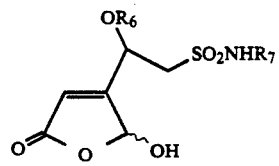

Formula 27

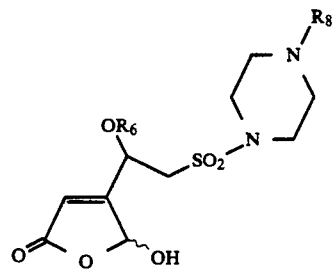

Formula 28

The compounds corresponding to Formula 8 and to Formula 9, including the preferred compounds identified in connection therewith and shown in Formula 27 and Formula 28 can be prepared in accordance with the disclosure of U.S. Pat. No. 5,081,261, the specification of which is expressly incorporated herein by reference.

EXAMPLE 8

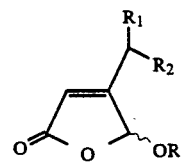

Formula 10

The compounds which are preferred in the method of treatment of the present invention and which are designated by Formula 10 above, have the following preferred structural features. R is preferably $C_1-C_6$ carbamoyl, phenylcarbamoyl, $C_1-C_6$ dialkyl phosphonate or $PO(OH)_2$. $R_1$ is preferably chloro, acetamido, methoxycarbonylamino, sulfonamide, 4-carboxybutanoyloxy, 4-carbomethoxybutanoyloxy, 2-methoxyethoxymethoxy, ethoxycarbonyloxy, 4-bromobutanoyloxy or 4-iodobutanoyloxy. $R_2$ is preferably $C_8-C_{20}$ alkyl.

Examples of preferred compounds in accordance with Formula 10 are as follows: 4-(1-thioacetoxytridecyl)-5-hydroxy-2(5H)-furanone (Compound 100); 4 - [1-(glutarylamido)-tridecyl]-5-hydroxy-2(5H)-furanone (Compound 101); 4-[1-(N-methylcarbamoyl)-N-methyl)carbamoyl]tridecyl-5-hydroxy-(5H)furanone (Compound 102); 4-[(1-phenylcarbamoyl)tridecyl]-5-hydroxy-2(5H)-furanone (Compound 103); 4-[1-ethoxycarbonyloxy)-tridecyl]-5-hydroxy-2(5H)-furanone Compound 104); 4-[1-(4-carboxybutanoyloxy)tridecyl]-5-hydroxy-2(5H)-furanone (Compound 105); 4-[1-4-carbomethoxybutanoyloxy)tridecyl]-5-hydroxy-2(5H)-furanone (Compound 106); 4-[1-(2-methoxyethoxy)methoxytridecyl]-5-hydroxy-2(5H)-furanone; 4-[1-(methylsulfonamido)-tridecyl]-5-hydroxy-(5H)-furanone (Compound 107); 4-(1-(methoxycarbonylamino)-tridecyl]-5-hydroxy-2(5H)-furanone (Compound 108);

4-[1-(4-bromobutanoyloxy)tridecyl]-5-hydroxy-2(5H)-furanone (Compound 109), and 4-[1-PO(OCH$_3$)CH$_3$O-tridecyl]5-hydroxy-2(5H)-furanone (Compound 110).

The compounds corresponding to Formula 10, including the preferred compounds identified in connection therewith can be prepared in accordance with the disclosure of U.S. Pat. No. 5,089,485, the specification of which is expressly incorporated herein by reference.

EXAMPLE 9

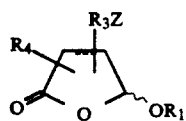

Formula 11

The compounds which are preferred in the method of treatment of the present invention and which are designated by Formula 11 above, have the following preferred structural features. With respect to the dotted line in Formula 11, it preferably represents a single bond. The $R_1$ group is preferably hydrogen or $C_1$–$C_{20}$ alkanoyl. The $R_3$—Z group is preferably in the 4-position of the furanone ring. The $R_2$ group is preferably hydrogen or $C_1$–$C_{20}$ alkanoyl. The $R_3$ group is preferably hydrogen, $C_1$–$C_{20}$ straight chain alkyl, phenyl($C_1$–$C_{20}$ straight chain alkyl), cyclohexyl($C_1$–$C_{20}$ straight chain alkyl), phenyl, cyclohexyl or benzothienyl($C_1$–$C_{20}$ alkyl), 4-methyl-3-pentenyl, 4-methyl-6-(2,6,6-trimethylcyclohex-1-enyl)hex-3-enyl, 1-(2-ethenyl)-1,5,9-trimethyldeca-4,8-dienyl, Y—(CH$_2$)$_n$ or B-(straight chain $C_3$–$C_{14}$ alkynyl). Examples of preferred compounds used in the method of treatment of the present invention and corresponding to Formula 11 are as follows: 4-(1-acetoxy-7-benzo(b)thien-2-yl-heptyl]-5-hydroxy-2(5H)-furanone (Compound 120); 4-(1-hydroxy-tridecyl)-5-hydroxy-2(5H)-furanone (Compound 121): 4-(1-acetoxy-tridecyl)-5-hydroxy-2(5H)-furanone (Compound 122); 4-(1-acetoxy-6-phenylhexyl)-5-hydroxy-2(5H)-furanone (Compound 123); 4-(1-acetoxy-6-(2-naphtyl)hexyl)-5-hydroxy-2(5H)-furanone (Compound 124); 4-(1-(α-methylbenzylcarbamoyl)-tridecyl)-5-hydroxy-2(5H)-furanone (Compound 125), and 4-[1-acetoxy-5-methyl-7-(2,6,6-trimethylcyclohex-1-enyl)-hept-4-e (Compound 126).

The compounds Which are shown by Formula 11, including the preferred compounds identified in connection therewith can be prepared in accordance with the disclosure of application Ser. No. 07/699,819, assigned to the same assignee as the present application, which has been allowed. The specification of this allowed application is expressly incorporated herein by reference.

EXAMPLE 10

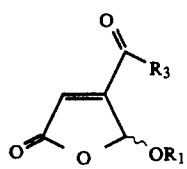

Formula 12

5-hydroxy-4-(1-keto)undecyl-2(5H)-furanone (Compound 130), is an example of a compound in accordance with Formula 12 which is preferred in accordance with the method of treatment of the present invention. This compound can be prepared in accordance with the disclosure of application Ser. No. 07/699,819, assigned to the same assignee as the present application, which has been allowed. The specification of this allowed application is expressly incorporated herein by reference.

EXAMPLE 11

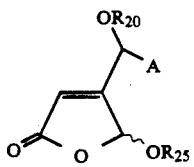

Formula 14

The compounds which are preferred in the method of treatment of the present invention and which are designated by Formula 14 above, have the following preferred structural features. $R_{20}$ is preferably $C_1$–$C_{14}$ alkanoyl. A is preferably CH$_2$—O—$C_8$–$C_{14}$ alkanoyl, CH$_2$—O— napthylpropyl, pyridylpropyl, or methoxyethoxymethoxymethyl. $R_{25}$ is preferably hydrogen or $C_1$–$C_6$ alkanoyl. Examples of such preferred compounds are: 4-[1-dodecanoyloxy-2-(2-methoxyethoxy)-methoxyethyl]-5-hydroxy-2(5H)-furanone (Compound 140); 4-(1,2-didodecanoyloxyethyl)-5-hydroxy-2(5H)-furanone (Compound 141); 4-[1-acetoxy-2-[3-(2-naphthyl)propoxy]ethyl]-5-hydroxy-2(5H)-furanone (Compound 142), and 4-[1-hydroxy-2-[3-(2-naphthyl)propoxy]ethyl]-5-hydroxy-2(5H)-furanone (Compound 143).

The compounds which are shown by Formula 14, including the preferred compounds identified in connection therewith can be prepared in accordance with the disclosure of application Ser. No. 07/699,819, assigned to the same assignee as the present application, which has been allowed. The specification of this allowed application is expressly incorporated herein by reference.

EXAMPLE 12

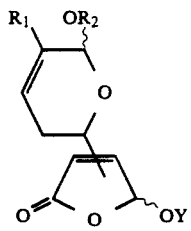

Formula 15

The compounds which are preferred in the method of treatment of the present invention and which are designated by Formula 15 above, have the following preferred structural features. The pyranyl ring is preferably attached to the 4-position of the 2-furanone ring. The $R_1$ group is preferably phenyl ($C_1$–$C_{17}$ alkyl) or benzothienyl ($C_1$–$C_{17}$ alkyl). $R_2$ and Y are preferably hydrogen. Preferred compounds corresponding to Formula 15 are as follows: 4-[3,6-dihydro-6-hydroxy-5-(3-phenylpropyl)-2H-pyran-2-yl]-5-hydroxy-2(5H)-furanone (Compound 150) and 4-[5-(6-(benzo[b]thien-2-yl)-hexyl]-3,6-dihydro-6-hydroxy-2H-pyran-2-yl]-5-hydroxy-2(5H)-furanone (Compound 151).

The compounds which are shown by Formula 15, including the preferred compounds identified in connection therewith can be prepared in accordance with the disclosure of application Ser. No. 07/709,550, as-

EXAMPLE 13

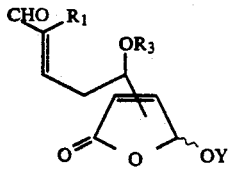

Formula 16

The compounds which are preferred in the method of treatment of the present invention and which are designated by Formula 16 above, have the following preferred structural features. The $R_1$ group is preferably phenyl ($C_1$-$C_{17}$) alkyl, the $R_3$ is preferably hydrogen or $CH_3CO$, and the Y group is preferably hydrogen. The following are examples of preferred compounds corresponding to Formula 16: 5-hydroxy-5-[5-hydroxy-2(5H)-furanon-4-yl]-2-(3-phenylpropyl)-penten-2-al (Compound 160); 5-hydroxy-5-[5-hydroxy-2(5H)-furanon-3-yl]-2-(3-phenylpropyl)-penten-2-al (Compound 161); 5-acetoxy-5-[5-hydroxy-2(5H)-furanon-4-yl]-2-(3-phenylpropyl)-penten-2-al (Compound 162), and 5-acetoxy-5-[5-hydroxy-2(5H)-furanon-3-yl]-2-(3-phenylpropyl)-penten-2-al (Compound 163).

The compounds which are shown by Formula 16, including the preferred compounds identified in connection therewith can be prepared in accordance with the disclosure of application Ser. No. 07/709,550, assigned to the same assignee as the present application, which has been allowed. The specification of this allowed application is expressly incorporated herein by reference.

EXAMPLES 14 AND 15

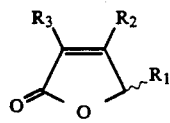

Formula 17

The compounds which are preferred in the method of treatment of the present invention and which are designated by Formula 17 above, have the following preferred structural features. With respect to the $R_1$ substituent in the 5 position of the 2-furanone molecule, the preferred compounds are those where $R_1$ is hydrogen, long chain alkyl, or arylalkyl. Compounds are particularly preferred in this regard where the $R_1$ group is long chain alkyl which is straight chained, or where the $R_1$ is arylalkyl containing a straight alkyl Chain of 3 carbons.

With respect to the $R_2$ substituent in the 4-position of the 2-furanone molecule, compounds are preferred where $R_2$ is hydrogen, or alkyl group, particularly straight chain alkyl.

With respect to position 3 of the 2-furanones of the invention, compounds are preferred where $R_3$ is H, methyl or bromo.

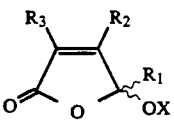

Formula 18

The compounds which are preferred in the method of treatment of the present invention and which are covered by Formula 18 have the same prefered $R_1$, $R_2$, and $R_3$ substituents as the preferred compounds of Formula 17. With respect to the OX substituent in the 5-position of the furanone moiety in Formula 18, those compounds are preferred where the substituent is hydroxy, methoxy or acetyloxy (X is H, or $CH_3O$ or $CH_3CO$).

EXAMPLES of preferred compounds coresponding to Formula 17 (Example 14) and to Formula 18 (Example 15) are listed below.

Formula 17, Compound 170: $R_1=CH_3(CH_2)_8$, $R_2=H$, and $R_3=H$;

Formula 18, Compound 171: $R_1=CH_3(CH_2)_8$, $R_2=H$, $R_3=H$ and $X=H$;

Formula 17, Compound 172: $R_1=(CH_2)_3$—$C_6H_5$, $R_2=CH_3$, and $R_3=CH_3$;

Formula 18, Compound 173: $R_1=H$, $R_2=CH_3(CH_2)_7$, $R_3=Br$ and $X=H$, and

Formula 17, Compound 174: $R_1=H$, $R_2=CH_3(CH_2)_7$ and $R_3=H$.

The compounds of Examples 14 and 15 can be made in accordance with the synthetic chemical pathways illustrated by the following specific examples. The practicing synthetic organic chemist can readily modify the chemical pathways provided by these reactions and specific examples to prepare any and all compounds represented by Formula 17 and Formula 18.

Ethyl 4-hydroxy-6-phenylhex-1-ynoate n-Butyl lithium (a 1.6M solution in hexane: 6.7 ml, 10.7 mmol) was added dropwise to a solution of ethyl propiolate (1.04 g, 10.6 mmol) in tetrahydrofuran (10 ml) at $-78°$ under argon. After 10 minutes, a solution of hydrocinnamaldehyde (1.42 g, 10.6 mmol) in tetrahydrofuran (5 ml) was added. Stirring was continued at $-78°$ C. for 2 hours and acetic acid (1 ml) was added. On warming up to 0°, the reaction mixture was poured into water. Extraction (ethyl ether) and evaporation of the dried (magnesium sulphate) extracts afforded an oil, which was flash chromatographed with silica using 30% ethyl ether/petroleum ether. Fractions with $R_f$ of about 0.28 on evaporation afforded the title ester as a light yellow oil.

$^1$NMR (CDCl$_3$) 1.34 (m, 3H), 2.10 (m, 2H), 2.40 (br, 1H), 2.83 (t, 2H, J=8.3 Hz), 4.25 (q, 2H, J=7.3 Hz), 4.50 (t, 1H, J=7.0 Hz) and 7.29 (m, 5H).

LRMS m/e (% abundance) 233 (M$^+$+1, 2), 232 (M$^+$, 7), 186 (24), 185 (42), 170 (51), 169 (30), 158 (24), 142 (37), 141 (100) and 105 (84).

5-(2-Phenylethyl)-2(5H)-furanone

A solution of ethyl 4-hydroxy-6-phenylhex-1-ynoate (585 mg, 2.5 mmol) in ether (12 ml) was hydrogenated over Lindlar catalyst (50 mg) at room temperature for 3 hours. The mixture was filtered through celite and the filtrate was refluxed with 2M hydrochloric acid (1 ml) for 2½ hours. On cooling, the mixture was dried (magnesium sulphate) and evaporated to dryness to give an oil, which was purified by preparative thin layer chromatography (tlc, 20×20 cm, 2000u silica plate; developed with 30% ethyl ether/petroleum ether). The title furanone was obtained as colorless prisms (recrystallized from ether): mp 66°-7°.

$^1$H NMR (CDCl$_3$) 1.98-2.16 (m, 2H), 2.86 (m, 2H), 5.08 (m, 1H), 6.16 (dd, 1H, J=6.0 Hz, 1.6 Hz), 7.36 (m, 5H) and 7.45 (dd, 1H, J=6.0 Hz, 1.6 Hz).

$^{13}$C NMR (CDCl$_3$) 31.3, 34.9, 82.3, 121.5, 126.3, 128.5, 128.6, 140.2, 156.1 and 172.9.

HRMS exact mass calculated for C$_{12}$H$_{12}$O$_2$ (M+) 188.0837, found 188.0841.

4-Hydroxy-6-phenylhex-2-ynoic acid

A solution of potassium hydroxide (377 mg, 6.7 mmol) in 95% ethanol (10 ml) was added to a solution of ethyl 4-hydroxy-6-phenylhex-1-ynoate (1.04 g, 4.5 mmol) in the same solvent (10 ml) at 0°, and the reaction mixture was stirred at room temperature for 15 hours. After most of the solvent was removed, the residue was dissolved in water (ca. 15 ml) and extracted with dichloromethane (discarded). After the extraction the aqueous phase was acidified to pH 1 with dilute hydrochloric acid and extracted thoroughly with ethyl acetate. Evaporation of the dried (magnesium sulphate) extracts gave the title acid as a pale yellow oil (which crystallizes slowly on standing), which was used directly in the next step.

$^1$H NMR (CDCl$_3$) 2.16 (m, 2H), 2.85 (m, 2H), 4.52 (dd, 1H, J=11.3 Hz, 6.6 Hz), 5.10 (br, 2H) and 7.31 (m, 5H).

LRMS m/e (% abundance) 204 (M+, 6), 142 (42), 141 (75), 134 (21), 133 (11), 131, (10), 118 (34), 117 (32), 115 (21) and 105 (100).

4-Keto-6-phenylhex-2-ynoic acid

A solution of Jones Reagent (a 2.67M solution in sulphuric acid; 2.07 ml, 5.5 mmol) was added dropwise to a solution of 4-hydroxy-6-phenylhex-2-ynoic acid (750 mg, 3.7 mmol) in acetone (12 ml) at 0° and the reaction mixture was maintained at 0° for 70 minutes. The mixture was quenched with ethanol (2 ml) and extracted with ethyl ether. Evaporation of the dried (magnesium sulphate) extracts gave the title acid as a yellow oil which was used directly in the next step.

$^1$ NMR (CDCl$_3$) 3.02 (s, 4H), 7.30 (m, 5H) and 8.80 (br, 1H, exchanged with D$_2$O).

5-Hydroxy-5-(2-phenylethyl)-2-furanone

A solution of 4-keto-6-phenylhex-2-ynoic acid (228 mg, 1.1 mmol) in ethyl ether (8 ml) was hydrogenated over Lindlar catalyst (20 mg) at 0° for 80 minutes. The mixture was filtered through celite and the filtrate, after evaporation to dryness, was purified by preparative tlc (20×20 cm, 1000u silica plate; developed with 60% ethyl ether/hexane). The title furanone was obtained as a colorless oil.

$^1$H NMR (CDCl$_3$) 2.31 (dd, 2H, J=10.8 Hz, 5.5 Hz), 2.78 (dd, 2H, J=10.8 Hz, 5.5 Hz), 4.80 (br, 1H), 6.11 (d, 1H, J=5.8 Hz), 7.20 (m, 5H) and 7.28 (d, 1H, J= 5.8 Hz).

$^{13}$C NMR (CDCl$_3$) 29.7, 39.1, 107.8, 123.1, 126.4, 128.3, 128.7, 140.3, 154.3 and 171.0.

HRMS exact mass calculated for C$_{12}$H$_{12}$O$_3$ (M+) 204.0786, found 204.0792.

Ethyl 4-hydroxytridec-2-ynoate

Methylmagnesium bromide (a 3M solution in tetrahydrofuran; 7.8 ml, 23.4 mmol) was added dropwise to a solution of ethyl propiolate (2.25 g, 22.9 mmol) in tetrahydrofuran (10 ml) at −78° under argon. After 10 minutes, a solution of decyl aldehyde (3.58 g, 22.9 mmol) in tetrahydrofuran (2 ml) was added. Stirring was continued for 1 hour while the cooling bath was warmed to room temperature. The mixture was quenched with saturated ammonium chloride solution and extracted with ethyl ether. Evaporation of the dried (magnesium sulphate) extracts gave an oil, which was flash chromatographed on silica using 30% ethyl ether/petroleum ether. Fractions with R$_f$ of about 0.31 gave, after evaporation, the title ester as a deep, yellow oil.

$^1$H NMR (CDCl$_3$) 0.88 (t, 3H, J=6.4 Hz), 1.27 (br s, 14H), 1.75 (m, 2H) and 4.25 (q, 2H, J=6.4 Hz).

LRMS m/e % abundance) 255 (M+ +1, 5), 254 (M+, 5), 237 (6), 209 (8), 181 (12), 179 (11), 163 (13), 152 (12), 151 (13), 137 (16), 130 (19), 128 (100), 100 (66) and 71 (35).

5-Nonyl-2(5H)-furanone (Compound 170)

A solution of ethyl 4-hydroxytridec-2-ynoate (230.6 ml, 1.02 mmol) in ether (10 ml) was hydrogenated over Lindlar catalyst (20 mg) at 0° for 1 hour. The mixture was filtered through celite and after evaporation the filtrate gave a residue, which was flash chromatographed on silica using 60% ethyl ether/petroleum ether. Fractions with R$_f$ of about 0.18 gave after evaporation a colorless oil (157 mg, 59%) identified by $^1$H NMR as ethyl (E)-4-hydroxytridec-2-enoate: $^1$H NMR (CDCl$_3$) 0.92 (t, 3H, J=6.7 Hz), 1.31 (br s, 14H), 1.65 (m, 2H), 4.97 (q, 1H, J=6.2 Hz), 5.91 (d, 1H, J=12.5 Hz) and 6.41 (dd, 1H, J=12.5 Hz, 7.3 Hz). The oil on crystallization from petroleum ether, in the presence of a drop of acetic acid, lactonized to give the title furanone as a colorless oil.

$^1$H NMR (CDCl$_3$) 0.92 (t, 3H, J=6.7 Hz), 1.30 (br s, 12H), 1.45 (m, 2H), 1.75 (m, 2H), 5.08 (m, 1H), 6.14 (dd, 1H, J=5.9 Hz, 2.6 Hz) and 7.48 (dd, 1H, J=5.3 Hz, 1.4 Hz).

$^{13}$C NMR (CDCl$_3$) 14.1, 22.6, 25.0, 29.2, 29.3, 29.4, 31.8, 33.2, 83.4, 121.5, 156.3 and 173.1.

HRMS m/e: exact mass calculated for C$_{13}$H$_{22}$O$_2$ (M+) 210.1620, found 210.1624.

4-Hydroxytridec-2-ynoic acid

A solution of potassium hydroxide (885 mg, 15.8 mmol) in 95% ethanol (35 ml) was added to ethyl 4-hydroxytridec-2-ynoate (2.68 g, 10.5 mmol) in the same solvent (5 ml) at 0°. After stirring at room temperature for 9 hours, most of the solvent was removed and water (20 ml) was added. The mixture was extracted thoroughy with dichloromethane (discarded), acidified to pH 1 with dilute hydrochloric acid and extracted with ethyl acetate. Evaporation of the dried (magnesium sulphate) ethyl acetate extracts gave an off-white solid, which on recrystallization from petroleum ether (at −78°) gave the title acid as colorless prisms: mp 65°-6°.

$^1$H NMR (CDCl$_3$) 0.93 (t, 3H, J=5.7 Hz), 1.31 (br s, 12H), 1.50 (br, 1H), 1.81 (m, 2H), 4.56 (dt, 1H, J =5.0 Hz, 1.9 Hz) and 5.00 (br, 1H).

LRMS m/e (% abundance) 226 (M+, 5), 137 (13), 124 (12), 121 (18), 107 (26), 100 (94), 97 (33), 95 (27), 93 (43) 85 (48), 83 (63), 79 (55) and 71 (75).

4-Ketotridec-2-ynoic-acid

Jones reagent (a 2.67M solution in sulphuric acid; 1.32 ml, 3.5 mmol) was added dropwise to a solution of 4-hydroxytridec-2-ynoic acid (531.8 mg, 2.4 mmol) in acetone (10 ml) at 0° and the reaction mixture was maintained at 0° for 70 minutes. The mixture was quenched with ethanol (1 ml) and dried with magnesium sulphate. On evaporation, the title acid was obtained as a colorless oil.

$^1$H NMR (CDCl$_3$) 0.87 (t, 3H, J=6.6 Hz), 1.25 (br s, 12H), 1.67 (m, 2H), 2.64 (t, 2H, J=7.2 Hz) and 4.90 (br, 1H).

LRMS m/e (% abundance) 224 (M+, 5), 223 (12), 197 (36), 155 (37), 149 (14), 37 (21), 123 (15), 111 (14), 109 (12) and 97 (34).

5-Hydroxy-5-nonyl-2-furanone (Compound 171)

A solution of 4-ketotridec-2-ynoic acid (220 mg, 0.98 mmol) in ether (10 ml) was hydrogenated over Lindlar catalyst (10 mg) at 0° for 80 minutes. The mixture was filtered through celite and after evaporation to dryness the filtrate gave an oil, which was purified by preparative tlc (20×20 cm, 1000u silica plate; developed with 60% ethyl ether/petroleum ether). The title furanone was obtained as colorless prisms (recrystallized from petroleum ether): mp 54°-5°.

$^1$H NMR (CDCl$_3$) 0.88 (t, 3H, J=7.5 Hz), 1.26 (br s, 12H), 1.40 (m, 2H), 1.98 (m, 2H), 6.12 (d, 1H, J = 6.4 Hz) and 7.16 (d, 1H, J=6.4 Hz).

$^{13}$C NMR (CDCl$_3$) 14.1, 22.6, 23.4, 29.3, 29.4, 31.8, 37.5, 108.5, 123.0, 154.5 and 170.8.

HRMS m/e: exact mass calculated for C$_{13}$H$_{22}$O$_3$ (M+) 226.1569, found 226.1568.

5-Hydroxy-5-methyl-4-octyl-2-furanone

A mixture of 2-undecanone (10 g, 58.7 mmol), glyoxylic acid monohydrate (5.15 g, 56 mmol) and 85% phosphoric acid (10 ml) was warmed at 80° for 18 hours. On cooling to room temperature, the mixture was diluted with ethyl ether/dichloromethane (50 ml each) and washed thoroughly with brine. Evaporation of the dried (magnesium sulphate) organic phase gave a yellow oil which on crystallization from ethyl ether/petroleum ether gave 4-ketotridec-2-enoic acid as colorless prisms.

$^1$H NMR (CDCl$_3$) 0.96 (t, 3H, J=7.4 Hz), 1.34 (br s, 12H), 1.72 (p, 2H, J=7.1 Hz), 2.73 (t, 2H, J=7.1 Hz), 6.74 (d, 1H, J=15.7 Hz) and 7.22 (d, 1H, J = 15.7 Hz).

The mother liquor from the above recrystallization was concentrated down and was flash chromatographed on silica using 40% ethyl acetate/petroleum ether. Fractions with R$_f$ of about 0.1 gave, after evaporation, the title furanone as a pale yellow oil.

$^1$H NMR (CDCl$_3$) 0.92 (t, 3H, J=7.4 Hz), 1.30 (br s, 12H), 2.45 (s, 3H), 2.79 (t, 2H, J=7.5 Hz) and 6.56 (s, 1H).

$^{13}$C NMR (CDCl$_3$) 14.1, 22.7, 26.7, 27.0, 29.2, 29.3, 29.8, 31.9, 124.5, 158.0, 171.3 and 200.0.

HRMS m/e: exact mass calculated for C$_{13}$H$_{22}$O$_3$ (M+) 226.1569, found 226.1559.

5-Methyl-4-octyl-2(5H)-furanone

Sodium borohydride (214 mg, 5.7 mmol) was added to a solution of 5-hydroxy-5-methyl-4-octyl-2-furanone (640 mg, 2.8 mmol) in tetrahydrofuran (15 ml). After stirring at room temperature for 80 minutes, most of the solvent was removed and water (10 ml) was added. Extraction (dichloromethane) and evaporation of the dried (magnesium sulphate) extracts gave a residue, which was flash chromatographed on silica using 60% ethyl ether/petroleum ether. Fractions with R$_f$ of about 0.23 were evaporated to yield the title furanone as a colorless oil, which crystallized slowly on storage at −70°.

$^1$H NMR (CDCl$_3$) 0.85 (t, 3H, J=5.4 Hz), 1.26 (br s, 10H), 1.33 (d, 3H, J=6.9 Hz), 1.47 (m, 2H), 2.26 (m, 1H), 2.83 (m, 1H0, 4.33 (q, 1H, J=6.2 Hz) and 5.99 (s, 1H).

$^{13}$C NMR (CDCl$_3$) 14.1, 22.4, 22.6, 29.2, 29.3, 29.5, 29.8, 31.9, 71.1, 113.0, 169.2 and 171.8.

HRMS m/e exact mass calculated for C$_{13}$H$_{22}$O$_2$ (M+) 210.1620, found 210.1617.

4-Ethyl-5-hydroxy-5-methyl-2-furanone

A mixture of 2-pentanone (17.1 g, 198 mmol), glyoxylic acid monohydrate (8.05 g, 88 mmol) and about 85% phosphoric acid (12 ml) was warmed at ca. 80° for 19 hours. On cooling to room temperature the mixture was diluted with ethyl ether/dichloromethane (100 ml, 1:1) and washed thoroughly with brine. Evaporation of the dried (magnesium sulphate) organic phase gave a yellow viscous oil, which on crystallization from ethyl ether/petroleum ether gave 4-keto-hept-2-enoic acid as colorless prisms: mp 100°-2°.

$^1$H NMR (CDCl$_3$) 1.01 (t, 3H, J=7.9 Hz), 1.73 (p, 2H, J=7.1. Hz), 2.70 (t, 2H, J=7.3 Hz), 6.73 (1H, d, J=15.8 Hz) and 7.19 (d, 1H, J=15.8 Hz).

HRMS m/e: exact mass calculated for C$_7$H$_{10}$O$_3$ (M+) 142.0630, found 142.0622.

The mother liquor from the above crystallization was evaporated to dryness and extracted thoroughly with petroleum ether. The combined extracts were concentrated and cooled to −20° to give the title furanone as colorless prisms: mp 37°-8°.

$^1$H NMR (CDCl$_3$) 1.09 (t, 3H, J=7.8 Hz), 2.46 (s, 3H), 2.83 (q, 2H), J=7.8 Hz) and 6.57 (s, 1H).

$^{13}$C NMR (CDCl$_3$) 13.6, 20.4, 26.6, 124.6, 158.7, 171.2 and 199.9.

HRMS m/e: exact mass calculated for C$_7$H$_{10}$O$_3$ (M+) 142.0630, found 142.0622.

4-Ethyl-5-methyl-2(5H)-furanone

Sodium borohydride (646 mg, 17 mmol) was added to a solution of 4-ethyl-5-hydroxy-5-methyl-2-furanone (1.21 g, 8.5 mmol) in tetrahydrofuran (10 ml) at room temperature. After ½ hour, most of the solvent was removed and water (10 ml) was added. Extraction (ethyl acetate) and evaporation of the dried (magnesium sulphate) extracts gave an oil, which was flash chromatographed on silica using 60% ethyl ether/petroleum ether. Fractions with R$_f$ of about 0.23 gave after evaporation, a pale yellow oil, which slowly crystallized on storage at −20°. Recrystallization from ethyl ether/petroleum ether afforded the title furanone as colorless prisms: mp 86°-7°.

$^1$H NMR (CDCl$_3$) 1.16 (t, 3H, J=7.2 Hz), 1.39 (d, 3H, J=5.4 Hz), 2.36 (m, 1H), 2.84 (m, 1H), 4.41 (q, 2H, J=7.2 Hz) and 6.04 (s, 1H).

$^{13}$C NMR (CDCl$_3$) 13.8, 22.3, 22.8, 71.0, 112.9, 170.3 and 171.7.

HRMS m/e: exact mass calculated for C$_7$H$_{10}$O$_2$ (M+) 126.0681, found 126.0683.

3,4-Dimethyl-5-hydroxy-5-(1-octynyl)-2-furanone n-Butyl lithium (a 1.6M solution in hexane; 6.78 ml, 10.9 mmol) was added dropwise to a solution of 1-octyne (1.13 g, 10 mmol) in tetrahydrofuran (7 ml) at −78° under argon. After 20 minutes, the solution was cannulated dropwise, under argon, to a solution of 2,3-dimethylmaleic anhydride (1.30 g, 10.3, mmol) in tetrahydrofuran (15 ml) cooled at −78°. Stirring was continued for 2 hours while the cooling bath attained room temperature. The mixture was quenched with dilute hydrochloric acid, diluted with water (10 ml) and extracted with ethyl acetate. Evaporation of the dried (magnesium sulphate) extracts gave an oil, which was flash chromatographed on silica using 30% ethyl ether/petroleum ether. Fractions with R$_f$ of about 0.18 on evaporation afforded a light yellow viscous oil, which crystallized out slowly on storage at −20°. Recrystallization from petroleum ether gave the title furanone as colorless prisms: mp 55°-6°.

$^1$H NMR (CDCl$_3$) 0.85 (t, 3H, J=7.4 Hz), 1.24 (m, 6H), 1.49 (p, 2H, J=7.9 Hz), 1.79 (s, 3H), 2.00 (s, 3H), 2.21 (t, 2H, J=7.2 Hz) and 3.93 (br, 1H).

$^{13}$C NMR (CDCl$_3$) 8.4, 10.5, 13.9, 18.5, 22.4, 27.9, 28.4, 31.1, 74.5, 88.2, 98.0, 124.3, 156.9 and 172.1.

HRMS m/e: exact mass calculated for C$_{14}$H$_{20}$O$_3$ (M+) 237.1491, found 237.1498.

3,4-Dimethyl-5-hydroxy-5-(3-phenylpropyl)-2-furanone

A mixture of 3-phenyl-1-bromopropane (521 mg, 2.6 mmol) and magnesium turnings (66 mg, 2.8 mmol) in tetrahydrofuran (5 ml) was refluxed under argon for 90 minutes. After the reaction mixture had been cooled to −78°, a solution of 2,3-dimethylmaleic anhydride (330 mg, 2.6 mmol) in tetrahydrofuran (5 ml) was added dropwise. Stirring was continued overnight (ca. 17 hours) while the cooling bath attained room temperature. The mixture was quenched with a saturated solution of ammonium chloride and extracted with ethyl acetate. Evaporation of the dried (magnesium sulphate) extracts gave an oil, which was flash chromatographed on silica using 40% ethyl acetate/petroleum ether. Fractions with R$_f$ of about 0.32 on evaporation afforded the title furanone as a pale yellow oil, which on storage at −20° crystallized as colorless prisms: mp 62°-3° C.

$^1$H NMR (CDCl$_3$) 1.48 (m, 1H), 1.70 (m, 1H), 1.79 (s, 3H), 1.89 (s, 3H), 2.05 (m, 2H), 2.65 (m, 2H) and 7.25 (m, 5H).

$^{13}$C NMR (CDCl$_3$) 8.3, 10.6, 24.7, 35.4, 107.2, 125.1, 125.9, 128.4, 141.5, 158.1 and 172.6.

HRMS m/e: exact mass calculated for C$_{15}$H$_{18}$O$_3$ (M+) 246.1256, found 246.1270.

3,4-Dimethyl-5-(3-phenylpropyl)-2(5H)-furanone (Compound 172)

Potassium borohydride (503 mg, 9.3 mmol) was added to a solution of 3,4-dimethyl-5-hydroxy-5-(3-phenylpropyl)-2-furanone (382 mg, 1.6 mmol) in tetrahydrofuran (8 ml) and methanol (6 ml) at room temperature. After 7 hours, most of the solvent was removed and water (10 ml) was added. Extraction (ethyl acetate) and evaporation of the dried (magnesium sulphate) extracts gave an oil, which was purified by preparative tlc (20×20 cm, 2000u silica plate; developed with 30% ethyl ether/petroleum ether). The title furanone was obtained as colorless prisms (recrystallized from ethyl ether/petroleum ether): mp 69°-70°.

$^1$H NMR (CDCl$_3$) 1.50 (m, 1H), 1.77 (p, 2H, J=6.8 Hz), 1.82 (s, 3H), 1.92 (s, 3H), 1.95 (m, 1H), 2.67 (m, H), 4.74 (m, 1H) and 7.25 (m, 5H).

$^{13}$C NMR (CDCl$_3$) 8.4, 11.9, 26.0, 31.5, 35.4, 82.9, 123.6, 125.9, 128.4, 141.5 and 158.9.

HRMS m/e: exact mass calculated for C$_{15}$H$_{18}$O$_2$ (M+) 230.1307, found 230.1311.

4-Octyl-5-hydroxy-2(5H)-furanone

A mixture of glyoxylic acid monohydrate (1.19 g, 16.1 mmol), morpholine hydrochloride (1.81 g, 14.6 mmol), water (0.73 ml) and 1-decanal (2.89 ml, 15.4 mmol) in dioxane (6 ml) was stirred at room temperature for 1 hour, followed by reflux for 25 hours. After cooling, most of the solvent was removed by evaporation and the residue was extracted with ethyl ether. Evaporation of the dried (magnesium sulfate) extracts gave an oil, which was flash chromatographed with 30% ethyl acetate/hexane to give the title furanone.

$^1$H NMR (CDCl$_3$): 0.89 (t, 3H, J=6.6 Hz), 1.25 (br s, 10H), 1.60 (m, 2H), 2.40 (m, 2H), 4.70 (br, 1H), 5.84 (s, 1H) and 6.00 (s, 1H).

4-Octyl-5-methoxy-2(5H)-furanone

A mixture of 4-octyl-5-hydroxy-2(5H)-furanone (244 mg, 1.16 mmol) and 4-toluenesulfonic acid (33 mg, 0.17 mmol) and methanol (5.8 ml) was stirred at room temperature for 2 days. The mixture was diluted with ethyl ether and washed thoroughly with 5% sodium bicarbonate solution. Evaporation of the dried (magnesium sulfate) organic phase gave an oil, which was flash chromatographed o silica using 10% ethyl acetate/hexane to give the title furanone.

$^1$H NMR (CDCl$_3$): 0.89 (t, 3H, J=7.5 Hz), 1.28 (br s, 10H), 1.60 (m, 2H), 2.35 (m, 2H), 3.56 (s, 3H), 5.64 (s, 1H) and 5.86 (s 1H).

3-Bromo-4-octyl-5-methoxy-2(5H)-furanone

A solution of bromine (28 microliter) in carbontetrachloride (0.2 ml) was added to a solution of 4-octyl-5-methoxy-2(5H)-furanone (100 mg, 0.45 mmol) in carbon tetrachloride (0.5 ml) at 0°. The mixture was stirred at room temperature until all the starting material disappeared (as monitored by tlc). After cooling to 0°, pyridine (86 microliter, 1.17 mmol) was added. The mixture was quenched with water and the layers were separated. Evaporation of the dried (magnesium sulfate) organic phase gave an oil, which was purified by flash chromatography using 5% ethyl acetate/hexane to give the title furanone.

$^1$H NMR (CDCl$_3$): 0.89 (t, 3H, J=6.8 Hz), 1.28 (br s, 15H), 1.60 (m, 2H), 2.50 (m, 2H), 3.58 (s, 3H) and 5.69 (s, 1H).

3-Bromo-4-octyl-5-hydroxy-2(5H)-furanone (Compound 173)

A mixture of 3-bromo-4-octyl-5-methoxy-2(5H)-furanone (106 mg, 0.35 mmol) and concentrated hydrochloric acid (0.21 ml) was refluxed until all the starting material disappeared as shown by tlc. After cooling, the mixture was diluted with ethyl ether and was neutralized by washing thoroughly with saturated potassium bicarbonate solution.. Evaporation of the dried (magnesium sulfate) organic phase gave an oil, which was flash chromatographed on silica using 10% ethyl acetate/hexane to give the title furanone.

IR (CHCl$_3$): 3389, 1755 and 1651.

$^1$H NMR (CDCl$_3$): 0.87 (t, 3H, J=7.2 Hz), 1.27 (br s, 10H), 1.60 (m, 2H), 2.49 (t, 2H, J=8.5 Hz), 4.50 (br, 1H), and 6.05 (s, 1H).

$^{13}$C NMR (CDCl$_3$): 14.2, 22.7, 26.5, 27.8, 29.2, 29.6, 31.8, 98.8, 112.1 and 163.9.

HRMS exact mass calculated for C$_{12}$H$_{20}$BrO$_3$ (M+H)$^+$ 291.0596, found 291.0590.

EXAMPLES 16 AND 17

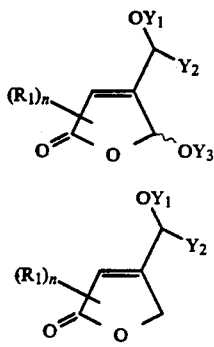

Formula 19a

Formula 19b

The compounds which are preferred in the method of treatment of the present invention and which are designated by Formula 19a and 19b above, have the following preferred structural features. With respect to the R$_1$ substituent those compounds are preferred where R$_1$ is alkyl of 1 to 6 carbons, more preferably methyl or butyl, and where R$_1$ is phenyl.

With respect to Y$_1$ in Formula 19 compounds are preferred where Y$_1$ is H, acyl, more preferably acetyl, and where Y$_1$ represents a phenylcarbamoyl (C$_6$H$_5$—NH—CO—) group. Y$_1$ also preferably represents a lauroyl (CH$_3$—(CH$_2$)$_{10}$—CO) group, particularly when Y$_2$ is H.

With respect to Y$_2$ of Formula 19 Compounds are preferred in accordance with the method of the present invention where Y$_2$ is long chain normal alkyl, preferably normal alkyl of 8 to 25 carbon atoms; particularly preferred are compounds where Y$_2$ represents a normal dodecyl group.

The Y$_3$ group of Formula 19 is preferably H, or acetyl.

With respect to n, compounds are preferred where n is 1; also preferred are the compounds where n is 2 and where Y$_2$ is H.

Examples of preferred compounds shown by Formula 19 are listed below with continuing reference to reference to Formula 19a, where for the listed specific examples Y$_3$=H.

Compound 180: n=1, R$_1$=5-methyl, Y$_1$=CH$_3$CO; Y$_2$=(CH$_2$)$_{11}$—CH$_3$

Compound 181: n=1, R$_1$=3-methyl, Y$_1$=CH$_3$CO; Y$_2$=(CH$_2$)$_{11}$—CH$_3$

Compound 182: n=1, R$_1$=3-methyl, Y$_1$=C$_6$H$_5$—NHCO; Y$_2$=(CH$_2$)$_{11}$—CH$_3$ Compound 183: n=1, R$_1$=5-methyl, Y$_1$=C$_6$H$_5$—NHCO; Y$_2$=(CH$_2$)$_{11}$—CH$_3$ Compound 184: n=1, R$_1$=5-butyl, Y$_1$=C$_6$H$_5$—NHCO; Y$_2$=(CH$_2$)$_{11}$—CH$_3$ Compound 185: n=2, R$_1$=3-phenyl, R$_1$=methyl, Y$_1$=CO—(CH$_2$)$_{10}$—CH$_3$; Y$_2$=H Compound 186: n=1, R$_1$=5-methyl, Y$_1$=CO—(CH$_2$)$_{10}$—CH$_3$; Y$_2$=H Compound 187: n=1, R$_1$=3-phenyl, Y$_1$=C$_6$H$_5$—NHCO; Y$_2$=(CH$_2$)$_{11}$—CH$_1$ Compound 188: n=1, R$_1$=3-phenyl, Y$_1$=CH$_3$CO; Y$_2$=(CH$_2$)$_{11}$—CH$_3$

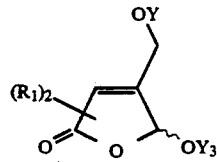

Formula 20a

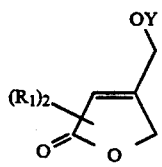

Formula 20b

An example of a compound utilized in the method of treatment of the present invention and covered by Formula 20a is 4-dodecoyloxymethyl-5-hydroxy-5-methyl-3-phenyl-2-furanone (Compound 189).

The compounds of Examples 16 and 17 can be made in accordance with the synthetic chemical pathways illustrated by the following specific examples. The practicing synthetic organic chemist can readily modify the chemical pathways provided by these specific reactions and examples to prepare any and all compounds represented by Formula 19a and b and Formula 20a and b. Generally speaking, the compounds of Formula 19b and 20b can be prepared by sodium borohydride reduction of a compound of Formula 19a or 20a where the 5 position bears an OH group (Y$_3$=H).

2-Trimethylsilyl-4-furaldehyde n-Butyl lithium (a 2.5M solution in hexane; 28.8 ml, 72 mmol) was added to a solution of morpholine (6.28 ml, 72 mmol) in tetrahydrofuran (700 ml) at −78° under argon. After 20 minutes, 3-furaldehyde (7.0 g, 72 mmol) was added. After another 20 minutes, sec-butyl lithium (a 1.3M solution in cyclohexane; 55.4 ml, 72 mmol) was added dropwise and stirring continued at −78° for 7 hours before trimethylsilyl chloride (27 ml, 216 mmol) was added. Stirring was continued overnight (14 hours) while the cooling bath was allowed to attain room temperature. The solution was poured into ice cold 10% (v/v) hydrochloric acid (200 ml) and after stirring at 0° for 10 minutes, the layers were separated. The aqueous phase was extracted with diethyl ether. All the organic phases were combined, dried (magnesium sulfate) and evaporated to dryness to give a light brown oil, which was purified by flash chromatography on silica using 2% ethyl ether/hexane. Fractions with R$_f$ of about 0.30 (silica, 10% ethyl ether/hexane) on evaporation gave the title aldehyde as a light yellow oil, b.p. 48°-50°/0.25 torr.

$^1$H NMR (CDCl$_3$) 0.29 (s, 9H), 6.98 (s, 1H), 8.25 (s, 1H) and 9.95 (s, 1H).

$^{13}$C NMR (CDCl$_3$) −2.0, 116.2, 128.9, 155.3, 164.1 and 184.5.

HRMS exact mass calculated for C$_8$H$_{12}$O$_2$Si(M+) 168.0607, found 168.0588. See also U.S. Pat. No. 4,935,530, the specification of which is incorporated herein by reference.

2-Triethylsilyl-4-furaldehyde n-Butyl lithium (a 2.5M solution in hexane; 30.6 ml, 76.5 mmol) was added to a solution of morpholine (6.66 ml, 76.5 mmol) in tetrahydrofuran (500 ml) at −78° under argon. After 15 minutes, 3-furaldehyde (6.3 ml, 72.8 mmol) was added. After another 20 minutes, sec-butyl lithium (a 1.3M solution in cyclohexane; 59.0 ml, 76.5 mmol) was added dropwise and stirring continued at −78° for about 2 hours before triethylsilylchloride (13.4 ml, 80.1 mmol) was added. Stirring was continued overnight (14 hours) while the cooling bath was allowed to attain room temperature. The solution was poured into ice cold 10% (v/v) hydrochloric acid (100 ml) and after stirring at 0° for 10 minutes, the layers were separated. The aqueous phase was extracted with diethyl ether. All the organic phases were combined, dried (magnesium sulfate) and evaporated down to give an oil, which was distilled under high vacuum to give the 5-triethylsily-3-furaldehyde as a pale yellow oil, boiling point 85°-90°/0.4 torr.

IR (neat) 1680cm$^{-1}$ $^1$H NMR (CDCl$_3$) 0.79 (q, 6H, J=7.3 Hz), 0.90 (t, 9H, J=7.3 Hz), 7.0 (s, 1H), 8.26 (s, 1H) and 9.95 (s, 1H).

$^{13}$C NMR (CDCL$_3$) 2.9, 7.1, 117.2, 128.8, 155.6, 162.3 and 184.6.

HRMS m/e exact mass calculated for C$_{11}$H$_{18}$O$_2$Si(M+) 210.1076, found 210.1071. See also U.S. Pat. No. 4,935,530, the specification of which is incorporated herein by reference.

2-(tert-Butyldimethylsilyl)-4-furaldehyde n-Butyl lithium (a 2.5M solution) in hexane; 8.3 ml, 20.8 mmol) was added to a solution of morpholine (1.81 ml, 20 mmol) in tetrahydrofuran (100 ml) at −78° C. under argon. After 20 minutes 3-furaldehyde (1.8 ml, 20.8 mmol) was added. After another 15 minutes, sec-butyl lithium (a 1.3M solution in cyclohexane; 16.8 ml, 21.9 mmol) was added dropwise and stirring continued at −78° C. for 1 hour before a solution of t-butyldimethylsilyl chloride (9.4 g, 62.4 mmol) in tetrahydrofuran (10 ml) was added. Stirring was continued overnight (16 hours) while the cooling bath was allowed to attain room temperature. The solution was poured into ice cold 10% (v/v) hydrochloric acid (40 ml) and after stirring at 0° for 10 minutes, the layers were separated. The aqueous phase was extracted with diethyl ether. All the organic phases were combined, dried (magnesium sulfate) and evaporated to dryness to give a brown oil, which was distilled under high vacuum to give the title aldehyde, boiling point 80°-5°/0.5 torr., m.p. 37-8.

$^1$H NMR (CDCl$_3$) 0.23 (s, 6H), 0.90 (s, 9H), 6.99 (s, 1H), 8.25 (s, 1H) and 9.94 (s, 1H).

$^{13}$C NMR (CDCl$_3$) 16.6, 26.1, 117.3, 128.8, 155.5, 162.7 and 184.5.

HRMS exact mass calculated for C$_{11}$H$_{18}$O$_2$Si (M+) 210.1076, found 210.1075.

5-Methyl-2-trimethylsilyl-4-furaldehyde n-Butyl lithium (a 1.6M solution in hexane; 2.04 ml, 3.28 mmol) was added dropwise to a solution of N,N'N'-trimethylethylenediamine (0.46 ml, 3.56 mmol) in tetrahydrofuran (7 ml) at −78 degrees under argon. After 15 minutes, a solution of 2-trimethylsilyl-4-furaldehyde (0.5 g, 2.98 mmol) in tetrahydrofuran (2 ml) was added, followed by n-butyl lithium (3.72 ml, 5.94 mmol) after 15 minutes. Iodomethane (1.12 ml, 17.9 mmol) was then added and the mixture was allowed to warm to room temperature gradually over ½ hour. The mixture was quenched with brine and extracted with ethyl ether. Evaporation of the dried (magnesium sulphate) extracts gave an oil, which was purified by flash chromatography using 10% ethyl ether/hexane. Fractions with R$_f$ of about 0.22 on evaporation afforded the title methylfuran as a light yellow oil.

$^1$H NMR (CDCl$_3$) 0.29 (s, 9H), 2.63 (s, 3H), 6.91 (s, 1H) and 9.95 (s, 1H).

LRMS m/e (% abundance) 183 (M+ +1, 35), 167 (28), 149 (20), 83 (40), 73 (100) and 43 (31).

5-Methyl-4-(1-acetoxytridecyl)-2-trimethylsilylfuran

A mixture of 1-bromododecane (261 mg, 0.11 mmol) and magnesium turnings (27 mg, 0.11 mmol) in tetrahydrofuran (7 ml) was refluxed under argon for 1 hour. After cooling to room temperature, a solution of 5-methyl-2-trimethylsilyl-4-furaldehyde (158.6 mg, 0.87 mmol) in tetrahydrofuran (1 ml) was added, followed by acetic anhydride (0.25 ml, 2.6 mmol) after 1 hour. Stirring was continued at room temperature overnight and the mixture was quenched with water. Extraction (ethyl ether) and evaporation of the dried (magnesium sulphate) extracts gave an oil, which was purified by preparative TLC (20×20 cm, 1000 micron silica plate; developed with 5% ethyl ether/hexane). The title ester was obtained as a light yellow oil.

$^1$H NMR (CDCl$_3$) 0.26 (s, 9H), 0.91 (t, 3H, J=6.9 Hz), 1.27 (s, 20H), 1.60-1.90 (m, 2H), 2.05 (s, 3H), 2.35 (s, 3H), 5.69 (t, 1H, J=7.5 Hz) and 6.55 (s, 1H).

LRMS m/e (% abundance) 394 (M+, 8), 352 (23), 334 (36), 183 (47), 167 (20), 117 (28), 73 (100) and 43 (41).

4-(1-Acetoxytridecyl)-5-hydroxy-5-methyl-2-furanone (Compound 180)

A mixture of 5-methyl-4-(1-acetoxytridecyl)-2-trimethylsilylfuran (237 mg, 0.60 mmol) and Rose Bengal (5 mg) in tetrahydrofuran (10 ml) was exposed to singlet oxygen at −78 degrees C. for 2 hours. The residue, after solvent removal, was purified by preparative TLC (20×20 cm, 1000 micron silica plate; developed with 60% ethyl ether/hexane). The title furanone was obtained as a light yellow oil. This compound is a mixture of epimers which isomerizes upon standing.

$^1$H NMR (CDCl$_3$) 0.92 (t, 3H, J=6.9 Hz), 1.30 (brs, 20H), 1.70 (brs, 3H), 1.80 (m, 2H), 2.15 (2s, 3H), 5.25 (brm, 1H), 5.45 (t, 0.7H, J=7.5 Hz), 5.96 (s, 0.7H), 6.03 (s, 0.3H) and 6.11 (brm, 0.3H).

$^{13}$C NMR (CDCl$_3$) 13.7, 20.5, 22.3, 23.3, 24.1, 24.9, 28.8, 29.0, 29.1, 29.2, 29.3, 31.6, 33.2, 33.3, 69.0, 69.3, 106.5, 117.0, 118.1, 169.6, 169.7, 169.8, 170.0, 170.1, 170.7, 171.9 and 172.0.

HRMS exact mass calculated for C$_{20}$H$_{38}$NO$_5$ (M+NH$_4$)+372.2749, found 372.2754.

3-(O-tert-Butyldimethylsilylmethoxy)furan

3-Furylmethanol (15.5 ml, 0.18 mol), followed by 1,8-diazabicyclo[5.4.0]undec-7-ene (29.7 ml, 0.19 mol) was added to a solution of tert-butyldimethylsilyl chloride (29.9 g, 0.19 m) in dichloromethane (140 ml) at 0 degrees C. under argon. After stirring at room temperature overnight, the reaction was quenched with 5% ice cold hydrochloric acid. Extraction with dichloromethane and evaporation of the dried (magnesium sulfate) extracts gave an oil which was purified by flash chromatography on silica using hexane to give the desired silyl ether.

'H NMR (CDCl$_3$): 0.05 (s, 6H), 0.89 (s, 9H), 4.58 (s, 2H), 6.35 (1H) and 7.33 (m, 2H).

3-(2-tert-Butyldimethylsilyl)furylmethanol n-BuLi (a 1.5M solution in hexane; 38.9 ml, 58 mmol) was added to a solution of 3-(O-tert-butyldimethylsilylmethoxy)furan (11.2 g, 52.7 mmol) and hexamethylphosphoramide(10.1 ml, 58 mmol) in tetrahydrofuran (200 ml) at −78 degrees C. under argon. After 1 hour stirring at −20 degrees C., the reaction was quenched with an aqueous solution of saturated ammonium chloride. Extraction (ethyl acetate) and evaporation of the dried (magnesium sulfate) extracts gave an oil, which was purified by flash chromatography on silica using 20% ethylacetate/hexane to give the desired furylmethanol.

'H NMR (CDCl$_3$): 0.29 (s, 6H), 0.90 (s, 9H), 1.45 (brt, 1H), 4.59 (d, 2H, J=3.4 Hz), 6.49 (d, 1H, J =1.7 Hz) and 7.60 (d, 1H, J=1.7 Hz).

2-(tert-Butyldimethylsilyl)-3-hydroxymethyl-4-furaldehyde n-BuLi (a 1.6M solution in hexane; 2.7 ml, 4.28 mmol) was added dropwise to a solution of 3-(2-tert-butyldimethylsilyl)-furylmethanol (430 mg, 2.0 mmol) in dimethoxyethane (5 ml) at −78 degrees C. under argon. After stirring at 0 degrees C. for 15 minutes, lithium chloride (860 mg, 20.4 mmol), followed by N,N-dimethylformamide (0.35 ml, 4.48 mmol) was added. Stirring continued at 0 degrees C. for 16 hours and the mixture was quenched with ammonium chloride. Extraction with ethyl acetate and evaporation of the dried (magnesium sulfate) extracts gave a solid, which was recrystallized from hexane to give the titled aldehyde.

IR (CHCl$_3$) 3470, 1680, 1660, 1570 and 1510.
'H NMR (CDCl$_3$) 0.28 (s, 6H), 0.87 (s, 9H), 4.08 (t, 1H, J=7.3 Hz), 4.58 (d, 2H, J=7.3 Hz), 8.27 (s, 1H) and 9.90 (s, 1H).
$^{13}$CNMR (CDCl$_3$) 5.9, 17.1, 26.1, 55.4, 128.3, 133.9, 158.2, 158.3 and 186.6.
LRMS m/e (% abundance) 258 [(M+NH$_4$)$^+$,1], 240 (56), 223 (53), 184 (26), 183 (10) and 167 (41).

4-[2-(tert-Butyldimethylsilyl)-3-methyl]furylmethanol a) 3-(2-tert-Butyldimethylsilyl-4-carbonyl)furylmethyl methanesulfonate A solution of 2-(tert-butyldimethylsilyl)-3-hydroxymethyl-4-furaldehyde (4.98 g, 20.7 mmol), diisopropylethylamine (7.95 ml, 45.6 mmol) in tetrahydrofuran (70 ml) was added dropwise to a solution of methanesulfonyl chloride (6.42 ml, 82.9 mmol) in tetrahydrofuran (70 ml) at −20 degrees C. under argon. After stirring at −20 degrees C. for 90 minutes, the mixture was diluted with ethyl ether and washed successively with 10% hydrochloric acid, water and brine. Evaporation of the dried (magnesium sulfate) organic phase gave an oil, which was purified by flash chromatography on silica using 20% ethylacetate/hexane to give the titled mesylate.

'HNMR (CDCl$_3$) 0.36 (s, 6H), 0.93 (s, 9H), 3.16 (s, 3H), 5.33 (s, 2H), 7.27 (s, 1H), 8.26 (s, 1H) and 10.02 (s, 1H).

b) 4-[2-(tert-Butyldimethylsilyl)-3-methyl]furylmethanol

Lithium aluminum hydride (a 1.0M solution in THF; 62.2 ml, 62.2 mmol) was added dropwise to a solution of the mesylate from above in THF (10 ml) at −20 degrees C. under argon. After 20 minutes, TLC showed that the reaction has been completed. The mixture was quenched carefully with dil-hydrochloric acid. Extraction with diethyl ether and evaporation of the dried (magnesium sulfate) extracts gave an oil, which was purified by flash chromatography on silica using 20% ethylacetate/hexane to give the titled alcohol.

IR (CHCl$_3$) 3450 and 1600
'HNMR (CDCl$_3$) 0.27 (s, 6H), 0.91 (s, 9H), 2.12 (s, 3H), 4.53 (s, 2H) and 7.56 (s, 1H).
$^{13}$CNMR (CDCl$_3$) −6.1, 9.0, 17.5, 26.2, 55.4, 125.5, 130.8, 144.6 and 155.1
LRMS m/e (% abundance) 226 (M$^+$, 32), 209 (45), 170 (18), 169 (91), 142 (13), 141 (100), 101 (10) 97 (41), 75 (93) and 73 (22).

2-(tert-Butyldimethylsilyl)-3-methyl-4-furaldehyde

A solution of 4-[2-(tert-butyldimethylsilyl)-3-methyl]-furyl-methanol (380 mg, 1.68 mmol) in dichloromethane (5 ml) was added to a suspension of barium permanganate (6.45 g, 25.2 mmol) in dichloromethane (40 ml) at 0 degrees C. under argon. After stirring at room temperature for 15 hours, the mixture was filtered through celite. After concentration by evaporation, the filtrate was purified by flash chromatography on silica using 5% ethyl ether/hexane to give the titled aldehyde.

IR (CHCl$_3$) 2820, 2740 and 1680
'HNMR (CDCl$_3$) 0.2 (s, 6H), 0.82 (s, 9H), 2.23 (s, 3H), 8.09 (s, 1H) and 9.91 (s, 1H).
$^{13}$CNMR (CDCl$_3$) −6.3, 9.8, 17.3, 25.9, 128.1, 129.9, 156.8, 157.6 and 185.7.
LRMS m/e (% abundance) 224 (11), 168 (16), 167 (100), 83 (12) and 73 (11).

4-(1-Acetoxytridecyl)-2-(tert-butyldimethylsilyl)-3-methylfuran 2-(tert-Butyldimethylsilyl)-3-methyl-4-furaldehyde (95 mg, 0.42 mmol) was added to a solution of dodecylmagnesium bromide (a 1.0M solution in THF; 0.51 ml, 0.51 mmol) in THF (1 ml) at 0 degrees C. under argon. When all the aldehyde has reacted, acetic anhydride (80 microliter, 0.85 mmol) was added. After stirring at room temperature for 16 hours, the mixture was quenched with dilute hydrochloric acid. Extraction with diethyl ether and evaporation of the dried (magnesium sulfate) extracts gave an oil, which was purified by flash chromatography on silica using 5% ethyl ether/hexane to give the titled acetate.

IR (CHCl$_3$) 1730 and 1710.
'HNMR (CDCl$_3$) 0.26 (s, 6H), 0.88 (t, 3H, J=6.9 Hz), 1.25 (brs, 20H), 1.80 (m, 2H), 2.03 (s, 3H), 2.07 (s, 3H), 5.78 (t, 1H, J=7.0 Hz) and 7.52 (s, 1H)
$^{13}$CNMR (CDCl$_3$) −6.1, 9.5, 13.8, 17.5, 21.0, 22.5, 25.4, 26.2, 29.1, 29.2, 29.3, 29.4, 31.7, 34.6, 68.4, 125.4, 130.2, 144.4, 154.7 and 170.7
LRMS m/e (% abundance) 436(M$^+$, 4), 320 (3), 211 (14), 118 (10), 117 (100), 75 (22) and 73 (18).

4-(1-Acetoxytridecyl)-3-methyl-5-hydroxy-2(5H)-furanone (Compound 181)

A mixture of 4-(1-acetoxytridecyl)-2-(tert-butyldimethylsilyl 3-methylfuran (132 mg, 0.3 mmol), water (a few drops) and Rose Bengal (5 mg) in acetone (30 ml) was exposed to singlet oxygen at 0 degrees C. for 6 hours. The residue, on evaporation, was purified by flash chromatography on silica using 20% ethylacetate/hexane to give the titled furanone.

IR(CHCl)$_3$ 3400, 1780, 1750 and 1730.

$^1$HNMR (CHCl$_3$) 0.82 (t, 3H, J=6.9 Hz), 1.20 (brs, 20H), 1.75 (m, 2H), 1.85 (s, 3H), 2.03 (s, 3H), 2.06 (s, 3H), 5.35 (m, 2H), 5.88 (brs, 1H) and 6.08 (brs, 1H).

$^{13}$C NMR (CDCl$_3$) 9.2, 14.2, 20.8, 22.8, 25.6, 29.4, 29.5, 29.6, 29.7, 29.8, 32.1, 32.8, 70.1, 70.7, 97.7, 128.5, 128.9, 156.5, 156.6, 171.7, 172.1, 172.7 and 173.1.

LRMS m/e (% abundance) 355 (M+, 16), 296 (11), 295 (59), 294 (100), 277 (19), 267 (45), 126 (34), 125 (41), 112 (18), 95 (23), 81 (22) and 69 (27).

2-(tert-butyldimethylsilyl)-3-methyl-4-(1-phenylcarbamoyloxy)tridecylfuran and 2-(tert-butyldimethylsilyl)-3-methyl-4-[1-N-phenyl-N-phenylcarbamoyl)carbamoyloxy]tridecylfuran Dodecylmagnesium bromide (a 1.0M solution in THF; 0.89 ml, 0.89 mmol) was added to a solution of 2-tert-butyldimethylsilyl-3-methyl-4-furaldehyde (Compound 26, 200 mg, 0.89 mmol) in THF (5 ml) at 0 degrees C. under argon. After stirring at room temperature for 1 hour, the mixture was recooled to 0 degrees C. and phenylisocyanate (97 microliter, 0.89 mmol) was added. Stirring was continued for 5 minutes and the reaction mixture was quenched with ammonium chloride. Extraction with diethyl ether and evaporation of the dried (magnesium sulfate) extracts gave an oil. The crude product was purified by flash chromatography (SiO$_2$; 5% ethylether/hexane) to give the desired mono- and bis-phenylcarbonate. 2-(tert-Butyldimethylsilyl)-3-methyl-4-(1-phenylcarbamoyloxy)tridecylfuran: R$_f$(5% diethyl ether/hexane) 0.34; IR (CHCl$_3$) 3430, 1725, 1680, 1595 and 1515; $^1$HNMR (CDCl$_3$) 0.24 (s, 6H), 0.88 (t+s, 12H), 1.23 (m, 20H), 1.90 (m, 2H), 2.09 (s, 3H), 5.77 (t, 1H, J=7.0 Hz), 6.65 (s, 1H), 7.02 (t, 1H, J - 7.3 Hz), 7.25 (m, 2H), 7.35 (m, 2H) and 7.54 (s, 1H); $^{13}$CNMR (CDCl$_3$) −6.1, 9.6, 13.8, 17.5, 22.4, 25.4, 26.2, 29.1, 29.2, 29.3, 29.4, 31.7, 34.8, 69.5, 118.7, 123.5, 125.4, 129.2, 130.2, 138.2, 144.4, 153.4 and 154.9. 2-(tert-Butyldimethylsilyl)-3-methyl 4-[1-(N-phenyl-N-phenylcarbamoyl)carbamoyloxy]tridecylfuran: R$_f$ (5% diethylether/hexane) 0.23; $^1$H NMR (CDCl$_3$) 0.24 (s, 6H), 0.87 (s+t, 12H), 1.24 (m, 20H), 1.56 (m, 2H), 1.79 (s, 3H), 5.75 (t, 1H, J=6, 2Hz), 7.07 (t, 1H, J=8.0 Hz), 7.20 (m, 2H), 7.30 (m, 3H), 7.42 (m, 3H), 7.54 (m, 2H) and 10.9 (s, 1H); $^{13}$CNMR (CDCl$_3$) −6.2, −6.1, 9.3, 13.6, 17.5, 22.4, 24.9, 26.1, 28.8, 29.1, 29.2, 29.3, 29.4, 31.7, 34.4, 72.8, 120.0, 124.0, 124.1, 128.4, 128.9, 129.0, 129.5, 137.4, 138.0, 144.3, 151.8, 155.3 and 155.6.

5-Hydroxy-3-methyl-4-(1-phenylcarbamoyloxy)-tridecyl)-2(5H)furanone (Compound 182)

A mixture of 2-(tert-butyldimethylsilyl)-3-methyl-4-(1-phenylcarbamoyloxy)tridecylfuran (226 mg, 0.44 mmol), water (a few drops) and polymer bound Rose Bengal (0.077 g) in acetone (80 ml) was exposed to singlet oxygen at 0 degrees C. for 5 hours. The residue, on evaporation, was purified by flash chromatography (SiO$_2$, 20% ethylacetate/hexane) to give the titled furanone. IR (CHCl$_3$) 3400–3200, 1768, 1725, 1605 and 1520; $^1$HNMR (CDCl$_3$) 0.88 (t, 3H, J=6.9 Hz), 1.26 (m, 20H), 1.80 (m, 1H), 1.91 (s, 3H), 1.95 (m, 1H), 5.48 (brt, 1H), 5.52 (m, 1H), 5.95 (br, 1H), 6.04 (brs, 1H), 6.19 (brs, 1H), 7.00–7.40 (m, 6H); $^{13}$C NMR (CDCl$_3$) 8.7, 13.8, 22.4, 25.2, 28.9, 29.1, 29.2, 29.3, 29.4, 29.5, 31.7, 32.4, 32.5, 69.9, 70.6, 97.2, 97.4, 118.8, 119.0, 119.4, 123.9, 124.1, 128.1, 128.9, 129.2, 137.3, 137.6, 153.2, 153.4, 153.6, 156.0, 156.8, 172.5 and 172.7.

5-Methyl-2-triethylsilyl-4-furaldehyde n-Butyl lithium (a 1.6M solution in THF; 19.0 ml, 30.4 mmol) was added to a solution of morpholine (2.67 ml, 30.4 mmol) in THF (20 ml) at −78 degrees C. under argon. After 20 minutes, 3-furaldehyde (1.8 ml, 28.9 mmol) was added, followed by s-butyl-lithium (a 1.3M solution in cyclohexane; 23.4 ml, 30.4 mmol) after another 20 minutes. Stirring was continued for 2 hours and chlorotriethylsilane (5.1 ml, 30.4 mmol) was added. After 2 hours at −78 degrees C., s BuLi (23.4 ml, 30.4 mmol) was added, followed by iodomethane (5.4 ml, 86.9 mmol) after another 2 hours. The mixture was stirred at room temperature for 15 hours and quenched with ice cold dilute hydrochloric acid. Extraction with diethylether and evaporation of the dried (magnesium sulfate) extracts gave an oil, which was purified by flash chromatography on silica using 10% diethyl ether/hexane to give the titled aldehyde.

IR (CHCl$_3$) 1690.

$^1$HNMR (CDCl$_3$) 0.75 (q, 6H, J=8.0 Hz), 0.98 (t, 9H, J=8.0 Hz), 2.60 (s, 3H), 6.90 (s, 1H) and 9.90 (s, 1H).

$^{13}$CNMR (CDCl$_3$) 2.6, 6.7, 12.5, 118.8, 122.8, 158.5, 166.2 and 185.1; HRMS exact mass calculated for C$_{12}$H$_{20}$O$_2$Si 224.1232 found 224.1226

4-(1-Acetoxytridecyl)-5-methyl-2-triethylsilylfuran

5-Methyl-2-triethylsilyl-4-furaldehyde (145 mg, 0.65 mmol) was added to a solution of dodecylmagnesium bromide (a 1.0M solution in THF; 0.76 ml, 0.74 mmol) in THF at 0 degrees C. under argon. When all the aldehyde has consumed, acetic anhydride (0.1 6 ml, 1.71 mmol) was added. Stirring was continued at room temperature for 15 hours and the mixture was quenched with water. Extraction with diethyl ether and evaporation of the dried (magnesium sulfate) extracts gave an oil, which was purified by flash chromatography on silica using 5% diethyl ether/hexane to give the titled acetate.

IR (CHCl$_3$) 1730.

$^1$HNMR (CDCl$_3$) 0.75 (q, 6H, J=8.0 Hz), 0.88 (t, 3H, J=7.0 Hz), 0.95 (t, 9H, J=8.0 Hz), 1.25 (brs, 20H), 1.75 (m, 1H), 1.95 (m, 1H), 2.01 (s, 3H), 2.31 (s, 3H), 5.69 (t, 1H, J=7.2 Hz) and 6.55 (s, 1H).

$^{13}$CNMR (CDCl$_3$) −2.9, 7.0, 11.9, 13.8, 21.0, 22.5, 25.3, 25.7, 29.0, 29.2, 29.3, 29.4, 31.7, 34.8, 68.8, 118.8, 120.3, 154.1, 156.1 and 170.7. LRMS m/e (% abundance) 436 (M+, 9), 377 (22), 376 (33), 347 (43), 239 (29), 145 (100), 115 (34), 103 (30) and 87 (30); HRMS Exact Mass Calculated For C$_{26}$H$_{48}$O$_3$Si (M+) 43 6.3373, found 436.3374.

4-(1-Acetoxytridecyl)-5-hydroxy-5-methyl-2-furanone (Compound 180)

A mixture of 4-(1-acetoxytridecyl)-5-methyl-2-triethylsilylfuran (231 mg, 0.53 mmol), water (a few drops) and Rose Bengal (6.3 mg) in acetone (100 ml) was exposed to singlet oxygen at 0 degrees C. for 3 hours. The residue, after evaporation, was purified by flash chromatography on silica using 10% ethylacetate/hexane to give the titled furanone. This compound is a mixture of epimers which isomerizes upon standing.

IR (CHCl$_3$) 3600–3200, 1770 and 1740.

For further physical data of Compound 180 see the description of preparing the same compound as above.

5-Methyl-2-triethylsilyl-4-(1-phenylcarbamoyloxy)-tridecylfuran

A solution of 5-methyl-2-triethylsilyl-4-furaldehyde (219 mg, 0.98 mmol) in THF (5 ml) was added to a solution of dodecylmagnesium bromide (a 1.0M solution in THF; 1.08 ml; 1.08 mmol) in THF at 0 degrees C. under argon. When all the aldehyde was consumed, phenylisocyanate (0.12 ml, 1.08 mmol) was added. After stirring at room temperature for 16 hours, the mixture was quenched with dilute hydrochloric acid. Extraction with diethyl/ether and evaporation of the dried (magnesium sulfate) extracts gave an oil, which was purified by flash chromatography on silica using 5% diethyl/ether/hexane to give the titled furan.

IR (CHCl$_3$) 3440, 1730 and 1520.

'HNMR (CDCl$_3$) 0.72 (q, 6H, J=6.6 Hz), 0.88 (t, 3H, J=6.6 Hz), 0.98 (t, 9H, J=6.6 (Hz), 1.25 (brs, 20H), 1.75 (m, 1H), 1.95 (m, 1H), 2.36 (s, 3H), 5.70 (t, 1H, J=7.3 Hz), 6.57 (s, 1H), 6.62 (br, 1H), 7.02 (m, 1H), 7.29 (m, 2H) and 7.37 (m, 2H).

$^{13}$CNMR (CDCl$_3$) 2.9, 7.1 11.9, 13.8, 22.5, 25.3, 29.1, 29.2, 29.3, 29.4, 31.7, 35.0, 69.9, 118.7, 118.8, 120.2, 123.3, 129.1, 138.3, 144.8, 153.5, 154.3 and 156.3.

5-Methyl-5-hydroxy-4-(1-phenylcarbamoyloxy)tridecyl-2-furanone (Compound 183)

A mixture of 5-methyl-2-triethylsilyl-4-(1-phenylcarbamoyloxy) tridecylfuran (80 mg, 0.13 mmol) water (a few drops) and Rose Bengal (ca, 3 mg) in acetone (60 ml) was exposed to singlet oxygen at 0 degrees C. for 4 hours. The residue, after evaporation, was purified by flash chromatography on silica using 20% ethylacetate/hexane to give the titled furanone.

IR (CHCL$_3$) 3440, 3400–3240, 1765, 1730, 1600 and 1525.

'HNMR (CDCl$_3$) 0.88 (t, 3H, J - 6.9 Hz), 1.26 (brs, 20H), 1.67 (brm, 2H), 1.79 (brs, 3H), 5.18 (brm, 1H), 5.50 (brm, 1H), 5.85 (br, 1H), 6.03 (br, 1H), 7.12 (m, 2H) and 7.40 (m, 3H).

$^{13}$CNMR (CDCl$_3$) 13.8, 22.4, 22.8, 24.2, 24.3, 24.8, 25.1, 28.9, 29.1, 29.2, 29.3, 29.4, 31.7, 33.3, 34.0, 69.6, 70.2, 70.3, 98.2, 106.5, 118.1, 119.2, 124.1, 124.3, 124.5, 129.3, 136.9, 153.9, 169.9 and 170.4.

LRMS m/e (% abundance) 431 (M+, 4), 277 (7), 153 (6), 137 (12), 126 (12), 119 (25), 109 (11), 94 (13), 93 (100) and 55 (30).

5-Butyl-2-triethylsilyl-4-furaldehyde

Using the same procedure as for 5-methyl-2-trimethylsilyl-4-furaldehyde but substituting 2-trimethylsilyl-4-furaldehyde and methyl iodide with 2-triethylsilyl-4-furaldehyde and 1-iodobutane, respectively, gives 5-butyl-2-triethylsilyl-4-furaldehyde. IR (neat) 1690 cm$^{-1}$; 'HNMR (CDCl$_3$) 0.73 (q, 6H, J=8.4 Hz), 0.95 (m, 12H), 1.36 (p, 2H, J=7.5 Hz), 1.69 (p, 2H, J=7.5 Hz), 2.94 (t, 2H, J=7.5 Hz), 6.89 (s, 1H) and 9.91 (s, 1H) $^{13}$ CNMR (CDCl$_3$): 3.03, 7.17, 13.6, 22.2, 26.8, 30.4, 118.6, 122.5 158.4, 170.2 and 184.8. LRMS m/e (% abundance) 266 (M+, 20) 238 (20) 237 (100), 87 (10) and 75 (20); HRMS exact mass calculated for C$_{15}$H$_{26}$O$_2$S; 266.1702, found 266.1690.

5-Butyl-5-hydroxy-4-(1-phenylcarbamoyloxy)tridecyl-2-furanone (Compound 184)

a) 5-Butyl-4-(1-phenylcarbamoyloxy)tridecyl-2-triethylsilylfuran

Dodecyl magnesium bromide (a 1.0M solution in THF; 0.25 ml, 0.25 mmol) was added to a solution of 5-butyl-2-triethylsilyl-4-furaldehyde (59 mg, 0.22 mmol) in THF (1 ml) at 0 degrees C. under argon. When all the aldehyde has reacted, phenylisocyanate (27 microliter, 0.25 mmol) was added and stirring was continued at −40 degrees C. for 14 hours. Without purification the crude product was used in the next step.

'HNMR (CDCl$_3$).

b) 5-Butyl-5-hydroxy-4-(1-phenylcarbamoyloxy)tridecyl-2-furanone (Compound 184)

Water (a few drops) and Rose Bengal (ca. 3 mg) were added to the above reaction mixture. The mixture was exposed to singlet oxygen for 3 hours at 0 degrees C. The residue, after evaporation, was purified by preparative TLC (SiO$_2$) developed with 40% diethylether/hexane to give the titled furanone. IR (CHCl$_3$) 3600–3240, 3440, 1770, 1760, 1730, 1605, 1550 and 1530. 'HNMR (CDCl$_3$) 0.88 (m, 6H), 1.30 (brm, 22H), 1.50 (m, 2H), 1.75 (m, 2H), 2.00 (m, 2H), 5.10 (brm, 1H), 5.70 (br, 1H), 6.04 (brs, 1H), 6.95 (brs, 1H), 7.15 (brm, 1H), 7.30 (m, 3H) and 7.50 (m, 2H)

$^{13}$C NMR (CDCl$_3$) 13.6, 13.8, 22.1, 2.22, 22.4, 24.3, 24.6, 25.1, 28.6, 28.9, 29.0, 29.1, 29.3, 29.4, 31.7, 32.9, 33.5, 36.3, 69.7, 108.3, 118.9, 119.2, 119.4, 120.2, 124.5, 128.6, 129.0, 129.2, 129.3, 129.4, 136.8, 169.2, 169.7 and 169.9. LRMS m/e (% abundance) 491[(M+NH$_4$)+, 67], 474[(M+H)+, 86], 473 (M+, 23), 456 (33), 372 (30), 354 (30), 337 (66), 319 (38), 272 (48), 213 (80), 120 (27) 119 (45), 94 (58) and 93 (100).

2-tert-Butyldimethylsilyl-3,5-dimethyl-4-furaldehyde

Treatment of 2-tert-butyldimethylsilyl-4-hydroxymethyl-3-methylfuran with n-butyl lithium and iodomethane gives 2-tert-butyldimethylsilyl-3,5-dimethyl-4-hydroxymetylfuran. Oxydation of this furan with barium permanganate gives the titled furaldehyde.

2-Triethylsilyl-5-phenyl-4-furaldehyde

Treatment of 2-triethylsilyl-4-furaldehyde with lithio N,N,N'-trimethylethylenediamine, followed by phenyl trifluoromethanesulfonate in the presence of anhydrous zinc chloride and tetrakis (triphenylphosphine) palladium (O) provides the titled aldehyde.

Ethyl-4-phenyl-3-furoate (Adapted from: Liotta, D.; Saindane, M.; Ott, W. *Tet. Lett.* (1983) 24, 2473.)

A mixture of 4-phenyloxazole 500 mg, 3.45 mmol) and ethyl phenyl propiolate (630 mg, 3.62 mmol) were heated in a sealed tube for 16 hours at 210 degrees with stirring. The residue was filtered through silica using 5% ethyl ether/hexanes to give the titled oxazole, 664 mg of a pale oil, which was used without further purification. The starting 4-phenyloxazole was prepared according to Bredereck, H.; Gompper, R. *Chem. Ber.* (1945), 87, 700.

4-Phenyl-3-furan methanol

LiAlH$_4$ (1.0M solution in hexane 1.14 ml, 1.14 mmol) was added dropwise to a solution of ethyl-4-phenyl-3-furoate (246 mg, assumed 1.28 mmol) in tetrahydrofuran (20 ml) at 0 degrees under argon. The solution was stirred and was allowed to warm to room temperature gradually over ¼ hour. The mixture was quenched with saturated ammonium chloride and the organics were extracted into ethyl ether, and washed with H$_2$O. Evaporation of the dried (magnesium sulfate) extracts gave an oil, which was purified by flash chromatography on silica using 20% ethyl acetate/hexanes. This was further purified by recrystallization (hexane/ethyl ether) to give the title compound as pale yellow crystals.

IR (CHCl$_3$): 3600 v. br., 3000 cm$^{-1}$.

$^1$H NMR (CDCl$_3$): 1.90 (brs, 1H), 4.60 (brs, 2H), 7.22 to 7.60 (m, 7H).

$^{13}$C NMR (CDCl$_3$): 55.4, 124.1, 126.4, 127.4, 127.9, 128.9, 132.2, 140.4, 142.3.

HRMS: exact mass calculated for C$_{11}$H$_{10}$O$_2$(M$^+$) 174.0680, found 174.0696.

4-Phenyl-3-furaldehyde

A mixture of 4-phenyl-3-furanmethanol (458 mg, 2.63 mmol), powdered 4A molecular sieves (500 mg), 4-methyl-morpholine-N-oxide (462 mg, 3.95 mmol) and tetrapropylammonium perruthenate (46 mg, 0.13 mmol) in anhydrous dichloromethane (40 ml) were stirred at room temperature for 3 hours. Residue was filtered through silica and concentrated to a brown oil which was purified by flash chromatography on silica using 10% ethyl ether/hexanes to give the titled aldehyde.

IR (CHCl$_3$): 3020, 1690 cm$^{-1}$.

$^1$H NMR (CDCl$_3$): 7.30 to 7.55 (m, 5H); 7.59 (d, J - 1.6 Hz, 1H); 8.15 d, J=1.6 Hz, 1H); 9.94 (s, 1H).

$^{13}$C NMR (CDCl$_3$): 125.8, 126.1, 128.0, 128.6, 128.7, 130.0, 142.0, 152.6, 185.2.

HRMS: exact mass calculated for C$_{11}$H$_8$O$_2$(M$^+$) 172.0524 observed 172.0520.

3(-1-Acetoxytridecyl)-4-phenylfuran

Dodecylmagnesium bromide (a 1.0M solution in THF; 2.11 ml, 2.11 mmol) was added to a solution of 4-phenyl-3-furaldehyde (303 mg, 1.76 mmol) in THF at 0 degrees under argon and gradually allowed to warm to room temperature with stirring. When all of the aldehyde was consumed acetic anhydride (719 mg, 7.04 mmol) was added and stirring was continued for 2 hours more. The reaction was quenched with saturated ammonium chloride and the organics were extracted into ethyl ether. The combined fractions were washed with saturated sodium bicarbonate, water and brine, dried over magnesium sulfate and concentrated to a yellow oil which was purified by flash chromatography on silica using 3% ethyl ether hexanes to give the title compound.

IR (CHCl$_3$): 3020, 1725 cm$^{-1}$.

$^1$H NMR (CDCl$_3$): 0.88 (t, J=6.6 Hz, 3H); 1.10 to 1.40 (m, 20H); 1.53 to 1.78 (m, 2H); 2.00 (s, 3H); 5.92 (t, J=6.8 Hz, 1H); 7.27 to 7.46 (m, 7H).

$^{13}$C NMR (CDCl$_3$): 13.8, 20.9, 22.4, 25.1, 28.9, 29.1, 29.26, 29.36, 29.41, 31.7, 34.4, 68.5, 124.6, 126.3, 127.4, 128.6, 128.8, 132.4, 140.6, 141.5, 170.5.

HRMS: exact mass calculated for C$_{25}$H$_{36}$O$_3$ (M$^+$) 384.2667, observed 384.2672.

4-(-1-Acetoxytridecyl)-5-hydroxy-3-phenyl-2(5H)-furanone

3-(-1-Acetoxytridecyl)-5-hydroxy-4-phenyl-2(5H)-furanone

A mixture of 3-(-1-acetoxytridecyl)-4-phenylfuran (506 mg, 1.32 mmol), water (a few drops) and Rose Bengal on polymer beads (1.6 g) in THF was exposed to singlet oxygen at 0 degrees C. for 3 hours. The Rose Bengal was filtered off and the residue was concentrated to a pink oil which was purified by flash chromatography on silica using 5 to 20% ethyl acetate/hexanes to give the title furanones as a mixture of isomers. The isomers were separated by HPLC chromatography on reverse phase Vydac column using 15% water/acetonitrile.

3-(-1-acetoxytridecyl)-5-hydroxy-4-phenyl-2(5H)-furanone (retention time: 26.3 minutes).

IR (CDCl$_3$): 3020, 1760 cm$^{-1}$.

$^1$H NMR (CDCl$_3$): 0.88 (t, J=6.7 Hz, 3H); 1.15 to 1.45 (m, 20H); 1.83 (s, 3H); 1.77 to 1.92 (m, 1H); 1.92 to 2.07 (m, 1H); 5.59 (d, J=5.4 Hz 0.5 H); 5.62 (d, J =5.4 Hz, 0.5 H); 6.31 (s, 1H); 7.40 to 7.54 m(5H).

$^{13}$C NMR (CDCl$_3$): 13.9, 20.3, 22.5, 25.4, 28.9, 29.16, 29.23, 29.34 29.41, 29.45, 31.7, 32.6, 68.9, 97.6, 128.5, 128.7, 128.9, 130.2, 130.4, 157.9, 169.6, 171.1.

LRMS m/z calculated for C$_{25}$H$_{40}$O$_5$(M+NH$_4$)=434. Observed 434.

4-(-1-acetoxytridecyl)-5-hydroxy-3-phenyl-2(5H)-furanone (retention time 28.0 minutes).

IR (CHCl$_3$): 3010, 1765 (v. br.)cm$^{-1}$.

$^1$H NMR (CDCl$_3$): 0.88 (t, J=6.5 Hz, 3H); 1.12 to 1.40 (m, 20H); 1.81 (s, 3H); 170 to 185 (m, 1H); 1.85 to 2.00 (m, 1H); 5.62 (d, J=5.1 Hz, 0.5 H); 5.65 (d, J=5.0 Hz, 0.5 H); 6.17 (s, 1H); 7.33 to 7.50 (m, 5H).

$^{13}$C NMR (CDCl$_3$): 13.8, 20.1, 22.4, 25.3, 28.8, 29.1, 29.2, 29.3, 29.4, 31.7, 33.0, 70.3, 97.2, 128.6, 128.9, 129.4, 131.1, 156.8, 170.7, 171.3.

LRMS m/Z calculated for C$_{25}$H$_{40}$O$_5$ (M+NH$_4$)—434, observed 434.

2-Methyl-4-phenyl-3-furaldehyde n-Butyllithium (a 1.6m solution in hexane, 2.43 ml, 3.89 mmol) was added to a solution of trimethylethylenediamine (397 mg, 3.89 mmol) in tetrahydrofuran (25 ml) at 0 degrees under argon. After 20 minutes the solution was cooled to −78 degres and 4-phenyl-3-furaldehyde (608 mg, 3.35 mmol) was added. This mixture was allowed to gradually warm to −20 degrees and stirred for 1¼ hours, then recooled to −78 degrees before n-butyllithium (a 1.6M solution in hexane, 2.43 ml, 3.89 mmol) was added dropwise. The stirring mixture was again gradually warmed to −20 degrees and stirred for 2 hours before iodomethane (2.56 g 17.67 mmol) was added. After stirring for 18 hours at −20 degrees the reaction was quenched with ice-cold 10% (v/v) hydrochloric acid and the organics were extracted into ethyl ether. The combined fractions were washed with saturated sodium bicarbonate, H$_2$O and brine. Evaporation of the dried (magnesium sulfate) extracts gave an oil which was purified by flash chromatography on silica using 20% ethyl ether/hexanes to give the title aldehyde.

IR (CHCL$_3$): 3600, 1690 cm$^{-1}$.

$^1$H NMR (CDCl$_3$): 2.65 (s, 3H); 7.30 to 7.50 (m, 6H); 1.02 (s, 1H).

$^{13}$C NMR (CDCl$_3$): 13.4, 119.8, 127.2, 128.0, 128.7, 129.0, 130.6, 138.3, 162.3, 186.7.

HRMS: exact mass calculated for C$_{12}$H$_{10}$O$_2$ (M+) 186.0680, found 186.0689.

2-Methyl-4-phenyl-3-furanmethanol

LiAlH$_4$ (1.0M solution in hexane, 0.12 ml, 0.12 mmol) was added dropwise to a solution of 2-methyl-4-phenyl-3-furaldehyde (45 mg, 0.24 mmol) in tetrahydrofuran (3 ml) at 0 degrees under argon. After 10 minutes the reaction was quenched with saturated ammonium chloride and the organics were extracted into ethyl ether. The combined fractions were washed with H$_2$O and brine and the dried (magnesium sulfate) extracts were concentrated to a yellow oil which was carried on without further purification.

IR (CHCl$_3$): 3620, 3450 (v. broad), 3005 cm$^{-1}$.

$^1$H NMR (CDCl$_3$): 2.38 (S, 3H); 4.56 (s, 2H); 7.25 to 7.60 (m, 6H);

$^{13}$C NMR (CDCl$_3$): 11.5, 54.8, 117.9, 127.2, 127.5, 128.1, 128.9, 132.7, 137.4, 151.9.

HRMS exact mass calculated for C$_{12}$H$_{12}$O$_2$ (M+) 188.0837, found 188.0850.

3-Dodecoyloxymethyl-2-methyl-4-phenylfuran

To a stirred solution of 2-methyl-4-phenyl-3-furanmethanol (48 mg, 0.26 mmol) and triethylamine (39 mg. 0.38 mmol) in tetrahydrofuran (3 ml) at 0 degrees under argon was added lauroyl chloride (73 mg. 0.33 mmol). This solution was warmed gradually to room temperature and stirred for 4½ hours. The organics were extracted into ethyl ether and washed with a 5% aqueous sodium bicarbonate solution, H$_2$O and brine. Evaporation of the dried (magnesium sulfate) extracts gave an oil which was purified by flash chromatography on silica using 3% ether/hexanes to give the title compound.

IR (CHCl$_3$): 3010, 1725 cm$^{-1}$.

$^1$H NMR (CDCl$_3$): 0.86 (t, J=6.7 Hz, 3H); 1.20 to 1.32 (m, 16H); 1.50 to 1.64 (m, 2H); 2.23 to 2.32 (m, 2H); 2.36 (s, 3H); 4.97 (s, 2H); 7.29 to 7.42 (m, 6H).

$^{13}$C NMR (CDCl$_3$) 11.7, 13.9, 22.5, 24.7, 28.9, 29.06, 29.12, 29.3, 29.4, 31.7, 34.2, 56.5, 113.7, 127.3, 127.9, 128.1, 128.8, 132.5, 137.6, 153.3, 174.1.

4-Dodecoyloxymethyl-5-hydroxy-5-methyl-3-phenyl-2-furanone (Compound 185)

A mixture of 3-dodecoyloxymethyl-2-methyl-4-phenylfuran (40 mg, 0.11 mmol), water (a few drops) and Rose Bengal on polymer beads (240 mg) in tetrahydrofuran (40 ml) was exposed to singlet oxygen at 0 degrees for 3 hours. The Rose Bengal was filtered off and the residue was concentrated to a pink oil which was purified by flash chromatography on silica using 15% ethyl acetate/hexanes. The furanone was further purified by HPLC chromatography on a normal phase partisil 10 column using 15% ethyl acetate/hexanes to give the title compound.

IR (CHCl$_3$): 3020, 1765, 1740 cm$^{-1}$.

$^1$H NMR (CDCl$_3$): 0.85 (t, J=6.7 Hz, 3H): 1.10 to 1.21 (m, 16H); 1.35 to 1.49 (m, 2H); 1.77 (s, 3H); 2.11 (t, J=7.6 Hz, 2H); 3.70 to 3.90 (brs, 1H); 5.02 (s, 2H); 7.37 to 7.50 (m, 5H).

$^{13}$C NMR (CDCl$_3$): 13.9, 22.5, 24.0, 24.4, 28.9, 29.0, 29.1, 29.2, 29.4, 31.7, 33.6, 57.2, 104.4 128.4, 128.7, 129.4, 129.8, 131.4, 154.4, 169.0, 173.9.

HRMS: exact mass calculated for C$_{24}$H$_{35}$O$_5$(MH+) 403.2484, found 403.2497.

5-Methyl-2-triethylsilyl-4-furanmethanol

LiAlH$_4$ (1.0M solution in hexane, 0.51 ml, 0.51 mmol) was added dropwise to a solution of 5-methyl-2-triethylsilyl-4-furaldehyde (230 mg, 1.03 mmol) in tetrahydrofuran (15 ml) at 0 degrees under argon. The stirring solution was allowed to warm to room temperature gradually over ¼ hour. The reaction was quenched with 10% aqueous HCl and the organics were extracted into ethyl ether. The combined fractins were washed with H$_2$O and brine. Evaporation of the dried (magnesium sulfate) extracts gave an oil which was purified by filtration through silica using 10% ethyl ether/hexanes to give the title compound.

IR (CHCl$_3$): 3610 (sharp), 3440 (broad), 2940 cm$^{-1}$.

$^1$H NMR (CDCl$_3$): 0.71 (q, J=7.7 Hz, 6H); 0.96 (t, J=7.7 Hz, 9H); 2.25 (s, 3H); 2.40 (brs, 1H); 4.38 (s, 2H); 6.59 (s, 1H).

$^{13}$C NMR (CDCl$_3$): 2.9, 11.5, 56.2, 118.9, 122.3, 153.7, 156.0.

4-Dodecoyloxymethyl-5-methyl-2-triethylsilylfuran

To a stirred solution of 5-methyl-2-triethylsilyl-4-furanmethanol (208 mg. 0.92 mmol) and triethylamine (121 mg, 1.20 mmol) in tetrahydrofuran (10 ml) at 0 degrees under argon was added lauroyl chloride 302 mg, 1.38 mmol). This solution was allowed to warm gradually to room temperature and quenched with a 10% aqueous HCl solution. The organics were extracted into hexanes and the combined fractions were washed with a saturated aqueous solution of sodium bicarbonate, H$_2$O and brine. Evaporation of the dried (magnesium sulfate) extracts gave an oil which was purified by filtration through silica using 2% ethyl ether/hexanes to give the title compound.

IR (CHCl$_3$): 1725 cm$^{-1}$.

$^1$H NMR (CDCl$_3$): 0.75 (q, J=7.7 Hz, 6H); 0.88 (t, J=6.7 Hz, 3H), 0.98 (t, J=7.7 Hz, 9H); 1.20 to 1.35 (m, 16H); 1.56 to 1.68 (m, 2H); 2.30 (t, J=7.5 Hz, 2H); 2.31 (s, 3H); 4.91 (s, 2H): 6.57 (s, 1H).

$^{13}$C NMR (CDCl$_3$): 2.9, 7.0, 11.7, 13.8, 22.6, 24.8, 28.9, 29.08, 29.14, 29.3, 29.4, 31.7, 34.2, 57.9, 114.7, 122.9, 155.3, 156.3, 174.2.

4-Dodecoyloxymethyl-5-hydroxy-5-methyl-2-furanone (Compound 186)

A mixture of 4-dodecoyloxymethyl-5-methyl-2-triethylsilylfuran (180 mg. 0.44 mmol), water (a few drops) and Rose Bengal on polymer beads (360 mg) in tetrahydrofuran (70 ml) was exposed to singlet oxygen at 0 degrees until no starting material was visible (via TLC). The Rose Bengal was filtered off and the residue was concentrated to a pink oil which was purified by flash chromatography on silica using 30% ethyl acetate/hexanes to give the titled furanone.

IR (CHCl$_3$): 3400 (v. broad), 1750 (strong) cm$^{-1}$.

$^1$H NMR (CDCl$_3$) 0.88 (t, J=6.7 Hz 3H); 1.20 to 1.37 (m, 16H); 1.59 to 1.70 (m, 2H); 1.72 (s, 3H); 2.40 (t, J=7.6 Hz, 2H); 3.20 to 4.40 (v. brs, 1H); 4.93 (s, 2H); 5.94 (s, 1H).

$^{13}$C NMR (CDCl$_3$) 13.8, 22.4, 23.7, 24.5, 28.8, 28.9, 29.0, 29.2, 29.3, 31.6, 33.7, 58.4, 105.9, 117.0, 166.2, 170.3, 173.7.

3-Phenyl-2-triethylsilyl-4-furaldehyde n-Butyllithium (a 1.42M solution in hexane, 2.33 ml, 3.31 mmol) was added to a solution of 1-methylpiperazine (331 mg. 3.31 mmol) in tetrahydrofuran (15 ml) at 0 degrees under argon. After 15 minutes the solution was cooled to −78 degrees and 4-phenyl-3-furaldehyde (517 mg, 3.01 mmol) was added. This mixture was warmed to 0 degrees and stirred for 15 minutes, then recooled to −78 degrees before sec-butyllithium (a 1.3M solutin in cyclohexane, 2.77 ml, 3.61 mmol) was added dropwise. This solution was stirred 12 hours at −78 degrees C. before chlorotriethylsilane (1.81 g, 12.02 mmol) was added. The mixture was allowed to warm gradually to room temperature and stirred an additional 1¼ hours. The reaction was quenched with ice-cold 5% (V/V) hydrochloric acid and the organics were extracted into ethyl ether. The combined fractions were washed with saturated sodium bicarbonate, $H_2O$ and brine. Evaporation of the dried (magnesium sulfate) extracts gave an oil which was purified by flash chromatography on silica using 10% ethyl acetate/hexanes to give the title aldehyde.

IR (heat): 2952, 1691 cm:

$^1$H NMR (CDCl$_3$): 0.62 (q, J=7.8 Hz, 6H); 0.85 (t, J=7.8 Hz, 9H); 7.20 to 7.43 (m, 5H); 8.30 (s, 1H); 9.79 (s, 1H).

$^{13}$C NMR (CDCl$_3$): 3.0, 6.8, 127.1, 128.2, 130.2, 131.8, 136.5, 153.7, 158.3, 186.1.

3-Phenyl-2-triethylsilyl-4-furanmethanol

LiAlH$_4$ (1.0M solution in hexane, 1.48 ml, 1.48 mmol) was added dropwise to a solution of 3-phenyl-2-triethylsilyl-4-furaldehyde (422 mg, 1.48 mmol) in tetrahydrofuran (10 ml) at 0 degrees under argon. This mixture was warmed to room temperature, quenched wtih ice-cold 5% (V/V) hydrochloric acid and the organics were extracted into ethyl ether. The combined fractions were washed with saturated sodium bicarbonate, $H_2O$ and brine. The dried extracts (magnesium sulfate) were concentrated to an oil which was purified by flash chromatography on silica using 20% ethyl acetate/hexanes to give the title compound. IR (neat): 3300 (broad); 2953 cm$^{-1}$.

$^1$H NMR (CDCl$_3$): 0.59 (q, J=8.0 Hz, 6H); 0.85 (t, J=8.0 Hz, 9H); 1.60(brs, 1H); 4.42 (brs, 2H); 7.29 to 7.40 (m, 5H); 7.68 (s, 1H).

$^{13}$C NMR (CDCl$_3$): 3.2, 6.9, 55.2, 125.2, 127.6, 128.2, 130.0, 133.7, 137.5, 144.9, 155.7.

4-Dodecoyloxymethyl-3-phenyl-2-triethylsilylfuran

To a stirred solution of 3-phenyl-2-triethylsilyl-4-furanmethanol (345 mg, 1.20 mmol) and triethylamine (182 mg, 1.80 mmol) in tetrahydrofuran (15 ml) at 0 degrees under argon was added lauroyl chloride (786 mg, 3.60 mmol). This solution was allowed to warm gradually to room temperature. After stirring an additional 2 hours the white precipitate was filtered off. The filtrate was taken up into ethyl ether, washed with saturated ammonium chloride, saturated sodium bicarbonate, $H_2O$ and brine. Evaporation of the dried (magnesium sulfate) extracts gave an oil which was purified by flash chromatography on silica using 2% ethyl ether/hexanes to give the title compound.

IR (neat): 1737 cm$^{-1}$.

$^1$H NMR (CDCl$_3$) 0.60 (q, J=8.1 Hz, 6H); 0.81 to 0.93 (m, 12H), 1.19 to 1.35 (m, 16H): 1.48 to 1.61 (m, 2H): (m, 2H): 2.23 (t, J=7.5 Hz, 2H): 4.86 (s, 2H): 7.25 to 7.40 (m, 5H); 7.72 (S, 1H).

$^{13}$C NMR (CDCl$_3$) 3.17, 6.90, 13.8, 22.5, 24.7, 28.9, 29.0, 29.1, 29.2, 29.4, 31.7, 34.1, 56.4, 120.5, 127.6, 128.1, 130.1, 133.3, 138.0, 146.4, 155.6, 173.8.

4-Dodecoyloxymethyl-5-hydroxy-3-phenyl-2(5H)-furanone

A mixture of 4-dodecoyloxymethyl-3-phenyl-2-triethylsiylfuran (256 mg, 0.54 mmol), water (a few drops) and Rose Bengal on polymer beads (1.0 g) in tetrahydrofuran was exposed to singlet oxygen at 0 degrees for 3 hours. The Rose Bengal was filtered off and the residue was concentrated to a pink oil which was purified by flash chromatography on silica using 20% ethyl acetate/hexanes to give the title compound.

IR (CHCl$_3$): 3400 (v. broad), 1743 cm$^{-1}$.

$^1$H NMR (CDCl$_3$): 0.88 (t, J=6.6 Hz, 3H); 1.05 to 1.45 (m, 16H); 1.50 to 1.63 (m, 2H); 2.25 (t, J=7.6 Hz, 2H); 5.04 (S, 1H); 5.07 (S, 1H); 5.37 to 5.50 (brs, 1H); 6.22 (S, 1H); 7.40 to 7.54 (m, 5H).

$^{13}$C NMR (CDCl$_3$): 14.1, 22.6, 24.6, 29.0, 29.2, 29.3, 29.4, 29.5, 31.8, 33.8, 57.5, 96.5, 96.6, 128.1, 128.6, 129.1, 129.6, 131.7, 152.6, 170.5, 173.6.

EXAMPLE 18

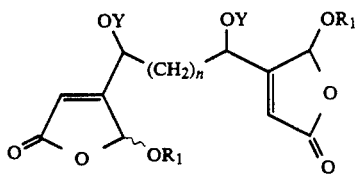

Formula 21

Compounds which are preferred in the method of treatment of the present invention and which are shown by Formula 21 above have the following preferred substituents. With respect to the 5-position of the furanone moiety the preferred compounds are those where the substituent is hydroxy (in Formula 21 R$_1$ is H), acetoxy (R$_1$ is COCH$_3$), or where R$_1$ is CONHR$_2$ and R$_2$ is lower alkyl or phenyl, more preferably phenyl.

With reference to the length of the alkyl chain which connects the two 5-hydroxy-2(5H)-furanone rings of the compounds of Formula 21, the alkyl chain may contain between approximately 10 to 16 carbons (n is an integer between 8 to 14); particularly preferred are the compounds where the chain has 12 or 14 carbons (n is 10 or 12).

With reference to the Y susbtituent, compounds are preferred where Y is H, straight or branch chained lower alkanoyl having 1 to 6 carbons, and where Y is CONHR$_3$, particularly where R$_3$ is phenyl.

Examples of preferred compounds of the invention are listed below with reference to Formula 21, Compound 200 n=12, Y=CH$_3$—CO, R$_1$=H;
Compound 201 n=10, Y=NH—Ph—CO, R$_1$=H;
Compound 202 n=12, Y=C(CH$_3$)$_3$—CO, R$_1$=H;
Compound 203 n=12, Y=C(CH$_3$)$_3$—CO, R$_1$=CONH—Ph.

The compounds of Example 18 can be made in accordance with the synthetic chemical pathways illustrated by the following specific examples. The practicing synthetic organic chemist can readily modify the chemical pathways provided by these specific reactions and examples to prepare any and all compounds represented by Formula 21.

1.14-Diacetoxy-1,14-bis(2-Triethylsilyl-4-furyl)tetradecane

2-Triethylsilyl-4-furaldehyde (530 mg, 2.52 mmol) was added to a solution of 1,12-dodecylmagnesium bromide (1.26 mmol; prepared from 414 mg 1,12-dibmmododecane and 77 mg magnesium twinings) in THF (3 ml) at 0° C. under argon. When all the aldehyde was combined, acetic anhydride (0.71 ml, 7.57 mmol) was added. After stirring at rooom temperature for 14 hours the mixture was quenched with water. Extraction (ethyl ether) and evaporation of the dried (magnesium sulfate) extracts gave an oil, which was purified by flash chromatography on silica using (10% ethyl ether/hexane to give the titled ester. IR (CHCl$_3$) 1725.

$^1$HNMR (CDCl$_3$) 0.76 (t, 12H, J=7.6 Hz), 0.98 (t, 18H, J=7.6 Hz), 1.24 (br, 20H), 1.95 (m, 4H), 2.04 (s, 6H0, 5.78 (t, 2H, J=7.3 Hz), 6.59 (s, 2H) and 7.60 (s, 2H).

$^{13}$C NMR (CDCl$_3$) 2.87, 6.94, 21.0, 25.2, 27.1, 29.0, 29.2, 29.3, 29.4, 32.7, 34.6, 63.3, 68.5, 119.8, 125.0, 144.7, 159.5 and 178.

HRMS exact mass calculation for C$_{38}$H$_{66}$O$_6$Si$_2$(M+), 674.4398, found 674.4389.

1,14-Diacetoxy-1,14-bis[5-hydroxy-2(5H)-4-furanoyl]-tetradecane Compound 200

A mixture of 1,14-diacetoxy-1,14-bis(2-triethylsilyl-4-furyl)tetradece (298 mg, 0.43 mmol) Rose Bengal (ca. 5 mg) and water (1 ml) in acetone (20 ml) was exposed to singlet oxygen at 0° C. for 4 hours. On evaporation, the residue was purified by a silica column using 60% ethyl acetate/hexane to give the desired furanone. IR(CHCl$_3$) 3400 and 1750–1850.

$^1$HNMR (CDCl$_3$) 1.25 (brs +m, 20H), 1.80 (m, 4H), 2.16 (s, 6H), 5.50 (brt, 2H), 5.70 (brs, 1H), 5.92 (brs, 2H) and 5.10 (br, 2H).

$^{13}$CNMR 21.0, 25.0, 29.2, 29.4, 29.6, 29.7, 33.1, 69.7, 69.9, 70.0, 98.6, 118.9, 119.0, 119.1, 119.3, 119.4, 167.7, 171.2 and 171.7.

LRMS m/e (% abundance) 510 (M+, 22) 468 (100), 451 (41), 408 (87), 391 (55), 390 (45), 364 (22) and 347 (19).

1,12-Di(N-phenylcarbamoyl)-1,12-bis(2-triethylsilyl-4-furyl)dodecane

2-Triethylsilyl-4-furaldehyde (100 mg, 0.5 mmol) was added to 1,10-dodecylmagnesium bromide (1.13 mmol; prepared from 339 mg, 1,10-dibromodecane and 61 mg magnesium twinings) in THF (1 ml) at 0° C. under argon. After the Grignard reagent was spent, phenyl isocyanate (0.26 ml, 2.38 mmol) was added. After stirring at room temperature for 14 hours, the mixture was quenched with water. Extraction (ethyl ether) and evaporation of the dried (magnesium sulfate) extracts gave an oil, which was purified by flash chromatography on silica using 10% ethyl acetate/hexane to give the titled carbamate.

IR (CHCl$_3$) 3440, 1735 and 1608.

$^1$H NMR (CDCl$_3$) (mixture of diasteromers) 0.75 (m, 2H), 0.95 (m, 18H), 1.25 (m, 16H), 1.85 (m, 4H), 5.80 (t, 2H, J=6.9 Hz), 6.32 (s, 1H), 6.65 (s, 1H), 6.8–7.65 (m, 10H), 7.61 (s, 1H) and 10.9 (br, 2H).

$^{13}$C NMR (CDCl$_3$) 2.78, 2.82, 6.93, 13.8, 22.4, 24.6, 25.2, 28.7, 28.8, 29.0, 29.1, 29.2, 29.4, 31.3, 34.7, 69.5, 72.6, 118.7, 119.1, 119.7, 120.0, 123.3, 124.0, 124.1, 124.9, 128.3, 128.8, 129.0, 137.3, 138.0, 138.2, 144.2, 144.7, 151.7, 153.4, 155.6, 159.5 and 159.7.

LRMS (FAB) (m/e, % abundance) 823.43 [(M+Na)+, 0.1].

1,12-Di(N-phenylcarbamoyl)-1,12-bis[5-hydroxy-295H)-furano-4-yl]dodecane (Compound 201)

A mixture of 1,12-di(N-phenylcarbamoyl)-1,12-bis(2-triethylsilyl-4-furyl)dodecane (250 mg. 0.31 mmol), Rose Bengal (ca. 3 mg) and water (1 ml) in tetrahydrofuran (40 ml) was exposed to singlet oxygen at 0° C. for 6 hours. On evaporation, the residue was purified by flash chromatography on silica using 60% ethyl acetate/hexane to give the titled furanone. IR (CHCl$_3$) 3420, 3300, 1760, 1730, 1600 and 1525.

$^1$HNMR (d$_6$-acetone) (mixture of diasteromers) 1.30 (m, 16H), 1.90 (m, 4H), 5.60 (br, 1H), 5.70 (br, 1H), 6.05, 6.45 (m, 4H), 7.00–7.65 (m, 10H), 8.9 (br, 2H).

$^{13}$C NMR (d$_6$-acetone) 25.3, 28.9, 29.2, 29.4, 29.7, 29.9, 30.0, 30.1, 30.2, 33.4, 70.2, 71.0, 98.4, 98.5, 98.9, 99.0, 118.5, 119.4, 119.6, 120.5, 120.6, 124.0, 124.8, 129.4, 129.9, 130.0, 130.1, 138.7, 139.3, 140.1, 153.9, 169.1, 170.4, 170.8, 206.7 and 206.8.

HRMS exact mass calculated for C$_{34}$H$_{41}$N$_2$O$_{10}$ 637.2761, found 637.2748.

1,14-Di(tert-butanoyloxy)-1,14-bis(2-triethylsilyl-4-furyl)tetradecane

2-Triethylsilyl-4-furaldehyde (1.05 g, 4.97 mmol) was added to 1,12-dodecylmagnesium bromide (2.43 mmol; prepared from 0.79 g of 1,12-dibromododecane and 127 mg magnesium twinings) in THF (10 ml) at 0° C. under argon. When all the furaldehyde was consumed, 2,2-dimethylpropionyl chloride (0.69 ml, 5.58 mmol) was added. Stirring was continued at room temperature for 14 hours and the mixture was quenched with water. Extraction (ethyl ether) and evaporation of the dried (magnesium sulfate) extracts gave an oil, which was purified by flash chromatography on silica using 5% ethyl ether/hexane to give the titled ester.

IR(CHCl$_3$) 1725.

$^1$H NMR (CDCl$_3$) 0.75 (q, 12H, J=6.8 Hz). 0.97 (t, 18H, J=6.8 Hz), 1.24 (m, 20H), 1.80 (m, 4H), 5.76 (t, 2H, J=7.8 Hz), 6.55 (s, 2H) and 7.56 (s, 2H).

$^{13}$C NMR (CDCl$_3$) (CDCl$_3$) 3.14, 7.22, 25.3, 27.0, 29.2, 29.4, 29.5, 29.6, 34.9, 38.7, 68.4, 119.6, 125.2, 143.9, 158.9 and 177.8.

1,14-Di(tert-butanoyloxy)-1,14-bis[5-hydroxy-2(5H)furans-4-yl]-tetradecane (Compound 202)

A mixture of 1,14-di(tert-butanoyloxy)-1-,14-bis(2-triethylsilyl-4-furyl)tetra (990 mg, 1.31 mmol), Rose bengal (5 mg) and water (1 ml) in acetone (70 ml) was exposed to singlet oxygen at 0° C. for 2 days. On evaporation, the residue was purified on a silica column using 40% ethyl acetate/hexane to give the desired furanone.

IR(CHCl$_3$) 3400 and 1730–1810.

$^1$H NMR (CDCl$_3$) 1.25 (m, 38H), 1.80 (m, 4H), 6.25 (br, 2H0, 5.40 (brt, 2H), 5.91 (s, 2H) and 6.05 (br, 2H).

$^{13}$CNMR 24.6, 26.7, 26.8, 28.7, 28.8, 29.0, 29.1, 32.8, 38.7, 69.2, 98.1, 111.5, 118.3, 118.4, 167.8, 170.4, 178.5 and 178.6.

HRMS (FAB) exact mass calculated for C$_{32}$H$_{50}$H$_{10}$N$_a$ (M+N$_a$)+617.3302, found 617.3289.

1,14-Di-(tert-butanoyloxy)-1,14-bis[5-(N-phenylcarbanoyl)-2(5H)-furano-4-yl]-tetradecane (Compound 203)

Phenyl isocyanate (0.10 ml, 0.93 mmol) was added to a mixture of 1,14-di(tert-butanoyloxy)-1,14-bis[5- hydroxy-2(5H)-furano-4-yl]-tetradecane (Compound 202 277 mg, 0.47 mmol) and copper (I) chloride (92 mg, 0.93 mmol) in N,N-dimethylformamide (3 ml) at 0° C. under argon. After 6 hours at 0° C., the mixture was quenched with water and extracted with ethyl acetate. The extracts were combined and washed successively with dilute Hcl, saturated $NaHCO_2$ and brine. Evaporation of the dried (magnesium sulfate) organic phase gave an oil, which was purified by flash chromatography on silica using 30% ethyl acetate/hexane to give the titled furanone.

IR ($CHCl_3$) 3340, 1810, 1770 and 1735.

$^1$H NMR ($CDCl_3$), 1.30 (m, 38H), 1.80 (m, 4H), 5.65 (t, 2H, J=5.3 Hz), 6.04 (s, 2H), 6.99 (s, 2H) and 7.00–7.50 (m, 10H).

HRMS (FAB) exact mass calculated for $C_{46}H_{60}N_2O_{12}Na$ (M=Na)+855.4044, found 855.4077.

EXAMPLE 19

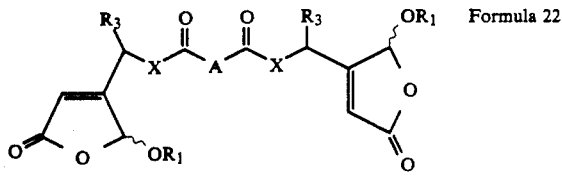

Formula 22

Compounds which are preferred in the method of treatment of the present invention and which are shown by Formula 22 above have the following preferred substituents.

With respect to the 5-position of the furanone moiety those compounds are preferred in the method of treatment of the present invention where the substituent is hydroxy (in Formula 22 $R_1$ is H) or acetoxy ($R_1$ is $COCH_3$).

With reference to the length of the alkyl chain (A) in the dicarboxylic acid residue (CO—A—CO) which connects the two (5-hydroxy-2(5H)-furano-yl)(1-hydroxy)alkyl or the two (5-hydroxy-2(5H)-furanoyl)-(lamino)alkyl moieties of the preferred compounds, the alkyl chain may contain between approximately 0 to 30 carbons; preferrably A is a straight chain divalent alkyl radical represented by $(CH_2)_n$ where n is an integer between 0 to 30, more preferably between 0 to 16 carbons.

With reference to the alkyl substituent on the alpha carbon in the 4-position of the furan nucleus of the preferred compounds ($R_3$ in Formula 22), the alkyl substituent may contain 5 to 20 carbons. Preferably the alkyl substituent ($R_3$) is n-alkyl, having 6 to 16 carbons.

The most preferred compounds of the invention are listed below with continuing reference to Formula 22, where for the purposes of the listed examples $R_1$=H and A=$(CH_2)_n$.

Compound 210: X=O, n=1, $R_3$=—$(CH_2)_{11}CH_3$;
Compound 211: X=O, n=3, $R_3$=—$(CH_2)_{11}CH_3$;
Compound 212: X=NH, n=3, $R_3$=—$(CH_2)_{11}CH_3$;
Compound 213: X=O, n=1, $R_3$=—$(CH_2)_5CH_3$;

The compounds of Example 19 can be made in accordance with the synthetic chemical pathways illustrated by the following specific examples. The practicing synthetic organic chemist can readily modify the chemical pathways provided by these specific reactions and examples to prepare any and all compounds represented by Formula 22.

4-(1-Hydroxytridecyl)-2-triethylsilylfuran

Dodecylmagnesium bromide (a 1M solution in tetrahydrofuran; 14.3 ml; 14.3 mmol) was added dropwise to a solution of 2-triethylsilyl-4-furaldehyde (2.0 g, 9.52 mmol) in THF (20 ml) at 0 degrees C. under argon. After stirring at room temperature for 2 hours, the mixture was quenched with dilute HCl and extracted with ethyl ether. Evaporation of the dried (magnesium sulfate) extracts gave an oil, which was purified by flash chromatography on silica using 30% ethyl ether/hexane to give the titled alcohol. $^1$HNMR ($CDCl_3$) 0.76 (q, 6H, J=8.0 Hz), 0.88 (t, 3H, J=6.3 Hz), 0.98 (t, 9H, J=8.0 Hz), 1.25 (m, 20H), 1.62 (d, 1H, J =4.3 Hz), 1.75 (m, 2H), 4.63 (dd, 1H, J=6.6 Hz, 1.9 Hz0, 6.63 (s, 1H) and 7.57 (s, 1H).

Bis[1-(2-triethylsilyl-4-furyl)tridecyl]malonate

Malonyl dichloride (49 ul, 0.5 mmol) was added dropwise to a solution of 4-(1-hydroxytridecyl)-2-triethylsilylfuran (0.40 g, 1.05 mmol) at 0 degrees C. After 5 minutes, diisopropylethylamine (0.17 ml, 1.0 mmol) was added and stirring was continued at 0 degrees C. for 3 hours. The mixture was quenched with water and extracted with (ethyl ether). Evaporation of the dried (magnesium sulfate) extracts gave an oil, which was purified by flash chromatography on sillica using 7.5 ethyl ether/hexane to give the titled ester.

$^1$HNMR ($CDCl_3$) 0.76 (q, 12H, J=8.0 Hz), 0.88 (t, 6H, J=6.9 Hz), 0.97 (t, 18H, J=8.0 Hz), 1.25 (m, 40H), 1.80 (m, 4H), 3.36 (s, 2H), 5.82 (t, 2H, J=6.6 Hz), 6.58 (s, 2H) and 7.60 (s, 2H).

$^{13}$C NMR ($CDCl_3$) 2.9, 7.0, 13.8, 22.5, 25.2, 29.0, 29.2, 29.3, 29.4, 29.5, 31.7, 34.4, 42.0, 69.9, 119.7, 124.4, 144.9, 159.6 and 166.3

LRMS (FAB) 851.6 (M+Na+).

Bis[1-(5-hydroxy-2(5H)-furano-4-yl)tridecyl]malonate (Compound 210)

A mixture of bis[1-(2-triethylsilyl-4-furyl)tridecyl]-malonate (226 mg, 0.27 mmol), Rose Bengal (5 mg) said water (1 ml) in acetone (20 ml) was exposed to singlet oxygen at 0 degrees C. for 7 hours. On evaporation, the residue was purified by flash chromatography on silica using 40% ethyl acetate/hexane to give the titled furanone.

IR ($CHCl_3$) 3400 and 1765.

$^1$HNMR ($CDCl_3$) 0.68 (t, 6H, J=7.0 Hz), 1.26 (m, 40H), 1.85 (br, 4H), 3.56 (br, 2H), 5.68 (br, 1H), 5.76 (br, 1H), 6.04 (s, 2H), 6.06 (s, 1H) and 6.25 (brs, 1H).

$^{13}$C NMR ($CDCl_3$) 13.8, 22.4, 24.7, 28.9, 29.1, 29.2, 29.3, 29.4, 31.7, 32.6, 40.6, 40.8, 70.4, 70.5, 71.2, 98.1, 118.8, 119.8, 119.9, 165.8, 166.3 and 171.0.

HRMS (FAB) exact mass calculated for $C_{37}H_{60}O_{10}Na$ 687.4084, found 687.4091.

Di[1-(2-triethylsilyl-4-furyl)]tridecyl 1,5-pentandioate n-Dodecylmagnesium bromide (a 1.0M solution in THF; 7.52 ml; 7.52 mmol) was added to a solution of 2-triethylsilyl-4-furaldehyde (1.58 g, 7.52 mmol) in THF (20 ml) at 0 degrees C. under argon. The mixture was warmed to room temperature. When all the aldehyde was consumed, as shown by TLC, the mixture was recooled to 0 degrees C. and 1,5-pentandioyl chloride (0.44 ml, 3.42 mmol) was added. Stirring was continued at room temperature overnight and the mixture was quenched wtih 5% ammonium chloride solution. Extraction (ethyl ether) and evaporation of the dried (magnesium sulfate) extracts gaven an oil. The crude product was purified by flash chromatography (SiO$_2$, 5% ethyl ether/hexane) to give the titled furan.

IR (CHCl$_3$) 1725;
$^1$HNMR (CDCl$_3$) 0.75, (q, 12H, J=7.5 Hz), 0.88 (t, 6H, J=6.9 Hz), 0.94 (t, 18H, J=7.5 Hz), 1.25 (brs, 40H), 1.80 (m, 4H), 1.95 (p, 2H, J=6.2 Hz), 2.33 (t, 4H, J=6.2 Hz), 5.80 (t, 2H, J=7.5 Hz), 6.58 (s, 2H) and 7.59 (s, 2H).
$^{13}$C NMR (CDCl$_3$) 2.89, 6.99, 13.8, 20.1, 22.5, 25.3, 29.1, 29.2, 29.3, 29.4, 31.7, 33.4, 34.6, 68.6, 119.7, 124.9, 144.7, 159.5 and 172.7.

4-(1-Azidotridecyl)-2-triethylsilylfuran

A solution of diphenylphosphozylazide (143 mg, 0.52 mmol) in THF (2 ml) was added over a period of 15 minutes to a solution of 4-(1-hydroxytridecyl)-2-triethylsilylfuran (200 mg, 0.52 mmol), triphenylphosphine (140 mg, 0.52 mmol) and diethyl azidocarboxylate (90 mg, 0.52 mmol) in THF (10 ml) at room temperature. After stirring for 2 days, the mixture was evaporated in the presence of a minimum amount of silica gel. The residue was purified by flash chromatography o silica using 5% ethyl ether/hexane to give the titled azide.

$^1$HNMR (CDCl$_3$) 0.77 (q, 6H, J=8.0 Hz), 0.88 (t, 3H, J=6.4 Hz), 0.98 (t, 9H, J=8.0 Hz), 1.25 (m, 20H), 1.75 (m, 2H), 4.33 (t, 1H, J=7.5 Hz), 6.60 (s, 1H) and 7.61 (s, 1H).

4-(1-Aminotridecyl)-2-triethylsilylfuran

A solution of lithium aluminum hydride (a 1.0M solution in THF; 4.22 ml, 4.22 mmol) was added slowly to a solution of 4-(1-azidotridecyl)-2-triethylsilylfuran (1.55 g, 3.84 mmol) at 0 degrees C. under argon. After stirring at room temperature for 2 hours, the mixture was cooled to 0 degrees C. and quenched with 2M sodium hydroxide. Anhydrous sodium sulfate was added to coagulate the aluminum salt and the mixture was extracted thoroughly with ethyl acetate. Evaporation of the dried (magnesium sulfate) extracts gave an oil, which was purified by flash chromatography on silica using 5% methanol/dichloromethane to give the titled amine.

$^1$H NMR (CDCl$_3$) 0.76 (q, 6H, J=8.0 Hz), 0.88 (t, 3H, J=6.5 Hz), 0.98 (t, 9H, J=8.0 Hz), 1.25 (m, 20H), 1.80 (m, 2H), 3.95 (t, 1H, J=6.8 Hz), 6.60 (s, 1H) and 7.50 (s, 1H).

N,N'-bis[2-triethylsilyl-4-furyl)tridecyl]-1,5-pentadiamide 1,5-Pentanoyl dichloride (50 ul, 0.39 mmol), followed by triethylamine (0.11 ml, 0.79 mmol) was added to a solution of 4-(1-aminotridecyl)-2-triethylsilylfuran (142 mg, 0.38 mmol) in dichloromethane at room temperature. After stirring for 15 hours, the mixture was quenched with water and extracted with ethyl ether. Evaporation of the dried (magnesium sulfate) extracts gave an oil, which was purified by flash chromatography to give the titled amide. R$_f$(50% ethyl ether/hexane) 0.09

$^1$H NMR (CDCl$_3$) 0.74 (q, 12H, J=7.9 Hz) 0.89 (t, 6H, J=6.8 Hz), 0.98 (q, 18H, J=7.9 Hz), 1.26 (brs, 40H), 1.70 (brm, 4H), 2.0 (m, 2H), 2.25 (m, 4H), 5.0 (q, 2H, J=7.5 Hz), 5.58 (m, 2H), 6.55 (s, 2H), 7.53 (s, 1H) and 7.54 (s, 1H).

N,N'-bis[1-(5-hydroxy-2(5H)-furanon-4-yl)tridecyl]-1,5-pentadiamide (Compound 212)

Singlet oxygen oxidation of N,N'-bis[triethylsilyl-4-furyl)tridecyl]-1,5-pentadiamide, under the usual condition, gave the titled furanone.

Di[1-(5-hydroxy-2(5H)-furanon-4-yl)]tridecyl 1,5-pentandioate (Compound 211)

A mixture of di[1-(2-triethylsilyl-4-furyl)]tridecyl 1.5-pentandioate (1.98 g, 2.32 mmol), Rose Bengal (ca, 5 mg) and water 2 ml) in THF (150 ml) was exposed to singlet oxygen at 0 degrees C. for 7 hours. The residue, after evaporation, was purified by flash chromatography (SiO$_2$, 30% ethyl acetate/hexane) to give the titled furanone.

IR (CHCl$_3$) 3500–3300, 1750;
$^1$HNMR (CDCl$_3$) 6.89 (t, 6H, J=6.8 Hz), 1.27 (brm, 40H), 1.83 (m, 4H), 1.99 (m, 2H), 2.44 (t, 4H, J=6.9 Hz), 5.57 (t, 2H, J=6.2 Hz), 5.85 (br, 2H), 6.00 (s, 1H), 6.02 (s, 1H) and 6.15 (br, 2H).
$^{13}$C NMR (CDCl$_3$) 13.8, 19.4, 19.6, 22.5, 24.9, 29.0, 29.1, 29.2, 29.4, 29.5, 31.8, 32.8, 32.9, 69.7, 98.4, 118.9, 119.0, 119.1, 119.3, 166.9, 167.0, 170.8, 170.9 and 173.1.

Di[(1-2-triethylsilyl-4-furyl)heptyl]malonate

Using the same procedure as for di[1-2(triethylsilyl-4-furyl)]-tridecyl 1,5-pentandioate except using hexyl magnesium bromide and malonyl dichloride instead of dodecylmagnesium bromide and 1,5-pentanoyl dichloride respectively, the title compound was obtained.

IR (CHCl$_3$) 1740, 1725
$^1$H NMR (CDCl$_3$) 0.77 (q, 12H, J=7.5 Hz), 0.87 (t, 6H, J=6.8 Hz), 0.96 (t, 18H, J=7.5 Hz), 1.26 (brs, 20H), 3.56 (s, 2H), 5.83 (t, 2H, J=7.4 Hz), 6.58 (s, 2H) and 7.59 (s, 2H0
$^{13}$C NMR (CDCl$_3$) 2.89, 6.98, 13.7, 22.3, 25.1, 28.7, 31.4, 34.4, 41.9, 69.9, 119.7, 124.5, 144.9, 159.6 and 166.3.

Di[(1-5-hydroxy-2(5H)-furanon-4-yl)heptyl]malonate (Compound 213)

A mixture of di[(1-2-triethylsilyl-4-furyl)heptyl]malonate (680 mg, 1.37 mmol) Rose Bengal (ca, 5 mg) and water (1 ml) in acetone (100 ml) was exposed to singlet oxygen at 0 degrees C. for 7 hours. The residue, after evaporation, was purified by flash chromatography (SiO$_2$, 30% ethyl acetate/hexane) to give the titled furanone.

IR (CHCl$_3$) 3500–3300, 1800–1720
$^1$H NMR (CDCl$_3$) 0.88 (t, 6H, J=6.9 Hz), 1.25 (brm, 12H), 1.83 (m, 4H), 3.53 (brm, 2H), 5.25 (br, 2H), 5.65 (t, 2H, J=5.9 Hz) and 6.06 (brs, 4H0
$^{13}$C NMR (CDClv3v) 13.7, 22.3, 24.6, 28.5, 31.3, 32.5, 40.7, 40.8, 60.5, 70.6, 70.7, 70.8, 70.9, (br), 98.2, 118.8, 118.9, 119.0, 119.7, 166.2 and 170.9.

EXAMPLE 20

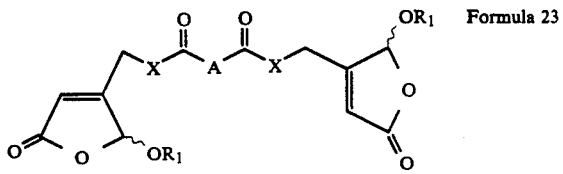

Formula 23

Compounds which are preferred in the method of treatment of the present invention and which are shown by Formula 23 above have the following preferred substituents. With respect to the 5-position of the furanone moiety, those compounds are preferred where the substituent is hydroxy (in Formula 1 $R_1$ is H), acetoxy ($R_1$ is $COCH_3$), 2,2-dimethylpropionyloxy ($R_1$ is $CH_3-C(CH_3)_2-CO$) or where $R_1$ is $CONHR_2$ and $R_2$ is lower alkyl or phenyl, more preferably phenyl.

With reference to the length of the alkyl chain (A) which connects the two (5-hydroxy-2(5H)-furanoyl)methanol or the two (5-hydroxy-2(5H)-furanoyl)methylamin moieties of the compounds, the alkyl chain may contain between approximately 5 to 30 carbons; preferrably A is a straight chain divalent alkyl radical represented by $(CH_2)_n$ where n is an integer between 5 to 30, more preferably between 6 to 16 carbons.

Examples of preferred compounds are listed below with continuing reference to Formula 23. For the purposes of the listed examples $A=(CH_2)_{10}$, and the two substituents on the 5-hydroxy group, that is the two $R_1$ groups are differentiated as $R_1'$ and as $R_1''$.

Compound 220 X=O, $R_1'$=H, $R_1''$=H;
compound 221 X=O, $R_1'$=$CH_3-C(CH_3)_2-CO$, $R_1''$=$CH_3-C(CH_3)_2-CO$;
Compound 222 X=NH, $R_1'$=H, $R_1''$=H;
Compound 223 X=NH, $R_1'$=$CONH$-phenyl, $R_1'$=$CONH$-phenyl;
Compound 224 X=NH, $R_1'$=H, $R_1''$=$CONH$-phenyl.

The compounds of Example 20 can be made in accordance with the synthetic chemical pathways illustrated by the following specific examples. The practicing synthetic organic chemist can readily modify the chemical pathways provided by these specific reactions and examples to prepare any and all compounds represented by Formula 23.

4-Hydroxymethyl-2-trimethylsilylfuran

2-Trimethylsilyl-4-furaldehyde (1.57 g, 9.35 mmol) was added to a suspension of sodium borohydride (424 mg, 11.2 mmol) in methanol (10 ml) at 0° C. After 45 minutes, most of the methanol was evaporated and the residue taken up in ethyl ether. The ethyl ether extracts were combined, washed (water), dried (magnesium sulfate) and evaporated to dryness to give an oil, which was purified by flash chromotography on silica using 30% ethyl ether/hexane to give the title alcohol as a pale yellow oil.

$^1$H NMR (CDCl$_3$): 7.57 (s, 1H); 6.64 (s, 1H); 4.50 (s, 2H); 2.75 (broad s, 1H); 0.25 (s, 9H).
$^{13}$C NMR (CDCl$_3$): 161.5, 144.0, 125.0, 119.7, 56.2, −1.8.
HRMS exact mass calculated for $C_8H_{14}O_2Si$: 170.0763, obtained (EI+): 170.0766.

4-Hydroxymethyl-2-triethylsilylfuran

Sodium borohydride (353 mg, 0.93 mmol) was added portionwise to a solution of 2-triethylsilyl-4-furaldehyde (1.64 g, 7.79 mmol) in methanol (10 ml) at 0°. After 1 hour, most of the methanol was evaporated and the residue dissolved in a minimum amount of dilute hydrochloric acid. Extraction (ethyl acetate), drying (magnesium sulfate) and evaporation gave an oil, which was purified by flash chromatography on silica using 20% ethyl ether/hexane. Fractions with $R_f$ of about 0.07 (10% ethyl ether/hexane) gave after evaporation the title alcohol as a colorless oil.

$^1$HNMR (CDCl$_3$) 0.76 (q, 6H, J=7.4 Hz), 0.97 (t, 9H, J=7.5 Hz), 1.45 (t, 1H, J=5.3 Hz), 4.56 (d, 2H, J=5.3 Hz), 6.67 (s, 1H) and 7.62 (s, 1H).

HRMS exact mass calculated for $C_{11}H_{20}SiO_2(M+)$ 212.1233 found 212.1231.

(E),(Z)-)-O-Methyl-2-triethylsilyl-4-furaldehyde oxime

A solution of sodium acetate (1 g, 12.3 mmol) and methoxylamine hydrochloride (1.05 g, 12.3 mmol) in water (5 ml) was added to a solution of 2-triethylsilyl-4-furaldehyde (860 mg, 4.1 mmol) in ethanol (6 ml) at room temperature. After stirring for 16 hours, most of the ethanol was evaporated and the residue dissolved in water. Extraction (ethyl acetate) and evaporation of the dried (magnesium sulfate) extracts gave an oil, which was purified by flash chromatography on silica using 5% ethyl ether/hexane to give the title oxime as a colorless oil.

$^1$HNMR (CDCl$_3$) 0.79 (q, 6H, J=7.3 Hz), 0.99 (t, 9H, J=7.9 Hz), 3.95 (s, 3H), 4.06 (s, 3H), 6.84 (s, 1H), 7.00 (s, 1H), 7.28 (s, 1H), 7.82 (s, 1H), 8.05 (s, 1H) and 8.34 (s, 1H).

HRMS exact mass calculated for $C_{12}H_{21}NO_2Si(M+)$ 239.1341, found 239.1332.

4-Aminomethyl-2-triethylsilylfuran

Lithium aluminum hydride (a 1.0M solution in tetrahydrofuran; 0.54 ml, 0.54 mmol) was added dropwise to a solution of (E),(Z)-O-methyl-2-triethylsilyl-4-furaldehyde oxime (Compound 12, 106.2 mg, 0.46 mmol) in tetrahydrofuran (5 ml) at room temperature. After stirring at room temperature overnight (ca. 14 hours), the reaction mixture was quenched with water. Extraction (ethyl ether) and evaporation of the dried (magnesium sulfate) extracts gave an oil, which was purified by flash chromatography on silica using 10% methanol/dichloromethane/1% ammonia. Fractions with $R_f$ of about 0.34 gave after evaporation the title amine as a pale yellow oil.

$^1$H NMR (CDCl$_3$) 0.76 (q, 6H, J=7.9 Hz), 0.98 (t, 9H, J=8.4 Hz), 1.87 (br s, 2H), 3.76 (s, 2H), 6.63 (s, 1H) and 7.56 (s, 1H).

HRMS exact mass calculated for $C_{11}H_{21}SiNO(M+)$ 211.1392, found 211.1389.

Di-(2-triethylsilyl-4-furyl)methyl dodecan-1,12-dioate 1,12-Dodecanedioyl dichloride (0.44 ml, 1.74 mmol) followed by triethylamine (0.51 ml, 3.65 mmol) was added to a solution of 4-hydroxymethyl-2-triethylsilylfuran (756 mg, 3.57 mmol) in THF (10 ml) at 0 degrees C. After stirring at room temperature overnight, the mixture was diluted with ethyl ether and washed successively with saturated $NaHCO_3$, water and brine. Evaporation of the dried (magnesium sulfate) organic phase gave an oil, which was purified on a silica column using 3% ethyl ether/hexane to give the titled ester.

IR (neat) 1750.
$^1$H NMR (CDCl$_3$) 0.73 (q, 12H, J=7.0 Hz), 0.95 (t, 18H, J=7.0 Hz), 1.22 (br, 12H), 1.60 (m, 4H), 2.28 (t, 4H, J=7.0 Hz), 4.95 (s, 4H), 6.61 (s, 2H) and 7.63 (s, 2H).
$^{13}$CNMR (CDCl$_3$) 2.84, 6.93, 24.7, 28.8, 29.0, 29.1, 34.1, 57.4, 77.4, 120.4, 121.5, 145.9, 159.8 and 174.0.
HRMS exact mass calculated for $C_{34}H_{62}NO_6Si_2$ $(M+NH_4)+$636.4116, found 636.4109.

Di-[5-hydroxy-2(5H)-2-oxo-4-furyl]methyl dodecan-1,12-dioate (Compound 220)

A mixture of di-(2-triethylsilyl-4-furyl)methyl dodecan-1,12-dioate (977 mg, 1.58 mmol), Rose Bengal (ca. 3 mg) and water (ca. 1 ml) in THF (150 ml) was exposed to singlet oxygen at 0 degrees C. for 8 hours. The mixture was filtered and evaporated to dryness to give a solid, which was purified by flash chromatography on silica using 30% ethyl acetate/hexane to give the titled bis-furanone.

IR (CHCl$_3$) 1750.

$^1$HNMR (CDCl$_3$) 1.25 (brs, 12H), 1.55 (brm, 4H), 2.41 (t, 4H, J=7.4 Hz), 4.92 (ddd, 4H, J=16.9 Hz, 1.7 Hz), 6.13 (brs, 4H) and 8.10 (br, 2H)

$^{13}$CNMR (CDCl$_3$) 24.2, 28.3, 28.6, 28.7, 33.1, 38.7, 38.9, 39.2, 39.4, 39.8, 40.1, 40.3, 58.8, 97.7, 117.4, 165.1, 170.3 and 172.8.

HRMS exact mass calculated for C$_{22}$H$_{31}$O$_{10}$ (M+H)$^+$455.1917, found 455.1916.

Di-[5-tert-butanoyloxy-2(5H)-furano-4-yl]methyl dodecan-1,12-dioate (Compound 221)

Ethyl diisopropylamine (52 microliter,, 0.30 mmol), followed by 2,2-dimethylpropionyl chloride (37 microliter, 0.30 mmol) was added to a solution of di-[5-hydroxy-2(5H)-furano-4-yl]methyl dodecan-1,12-dioate (59 mg, 0.13 mmol) in THF (2 ml) at 0 degrees C. under argon. After stirring at 0 degrees C. for 3 hours, the mixture was diluted with ethyl ether and washed successively with water, NaHCO$_3$ solution and brine. Evaporation of the dried (magnesium sulfate) organic layer gave an oil, which was purified by flash chromatography on silica using 20% ethyl acetate/hexane to give the titled diester.

IR (CHCl$_3$) 1800, 1760

$^1$HNMR (CDCl$_3$) 1.21 (s, 18H), 1.23 (br, 12H), 1.60 (m, 4H), 2.35 (t, 4H, J=7.7 Hz), 4.85 (brs, 4H), 6.13 (brs, 2H) and 6.91 (brs, 2H).

$^{13}$CNMR (CDCl$_3$) 24.5, 26.6, 28.8, 28.9, 29.1, 33.6, 38.8, 58.0, 92.6, 119.9, 161.2, 169.1, 173 and 176.6.

HRMS, exact mass calculated for C$_{32}$H$_{50}$NO$_{12}$ (M+NH$_4$)$^+$640.3333, found 640.3312.

N,N'-Bis(2-triethylsilyl-4-furyl)methyl-1,12-dodecanoic acid amide

Diisopropylethylamine (0.46 ml, 2.65 mmol), followed by 1,12-dodecanedioyl dichloride (0.32 ml, 1.26 mmol) was added to a solution of 4-aminomethyl-2-triethylsilylfuran (Compound 8, 533 mg, 2.53 mmol) in dichloromethane at 0 degrees C. under argon. After stirring at room temperature for 8 hours the mixture was quenched with water. Extraction (ethyl ether) and evaporation of the dried (magnesium sulfate) extracts gave an oil which was purified by flash chromatography on silica using 1% methanol/chloroform to give the titled amide.

IR (CHCl$_3$) 1675, 1625, 1510.

$^1$HNMR (CDCl$_3$) 0.75 (q, 12H, J=7.9 Hz), 0.96 (t, 18H, J=7.9 Hz), 1.25 (m, 12H), 1.65 (m, 4H), 2.18 (t, 4H, J=7.8 Hz), 4.24 (d, 4H, J=5.5 Hz), 6.50 (brt, 2H), 6.58 (s, 2H) and 7.53 (s, 2H).

$^{13}$C NMR (CDCl$_3$) 2.72, 6.81, 20.3, 25.4, 28.8, 28.9, 29.0, 29.1, 33.8, 36.2, 45.2, 121.2, 144.2, 159.5 and 173.3.

HRMS exact mass calculated for C$_{34}$H$_{61}$N$_2$O$_4$Si$_2$(M+H)$^+$617.4170, found 617.4197.

N,N'-Bis(5-hydroxy-2(5H)-2-oxo-4-furyl)methyl-1,12-dodecanoic acid amide (Compound 222)

A mixture of N,N-bis (2-triethylsilyl-4-furyl)methyl-1,12-dodecanamide (463 mg, 0.75 mmol), Rose Bengal (ca, 3 mg) and water (1 ml) in THF (50 ml) was exposed to singlet oxygen at 0 degrees C. for 5 hours. The mixture was filtered and the filtrate evaporated to dryness to give an oil, which was purified by flash chromatography on silica using 10% methanol/chloroform to give the titled furanone.

IR (CHCl$_3$) 1758, 1661 and 1548.

$^1$H NMR (CD$_3$OD) 1.23 (brs, 12H), 1.62 (brm, 4H), 2.26 (t, 4H, J=7.7 Hz), 4.15 (brs, 4H), 5.89 (brd, 2H, J=1.0 Hz) and 6.09 (brs, 2H)

$^{13}$C NMR (CD$_3$OD) 26.8, 30.2, 30.3, 30.4, 36.8, 37.6, 100.5, 100.6, 118.5, 169.1, 173.1 and 177.0.

HRMS exact mass calculated for C$_{22}$H$_{33}$N$_2$O$_8$ (M+H)$^+$453.2236, found 453.2247.

Bis-[(2-triethylsilyl-4-furyl)methyl]oxalate

Oxalyl chloride (0.59 ml, 6.79 mmol) was added dropwise to a solution of 4-hydroxymethyl-2-triethylsilylfuran (1.2 q, 5.66 mmol) and triethylamine (0.95 ml, 6.79 mmol) in dichloromethane (10 ml) at 0 degrees. After 10 minutes, the reaction mixture was quenched with ice. Extraction (dichloromethane) and evaporation of the dried (magnesium sulfate) extracts gave an oil, which was purified by flash chromatography on silica using 5% ethyl ether/hexane. Fractions with R$_f$ of about 0.17 gave, after evaporation, the title oxalate ester as a colorless oil. (83%).

$^1$HNMR (CDCl$_3$) 0.81 (q, 6H, J=7.3 Hz), 1.02 (t, 9H, J=7.3 Hz), 5.24 (s, 2H), 6.73 (s, 1H) and 7.78 (s, 1H).

MS m/e (% abundance) 195(100), 167(16), 115(35) and 87(29).

Singlet oxygen oxidation of bis-[(2-triethylsilyl-4-furyl)methyl]oxalate in the presence of water, gives the corresponding bis-furanone.

N-(5-Hydroxy-2(5H)2-oxo-4-furyl)methyl-N'-(5-phenylcarbamoyloxy-2(5H)2-oxo-4-furyl)methyl-1,12-dodecanamide (Compound 223) and N,N'-bis(5-phenylcarbamoyloxy-2(5H)2-oxo-4-furyl)-methyl-1,12-dodecanamide (Compound 224)

Phenyl isocyanate (29 microliter, 0.27 mmol) was added to a mixture of N,N'-bis(5-hydroxy-2(5H)-oxo-4-furyl)methyl-1,12-dodecanamide (Compound 222, 116 mg, 0.26 mmol) and copper (I) chloride (27 mg, 0.27 mmol) in DMF (2 ml) at 0 degrees C. under argon. After stirring for 3 hours, the mixture was quenched with water. Extraction (ethyl ether) and evaporation of the dried (magnesium sulfate) extracts gave an oil, which was purified by flash chromatography (10% methanol/chloroform) to give the titled mono-and bis-carbamates. Mono-carbamate (Compound 223): R$_f$ (10% methanol/chloroform) 0.21

IR (CHCl$_3$) 3600–3400, 1720 and 1530

$^1$H NMR (CDCl$_3$) 1.27 (m, 12H), 1.60 (m, 4H), 2.25 (t, 4H, J=7.7 Hz), 4.20 (m, 2H), 4.35 (m, 2H), 5.89 (brs, 1H), 6.11 (brs, 2H), 6.99 (s, 1H), 7.05–7.60 (m, 5H) and 7.70 (m, 2H), LRMS (FAB) m/e (% abundance) 594 [(M+Na)$^+$, 20).

Bis-carbamate (Compound 224): R$_f$(10% methanol/chloroform) 0.37

IR (CHCl$_3$) 3700, 3500–3300, 1805, 1775, 1720, 1680, 1610 and 1540–1520

$^1$HNMR (CDCl$_3$) 1.27 (m, 12H), 1.60 (m, 4H), 2.25 (t, 4H, J=7.9 Hz), 4.20 (dd, 1H, J=17.4 Hz, 4.9 Hz), 4.35 (dd, 1H, J=17.4 Hz, 4.9 Hz), 6.01 (br, 1H), 6.12 (s, 1H), 6.45 (br, 1H), 6.80 (t, 1H), 6.95 (brd, 1H), 6.99 (s, 2H), 7.08 (t, 2H, J=7.6 Hz), 7.20 (t, 4H), 7.35 (m, 4H), 7.50 (brd, 4H), 7.59 (m, 4H), 7.85 (brt, 2H)

LRMS (FAB) m/e (% abundance) 713.8 [(M+Na)$^+$,50].

What is claimed is:

1. A method for treating an imbalance between bone production and resorption in a host mammal in need thereof who is in need of such treatment, for the purpose of decreasing the rate of bone resorption relative to bone production, the method comprising the step of administering to the mammal an effective dose of a compound, or a pharmaceutically acceptable salt thereof, of the formula

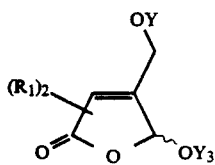

Formula 20a or a compound, or a pharmaceutically acceptable salt thereof, of

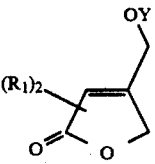

Formula 20b where
R₁ independently is phenyl or alkyl of 1 to 6 carbons, the R₁ groups being attached to the 3 and 5 positions of the 2-furanone;
Y is CO—R₃, or CO—NHR₃ and R₃ is $C_6$-$C_{20}$ alkyl, and
Y₃ is H or CO—R₄ where R₄ is alkyl of 1 to 6 carbons.

2. A method of claim 1 where the compound, or a pharmaceutically acceptable salt thereof, is administered in a daily dose of approximately 0.05 to 100 mg per kilogram of body weight of the host to be treated.

* * * * *

UNITED STATES PATENT AND TRADEMARK OFFICE
CERTIFICATE OF CORRECTION

PATENT NO. : 5,268,387
DATED : December 7, 1993
INVENTOR(S) : Michael E. Garst

It is certified that error appears in the above-identified patent and that said Letters Patent is hereby corrected as shown below:

Column 6, lines 42-44, put "$R_4$ is ... $NHSO_2N(C_2H_5)_2$;" into an individual paragraph;

Column 6, in Formula 11, the bond in the upper horizontal part of the 5-membered ring should be -- -- instead of "=";

Column 7, line 59, after "(" delete "-";

Column 17, in the table, Compound 36 & Compound 37, both "R"s should be --$R_1$--;

Column 18, line 41, after formula 26 insert the --(USP 5,403,457 400 23 PA, formula 9 of the patent)--;

Column 20, line 5, after "Y=" delete "-";

Column 22, line 57, before "(5H)" add --2--;

Column 22, line 61, before "Compound" add --(--;

Column 23, line 26, after "(" delete"-";

column 23, line 45, "Which" should be --which--;

Column 25, line 60, "Chain" should be --chain--;

Column 32, line 2, "2.67(m, H)," should be --2.67(m, 2H)--;

Column 45, line 42, after "($CDCl_3$)" add --:--;

Column 47, line 62, after "($CDCl_3$)" add --:--;

UNITED STATES PATENT AND TRADEMARK OFFICE
CERTIFICATE OF CORRECTION

PATENT NO. : 5,268,387
DATED : December 7, 1993
INVENTOR(S) : Michael E. Garst

It is certified that error appears in the above-identified patent and that said Letters Patent is hereby corrected as shown below:

Column 49, line 61, "2H" should be --12H--;

Column 53, line 24, "o" should be --on--.

Signed and Sealed this

Fourth Day of October, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,268,387

DATED : December 7, 1993

INVENTOR(S) : Michael E. Garst

It is certified that error appears in the above-identified patent and that said Letters Patent is hereby corrected as shown below:

Column 1, line 43, "resoption" should be --resorption--;

Column 3, line 47, "R'", should be --$R_1$--;

Column 7, line 55, "pheny" should be --phenyl--;

Column 28, line 55-56, "thoroughy" should be --throughly--;

Column 30, line 11, "1H0" should be --1H)--;

Column 32, line 36, "5.86(s 1H)." should be --5.86(s, 1H).--;

Column 32, line 64, after "solution" delete one ".";

Column 36, lines 27 and 45, "'H" should be --$^1$H--;

Column 37, lines 1, 17, 35 and 60, "'H" should be --$^1$H--;

Column 38, lines 9, 28 and 50, "'H" should be --$^1$H--;

Column 39, lines 32 and 61, "'H" should be --$^1$H--;

Column 40, lines 21 and 43 "'H" should be --$^1$H--;

Column 41, line 18, "'H" should be --$^1$H--;

Column 41, line 19, "6.6(Hz)," should be --6.6 Hz)--;

Column 41, line 24, "7.1  11.9," should be --7.1, 11.9--;

Column 41, line 41, "'H" should be --$^1$H--;

Column 41, line 60, "'H" should be --$^1$H--;

Column 41, line 62, after "9.91" (s, 1H)" add --.--;

Column 41, line 64, after "122.5" add --,--;

Column 42, lines 16 and 26, "'H" should be --$^1$H--;

Column 42, line 39, after "120 (27)" add --,--;

Column 42, line 59, before "500 mg," add --(--;

UNITED STATES PATENT AND TRADEMARK OFFICE
CERTIFICATE OF CORRECTION

PATENT NO. : 5,268,387

DATED : December 7, 1993

INVENTOR(S) : Michael E. Garst

It is certified that error appears in the above-identified patent and that said Letters Patent is hereby corrected as shown below:

Column 45, line 18, "(S, 3H);" should be --(s, 3H);--;

column 45, line 65, after "104.4" insert --,--;

Column 47, line 6, "solutin" should be --solution--;

column 48, line 16, "5.04 (S, 1H);" should be --5.04(s, 1H);-- and "5.07 (S, 1H);" should be --5.07(s, 1H);--;

Column 49, line 18, "6 HO," should be --6 H)--;

Column 50, line 43, delete one "($CDCl_3$)";

Column 50, line 57, "2 HO" should be --2 H)--;

Column 51, line 7, "Hcl" should be --HCl--;

Column 52, line 15, "HzO," should be --Hz),--;

Column 54, line 52, "4H0" should be --4H)--;

Column 54, line 53, "(CDClv3v)" should be --($CDCl_3$)--;

Column 54, line 54, before "(br)" delete --,--;

Column 58, line 55, "20)." should be --20]--;

UNITED STATES PATENT AND TRADEMARK OFFICE
CERTIFICATE OF CORRECTION

PATENT NO. : 5,268,387
DATED : December 7, 1993
INVENTOR(S) : Michael E. Garst

It is certified that error appears in the above-indentified patent and that said Letters Patent is hereby corrected as shown below:

Column 46, line 10, "fractins" should be ---fractions---.

Signed and Sealed this

Twentieth Day of December, 1994

Attest:

BRUCE LEHMAN

Attesting Officer    Commissioner of Patents and Trademarks